(12) United States Patent
Cahoon et al.

(10) Patent No.: US 10,280,431 B2
(45) Date of Patent: May 7, 2019

(54) ACYLTRANSFERASES AND METHODS OF USING

(71) Applicant: NUtech Ventures, Lincoln, NE (US)

(72) Inventors: Edgar Cahoon, Lincoln, NE (US); Umidjon Iskandarov, Lincoln, NE (US); Hae Jin Kim, Lincoln, NE (US); Jillian Collins-Silva, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 290 days.

(21) Appl. No.: 14/576,135

(22) Filed: Dec. 18, 2014

(65) Prior Publication Data

US 2016/0237448 A1 Aug. 18, 2016

Related U.S. Application Data

(60) Provisional application No. 61/917,587, filed on Dec. 18, 2013.

(51) Int. Cl.
*C12N 15/82* (2006.01)
*C12P 7/64* (2006.01)

(52) U.S. Cl.
CPC ........ *C12N 15/8247* (2013.01); *C12P 7/6463* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 7,135,617 B2* | 11/2006 | Lardizabal | C12N 9/1029 800/281 |
| 2013/0029387 A1* | 1/2013 | Nikolau | C12N 9/16 435/134 |
| 2013/0316410 A1* | 11/2013 | Franklin | C12Y 302/01014 435/134 |
| 2014/0223600 A1* | 8/2014 | Kaijalainen | C12N 9/0083 800/281 |

OTHER PUBLICATIONS

Liu et al (Diacylglycerol acyl transferase 1 overexpression detoxifies cardiac lipids in PPARr transgenic mice. Journal of Lipid Research vol. 53, 1482-1492, 2012).*
Arroyo-Caro et al., "The multigene family of lysophosphatidate acyltransferase (LPAT)-related enzymes in Ricinus communis: cloning and molecular characterization of two LPAT genes that are expressed in castor seeds," Plant Sci. Feb. 2013;199-200:29-40. doi: 10.1016/j.plantsci.2012.09.015. Epub Nov. 10, 2012.
Chang et al., "A simple and efficient method for isolating RNA from pine trees," Plant molecular biology reporter 1993, 11.2: 113-116.
Coleman, "Characterization of the *Escherichia coli* gene for 1-acyl-sn-glycerol-3-phosphate acyltransferase (plsC)," Mol Gen Genet. Mar. 1992;232(2):295-303.
Dehesh et al., "Two novel thioesterases are key determinants of the bimodal distribution of acyl chain length of Cuphea palustris seed oil," Plant Physiol. Jan. 1996;110(1):203-10.
Dehesh et al., "Production of high levels of 8:0 and 10:0 fatty acids in transgenic canola by overexpression of Ch FatB2, a thioesterase cDNA from Cuphea hookeriana," Plant J. Feb. 1996;9(2):167-72.
Gietz et al., "Studies on the transformation of intact yeast cells by the LiAc/SS-DNA/PEG procedure," Yeast. Apr. 15, 1995;11(4):355-60.
Knutzon, et al., "Lysophosphatidic acid acyltransferase from coconut endosperm mediates the insertion of laurate at the sn-2 position of triacylglycerols in lauric rapeseed oil and can increase total laurate levels," Plant Physiol. Jul. 1999;120(3):739-46.
Liu et al., "Development of ultra-high erucic acid oil in the industrial oil crop Crambe abyssinica," Plant Biotechnol J. Sep. 2012;10(7):862-70. doi: 10.1111/j.1467-7652.2012.00709.x. Epub May 30, 2012.
Lu and Kang, "Generation of transgenic plants of a potential oilseed crop *Camelina sativa* by Agrobacterium-mediated transformation," Plant Cell Rep. Feb. 2008;27(2):273-8. Epub Sep. 27, 2007.
Mañas-Fernández et al., "Cloning and molecular characterization of a class A lysophosphatidate acyltransferase gene (EpLPAT2) from Echium (Boraginaceae)," European Journal of Lipid Science and Technology 2013, 115.11: 1334-1346.
Mattheus et al., "Isolation of high-quality RNA from white spruce tissue using a three-stage purification method and subsequent cloning of a transcript from the PR-10 gene family," Phytochem Anal. Jul.-Aug. 2003;14(4):209-15.
Nguyen et al., "Camelina seed transcriptome: a tool for meal and oil improvement and translational research," Plant Biotechnol J. Aug. 2013;11(6):759-69. doi: 10.1111/pbi.12068. Epub Apr. 3, 2013.
Oo et al., "Lysophosphatidate acyltransferase activities in the microsomes from palm endosperm, maize scutellum, and rapeseed cotyledon of maturing seeds," Plant Physiol. Dec. 1989;91(4):1288-95.
Sandager et al., "Storage lipid synthesis is non-essential in yeast," J Biol Chem. Feb. 22, 2002;277(8):6478-82. Epub Dec. 10, 2001.
Sun et al., "Acyl coenzyme a preference of the glycerol phosphate pathway in the microsomes from the maturing seeds of palm, maize, and rapeseed," Plant Physiol. Sep. 1988;88(1):56-60.
Suzuki et al., "RNA isolation from siliques, dry seeds, and other tissues of *Arabidopsis thaliana*," Biotechniques. Oct. 2004;37(4):542, 544.
Wiberg et al., "The distribution of caprylate, caprate and laurate in lipids from developing and mature seeds of transgenic *Brassica napus* L," Planta. Dec. 2000;212(1):33-40.

\* cited by examiner

*Primary Examiner* — Medina A Ibrahim
*Assistant Examiner* — Wayne Zhong
(74) *Attorney, Agent, or Firm* — Fish & Richardson P.C.

(57) ABSTRACT

Provided herein are novel acyltransferases and methods of using such novel acyltransferases in making medium-chain fatty acids.

15 Claims, 32 Drawing Sheets

Specification includes a Sequence Listing.

ACYLTRANSFERASES AND METHODS OF USING

CROSS REFERENCE TO RELATED APPLICATIONS

This application claims the benefit of priority under 35 U.S.C. § 119(e) to U.S. Application No. 61/917,587 filed Dec. 18, 2013. The entirety of the prior application is incorporated by reference.

FEDERALLY SPONSORED RESEARCH OR DEVELOPMENT

This invention was made with government support under DE-SC0001295, 2009-05988, and IOS 0701919 awarded by the U.S. Department of Energy, the U.S. Department of Agriculture, and the National Science Foundation, respectively. The government has certain rights in the invention.

TECHNICAL FIELD

This disclosure generally relates to transgenic plants.

BACKGROUND

Plants in the genus, *Cuphea* (Lythracea), accumulate high levels of medium chain fatty acids (MCFAs) in their seeds. MCFAs are useful in the chemical industry in the production of detergents, lubricants and biofuels. *Camelina sativa* is a member of the Brassicaceae family, and has been found to be a sustainable source of oil for petroleum products. A high proportion of polyunsaturated fatty acids in *Camelina* oil, however, has limited its usefulness in the biofuel industry. Therefore, methods of engineering the oil properties in *Camelina* or other oil-producing organisms are desirable.

SUMMARY

In one aspect, a method of producing triacylglycerols (TAGs) comprising medium-chain fatty acids (MCFAs) in an organism is provided. Such a method typically includes introducing a transgene into the organism, wherein the transgene comprises at least one nucleic acid sequence encoding an acyltransferase, wherein the at least one acyltransferase exhibits a substrate specificity for saturated fatty acids, thereby producing TAGs comprising MCFAs in the organism.

In some embodiments, at least 20% (at least 40%, at least 50%, etc., etc.) of the TAGs comprising MCFAs have a C8:0 or a C10:0 at sn-2 position. In some embodiments, the saturated fatty acids are selected from the group consisting of C8:0 and C10:0.

In some embodiments, the at least one acyltransferase is a lysophosphatidic acid acyltransferase (LPAT) or a diacylglycerol acyltransferase (DGAT). In some embodiments, the at least one acyltransferase is a lysophosphatidic acid acyltransferase (LPAT) and a diacylglycerol acyltransferase (DGAT). In some embodiments, the nucleic acid sequence encoding the LPAT is selected from the group consisting of a sequence having at least 95% sequence identity to SEQ ID NO:1 and a sequence having at least 95% sequence identity to SEQ ID NO:3. In some embodiments, the nucleic acid sequence encoding the DGAT is selected from the group consisting of a sequence having at least 95% sequence identity to SEQ ID NO:7 and a sequence having at least 95% sequence identity to SEQ ID NO:9. In some embodiments, the nucleic acid sequence encoding the at least one acyltransferase is selected from the group consisting of a nucleic acid sequence having at least 95% sequence identity to SEQ ID NO:1, a nucleic acid sequence having at least 95% sequence identity to SEQ ID NO:3, a nucleic acid sequence having at least 95% sequence identity to SEQ ID NO:7, and a nucleic acid sequence having at least 95% sequence identity to SEQ ID NO:9.

In some embodiments, the organism further comprises a nucleic acid sequence encoding a medium-chain fatty acid (MCFA)-specific thioesterase FatB. In some embodiments, the nucleic acid sequence encoding the MCFA-specific thioesterase FatB is selected from the group consisting of a nucleic acid sequence having at least 95% sequence identity to SEQ ID NO:11, a nucleic acid sequence having at least 95% sequence identity to SEQ ID NO:13, and a nucleic acid sequence having at least 95% sequence identity to SEQ ID NO:15.

In some embodiments, the organism is selected from the group consisting of a plant and a microbe. In some embodiments, the plant is *Camelina sativa*.

In some embodiments, the transgene comprises a promoter. In some embodiments, the promoter is a seed-specific promoter. In some embodiments, the at least one nucleic acid sequence encoding an acyltransferase is operably linked to a seed-specific promoter. In some embodiments, the medium-chain fatty acids are produced in the seed.

In some embodiments, the introducing step is performed using *Agrobacterium* transformation, particle bombardment, or electroporation of protoplasts.

In another aspect, a method of producing triacylglycerols (TAGs) comprising medium-chain fatty acids (MCFAs) is provided. Such a method typically includes providing an organism comprising a transgene, wherein the transgene comprises at least one nucleic acid sequence encoding an acyltransferase, wherein the at least one acyltransferase exhibits a substrate specificity for saturated fatty acids; growing the organism under appropriate conditions; and obtaining TAGs comprising MCFAs from the organism. In some embodiments, the TAGs are used in biofuel, jet fuel, detergents, and chemical feedstocks.

In still another aspect, a method of increasing the amount of triacylglycerols (TAGs) comprising medium-chain fatty acids (MCFAs) in the seed oil of a plant is provided. Such a method typically includes providing a plant comprising a nucleic acid encoding a FatB polypeptide; introducing a heterologous nucleic acid molecule into the plant comprising at least one nucleic acid sequence encoding an acyltransferase, wherein the at least one acyltransferase exhibits a substrate specificity for saturated fatty acids, thereby increasing the amount of TAGs comprising MCFAs in the seed oil of the plant without significantly changing the total oil content in the seed.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

Part A

LPATs from *Cuphea pulcherrima* (black triangle) and 1 LPAT from *Cuphea viscosissima* (gray triangle) were aligned with putative orthologs of higher plants, which were obtained from the protein database of National Center for Biotechnology Information (NCBI). The phylogenic tree was built with the MEGA6 software, using the minimum-evolution method with 1000 number of bootstrap replication.

Figure 2:
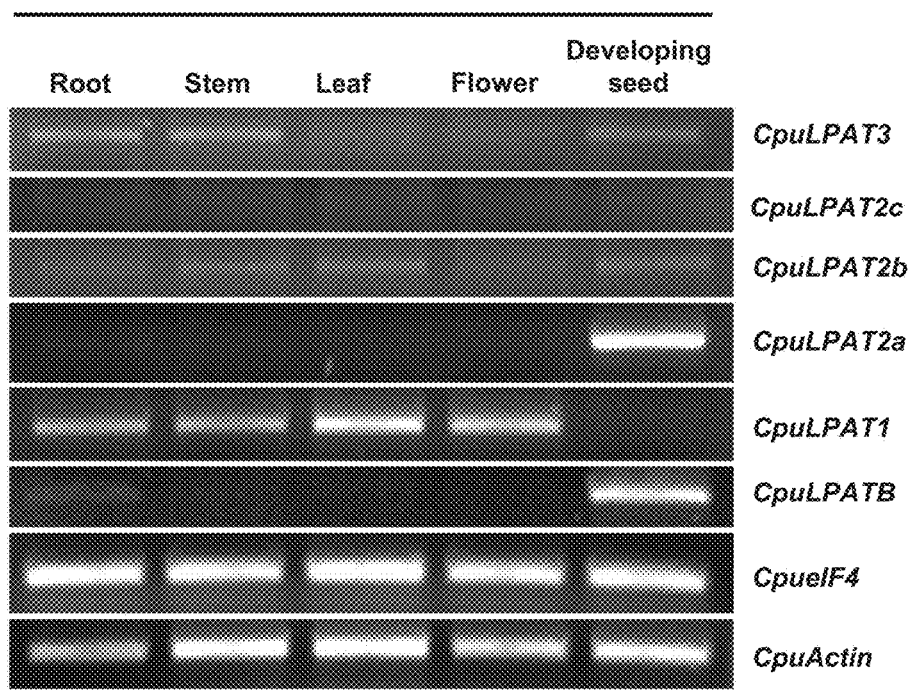
Figure 2:
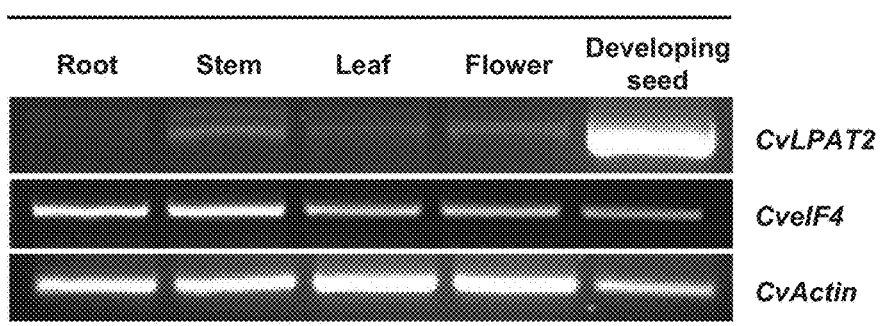

FIG. 2 are the results of RT-PCR analysis showing spatial expression of *Cuphea* LPAT genes in diverse tissues. The *Cuphea* eIF4 and actin were used as internal controls.

Figure 3:
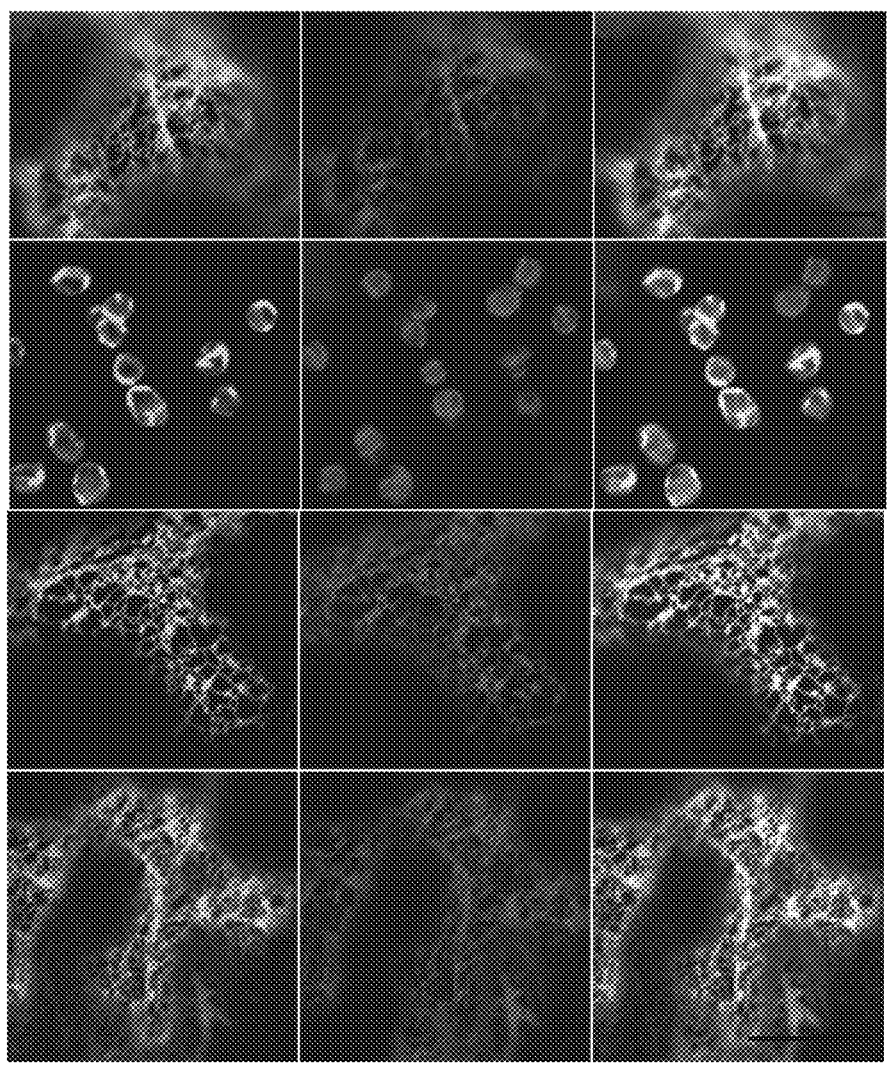

FIG. 3 are photographs showing the subcellular localization of *Cuphea* LPATs. Single plane image of tobacco epidermal cells was obtained from confocal laser scanning microscopy. Left panels are YFP signals of *Cuphea* LPATs, middle panels are ER markers (A, C and D) and auto fluorescence of chloroplasts (B), and right panels are merged images. Bars=10 μm. (A) CpuLPATB; (B) CpuLPAT1; (C) CpuLPAT2a; (D) CvLPAT2.

Figure 4:
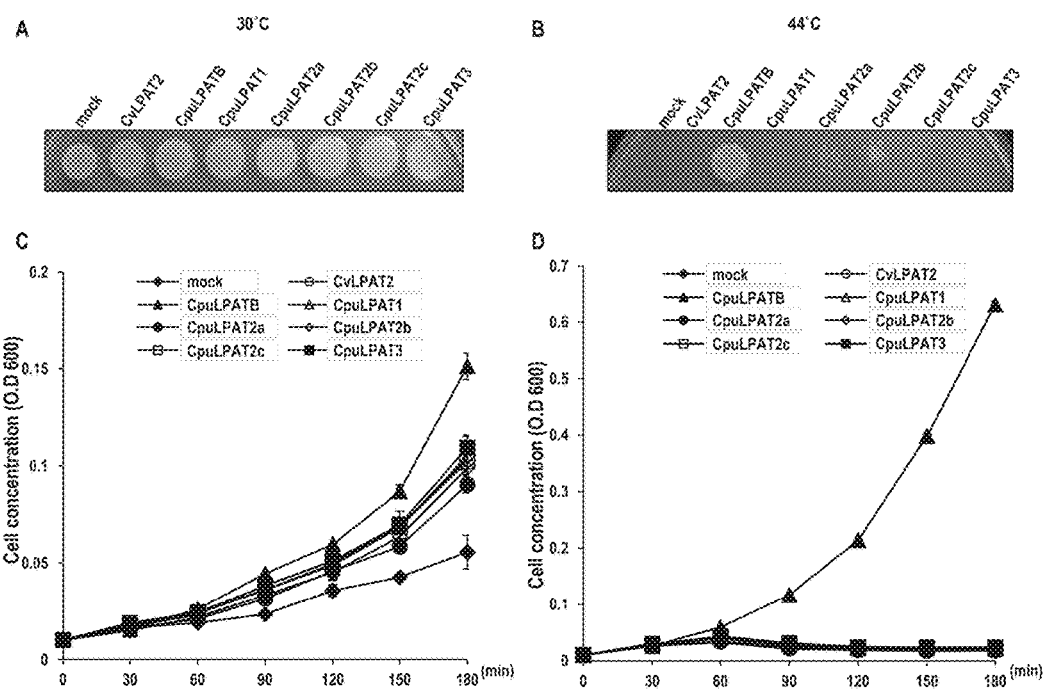

FIG. 4 is data showing the complementation test of *Cuphea* LPATs in mutated *E. coli*. The new *Cuphea* LPATs were transformed into the *E. coli* JC201 strain, a mutant strain that will not grow at non-permissive temperatures without a functional LPAT.

Figure 5A:
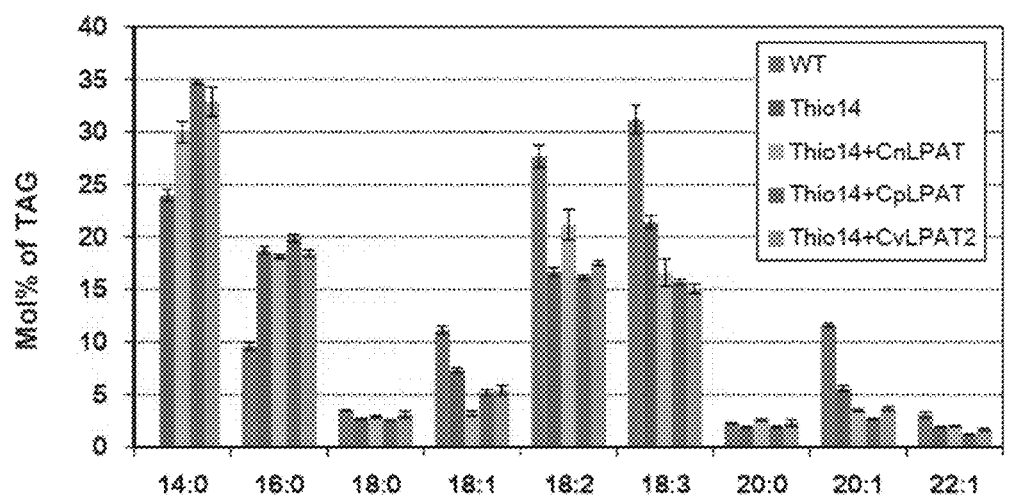

FIG. 5A is a graph showing the fatty acid composition of lipids (Mol % of TAG).

Figure 5B:
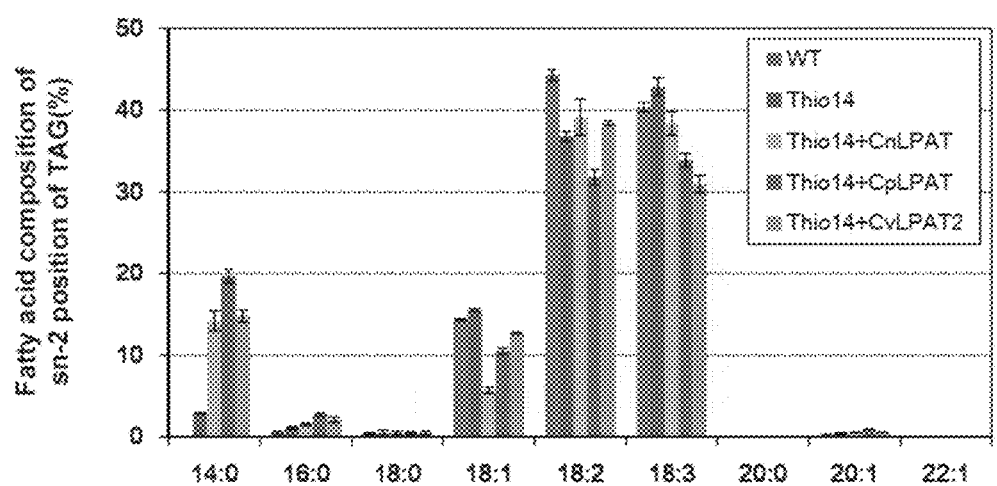

FIG. 5B is a graph showing the fatty acid composition of the sn-2 position of seed oil TAG.

Figure 5C:
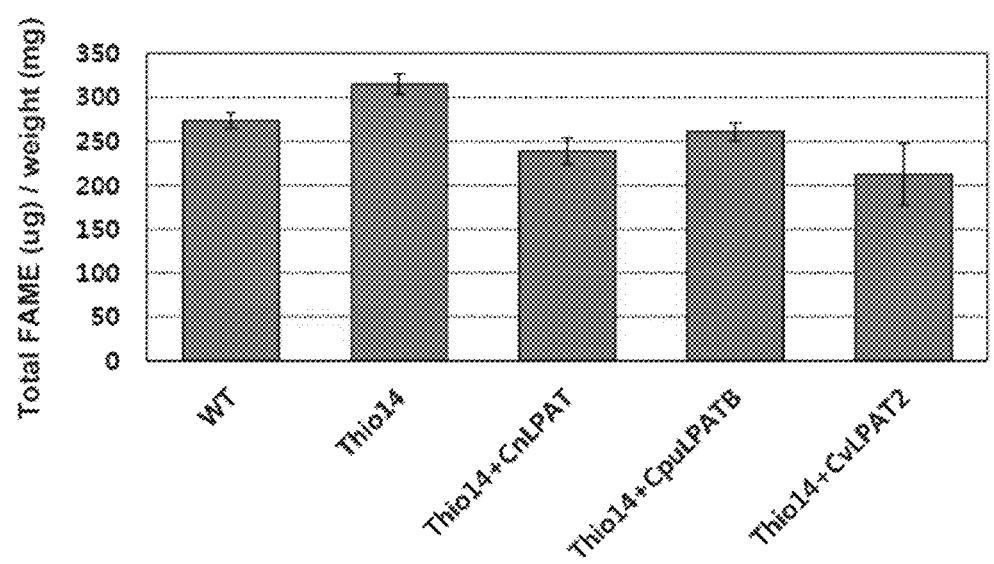

FIG. 5C is a graph showing the total amount of FAME (μg)/weight (mg).

Figure 5D:
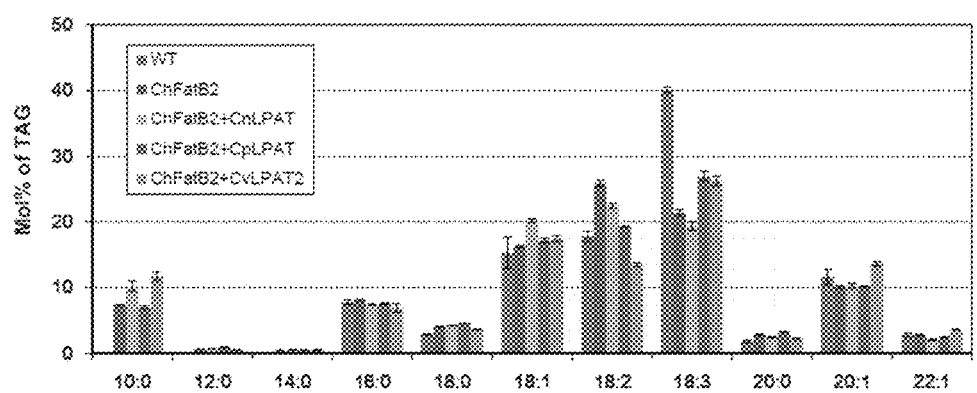

FIG. 5D is a graph showing the fatty acid composition of lipids (Mol % of TAG).

Figure 5E:
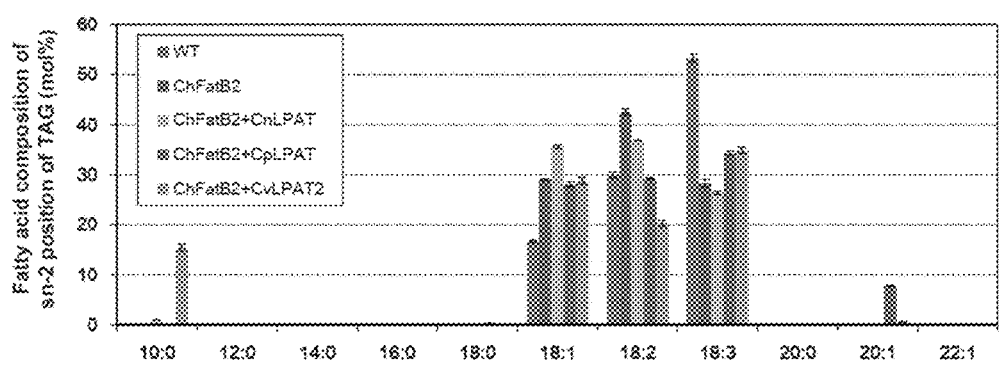

FIG. 5E is a graph showing the fatty acid composition of the sn-2 position of seed oil TAG.

Figure 5F:
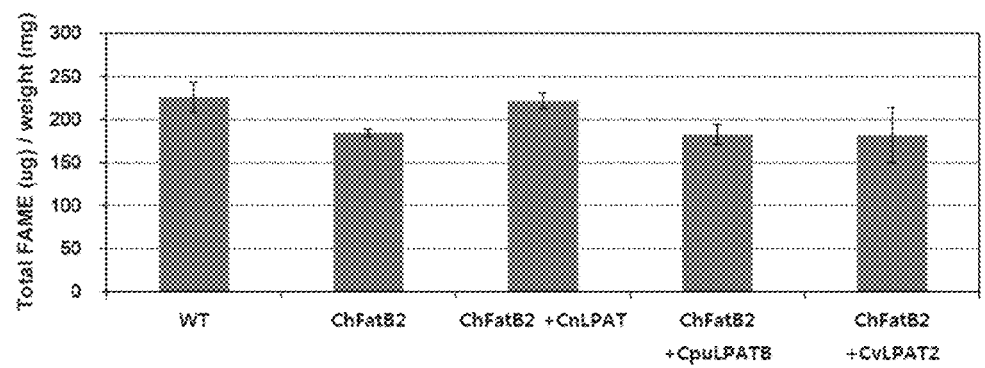

FIG. 5F is a graph showing the total amount of FAME (μg)/weight (mg).

Figure 6:
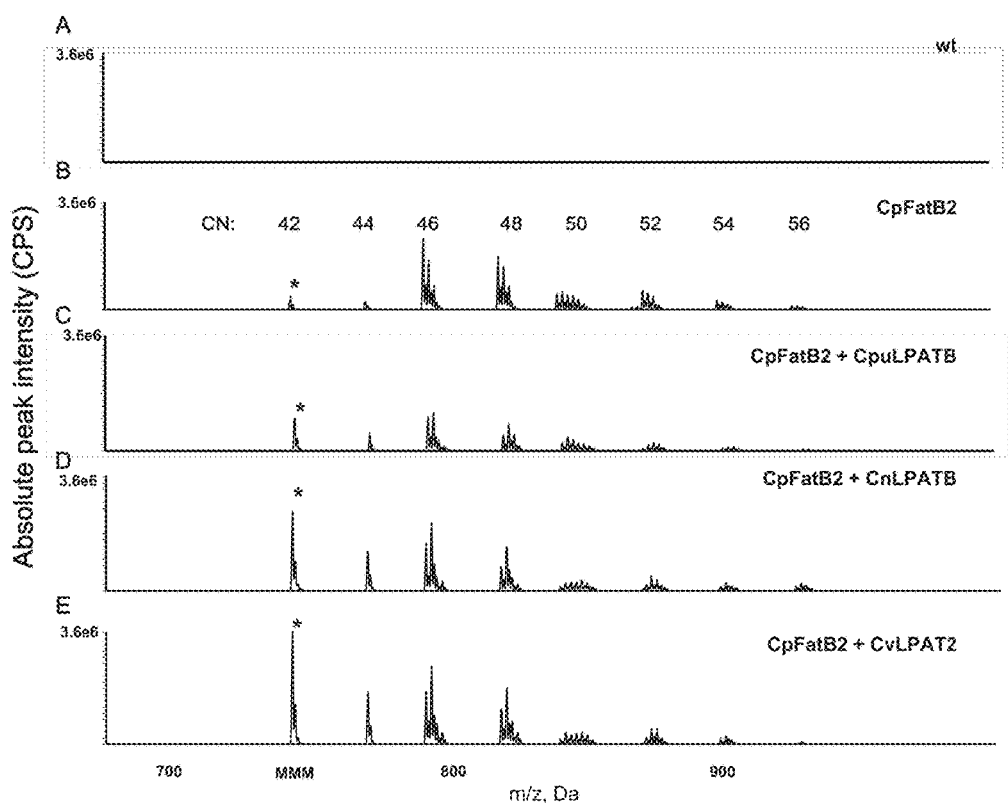

FIG. 6 shows data demonstrating C14:0-containing TAG species detected by Neutral Loss ESI-MS/MS. Electrospray mass spectroscopy of TAG isolated from wild type (A) and 14:0 specific CpFatB2 (B) with CpuLPATB (C), CnLPATB (D), and CvLPAT2 (E). CN indicates the carbon number of TAG.

Figure 7:
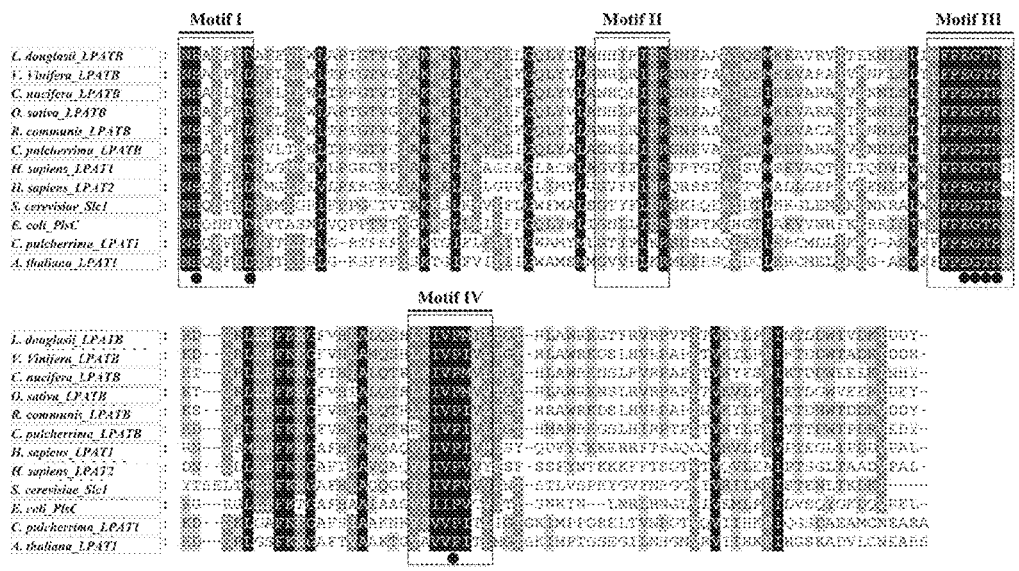
Figure 7:
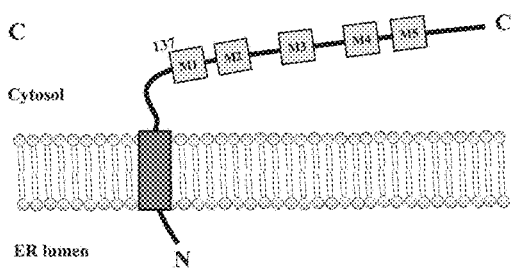

FIG. 7 provides the amino acid alignment of CpuLPATB homologs and information regarding the predicted transmembrane segments. (A) Amino acid alignment of SEQ ID NOs:17-28 (top to bottom) using the CLUSTAWL algorithm was generated using LPLAT-AGPAT-like domains of LPATB and LPAT1 homologs. Gray-dotted boxes indicate acyltransferase motifs. Circles and black triangles are catalytic amino acids and binding site in acyltransferase motifs, respectively. (B) Predicted transmembrane region of CpuLPATB by different programs; SOSUI, PSORTII, HMMTOP, and TMHMM server 2.0. The numbers indicate the amino acid residue of CpuLPATB. (C) A schematic showing topological transmembrane and acyltransferse motifs of CpuLPATB.

Figure 8:
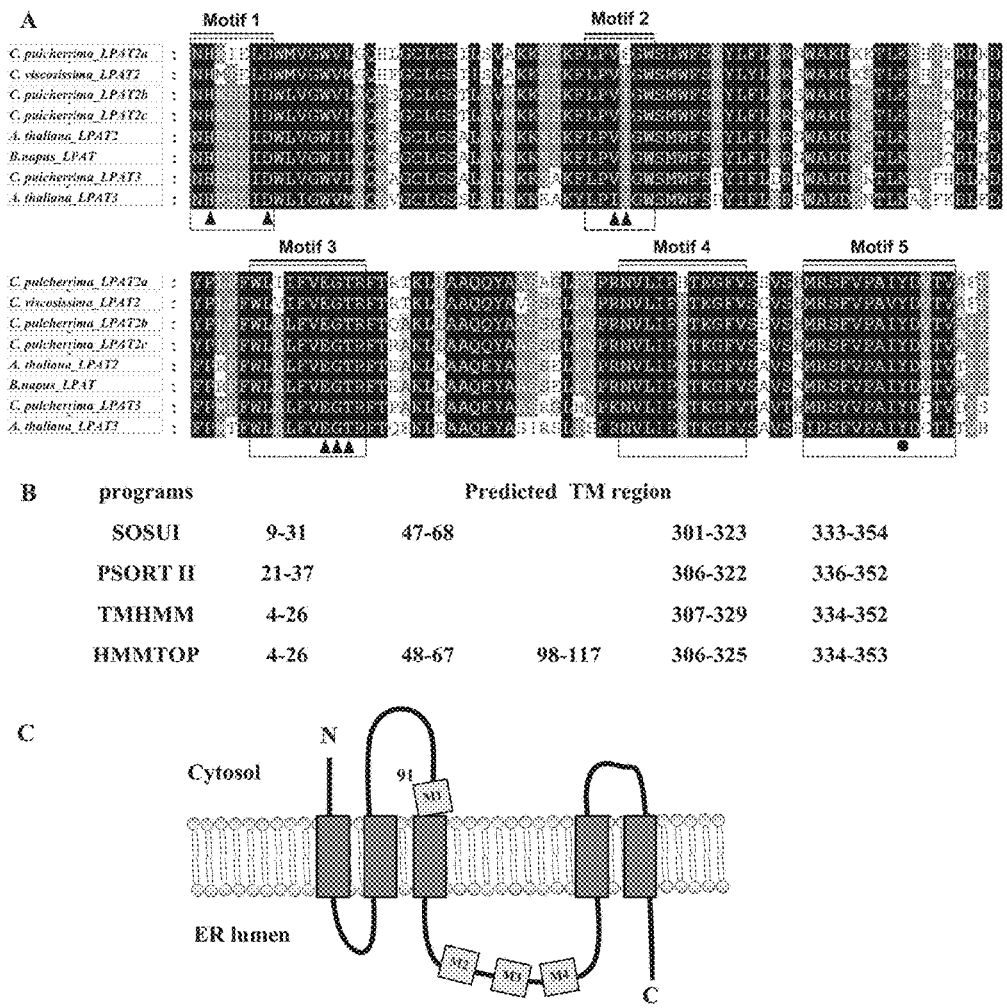

FIG. 8 provides the amino acid alignment of CvLPAT2 homologs and information regarding the predicted transmembrane segments. (A) Amino acid alignment of SEQ ID NOs: 29-36 (top to bottom) using the CLUSTAWL algorithm was generated using LPLAT-AGPAT-like domains of LPAT2 and LPAT3 homologs. Gray-dotted boxes indicate acyltransferase motifs. Circles and black triangles are catalytic amino acids and binding site in acyltransferase motifs, respectively. (B) Predicted transmembrane region of CvLPAT2 by different programs; SOSUI, PSORTII, HMMTOP, and TMHMM server 2.0. The numbers are indicated the amino acid residue of CpuLPATB. (C) A schematic showing the topological transmembrane and acyltransferase motifs of CvLPAT2.

Figure 9:
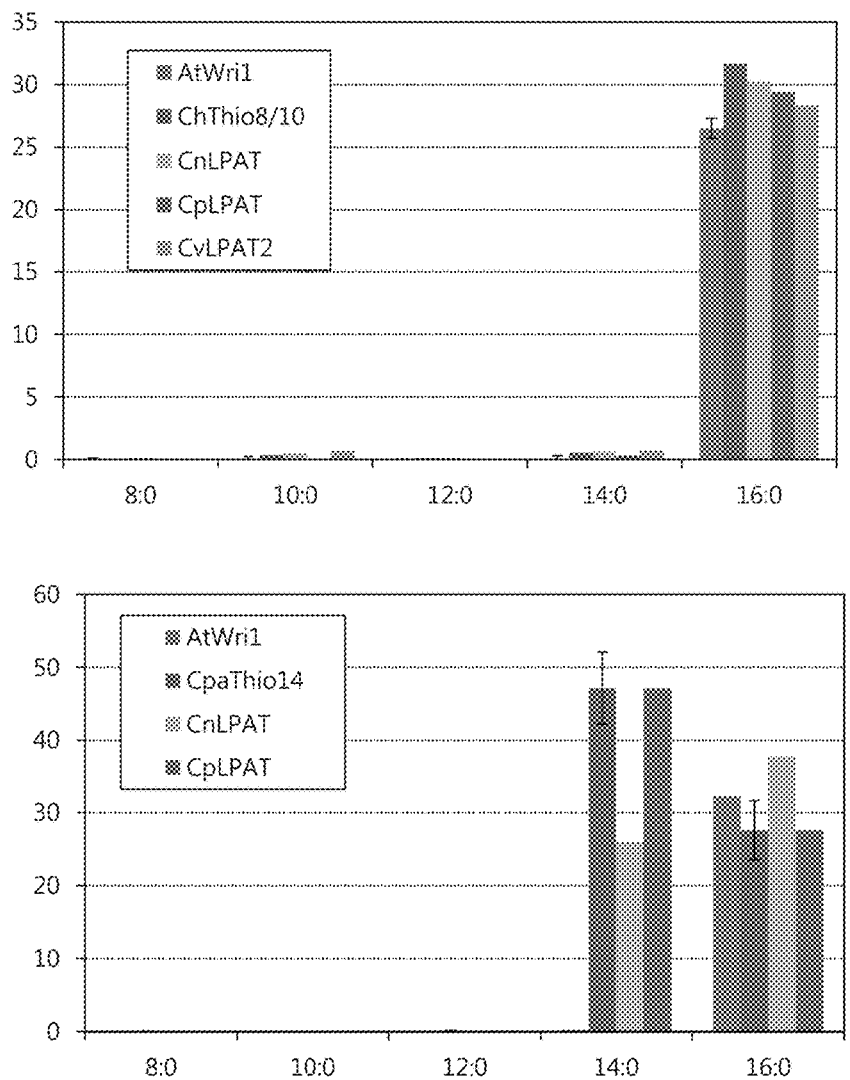

FIG. 9 are graphs showing LPAT activity expressed in Agro-infiltrated tobacco leaf.

Figure 10:
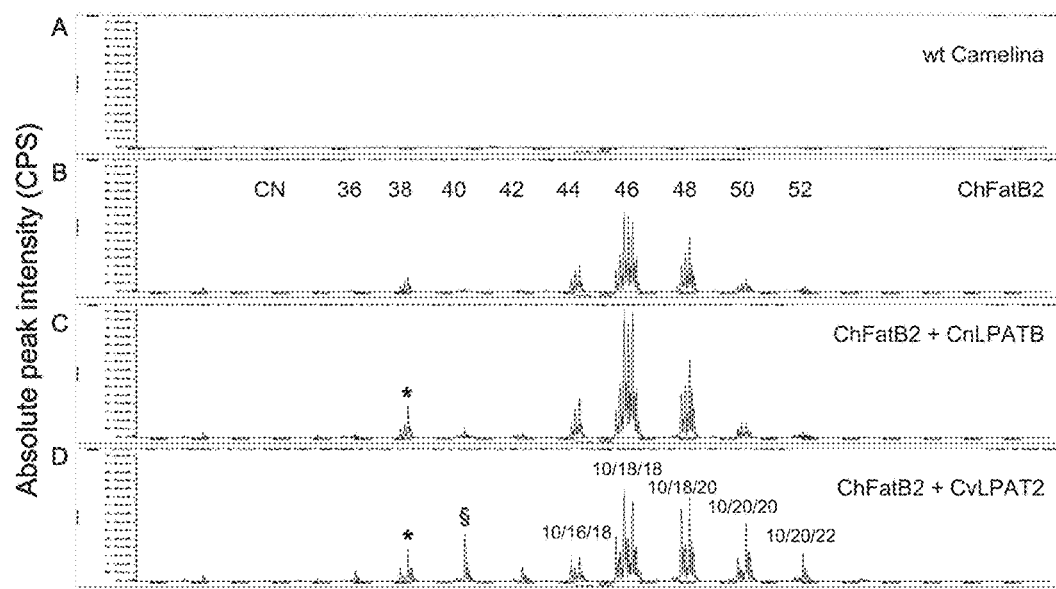

FIG. 10 is data showing the C10:0-containing TAG species detected by Neutral Loss ESI-MS/MS. Electrospray mass spectroscopy of TAG isolated from wild type (A) and 14:0 specific ChFatB2 (B) with CnLPATB (C) and CvLPAT2 (D). CN indicates the carbon number of TAG. *: contains 10/10/18:1, §: contains 10/10/20:1.

Part B

Figure 11:
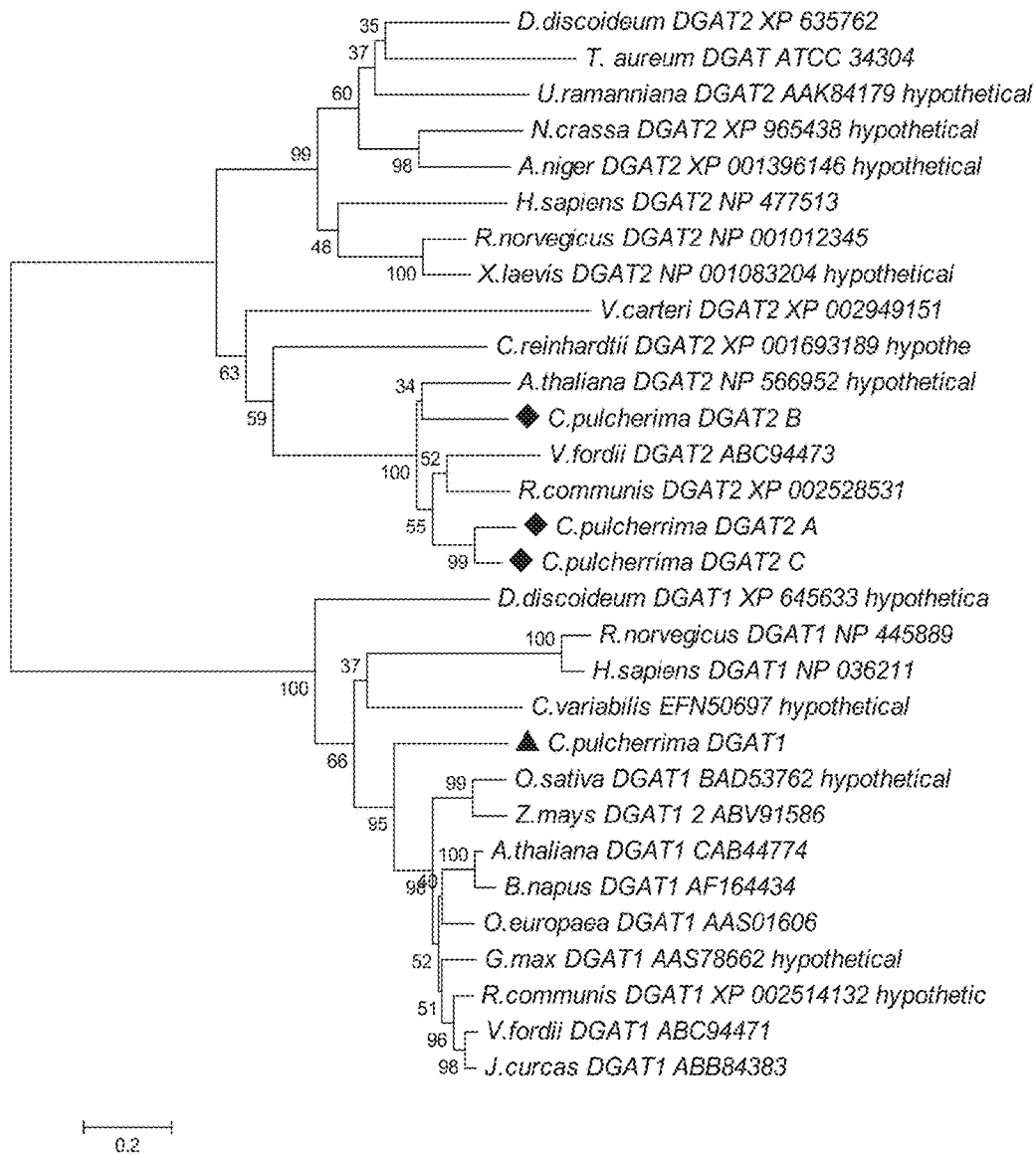

FIG. 11 is an unrooted phylogram of *C. pulcherrima* DGAT1 (CpDGAT1) and other hypothetical and functionally characterized DGATs. The alignment was generated by the CLUSTAL W program and the unrooted phylogram was constructed by the neighbor-joining method in MEGA4 software (Tamura et al., 2007, Mol. Biol. Evol., 24:1596-9).

Figure 12:
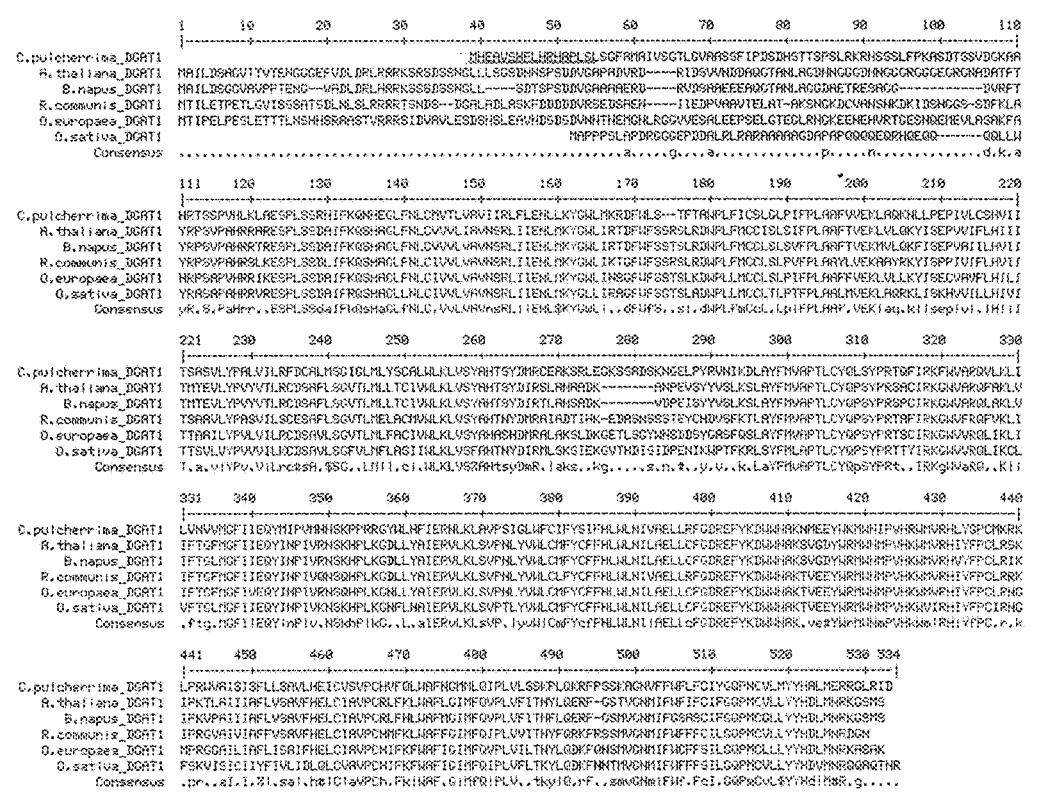

FIG. 12 is an alignment of deduced amino acid sequence of CpDGAT1 with some of its orthologs (SEQ ID NOs: 37-42, top to bottom).

Figure 13:
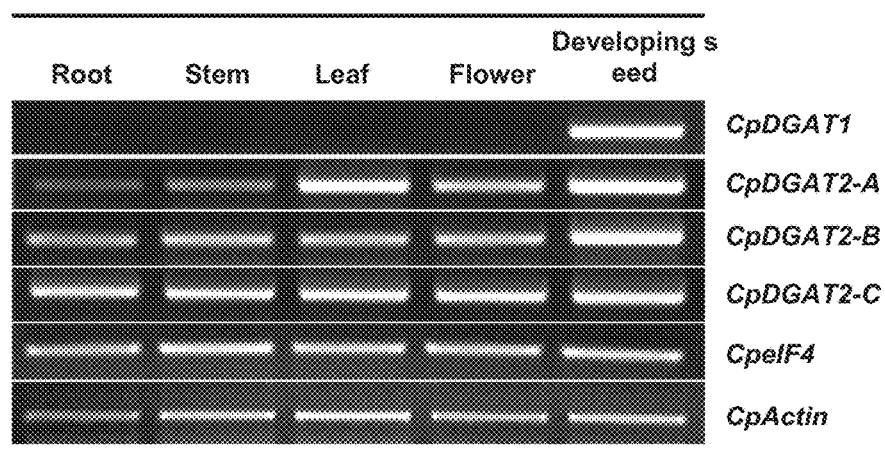

FIG. 13 is data showing CpDGAT1, CpDGAT2_A, CpDGAT2_B and CpDGAT2_C expression analysis in *C. pulcherrima* tissues by SQRT-PCR of cDNA from total RNA. PCR products were obtained with gene specific primers for CpDGAT1, CpDGAT2_A, CpDGAT2_B or CpDGAT2_C.

Figure 14:
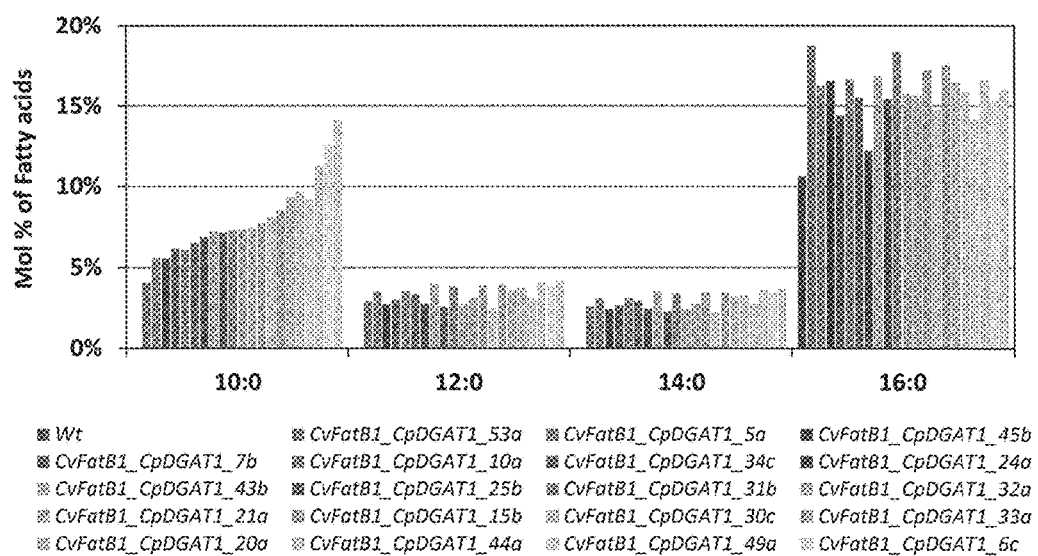

FIG. 14 is a graph showing the short and medium chain fatty acid profile of CvFATb1+CpDGAT1 (T2) lines.

Figure 15:
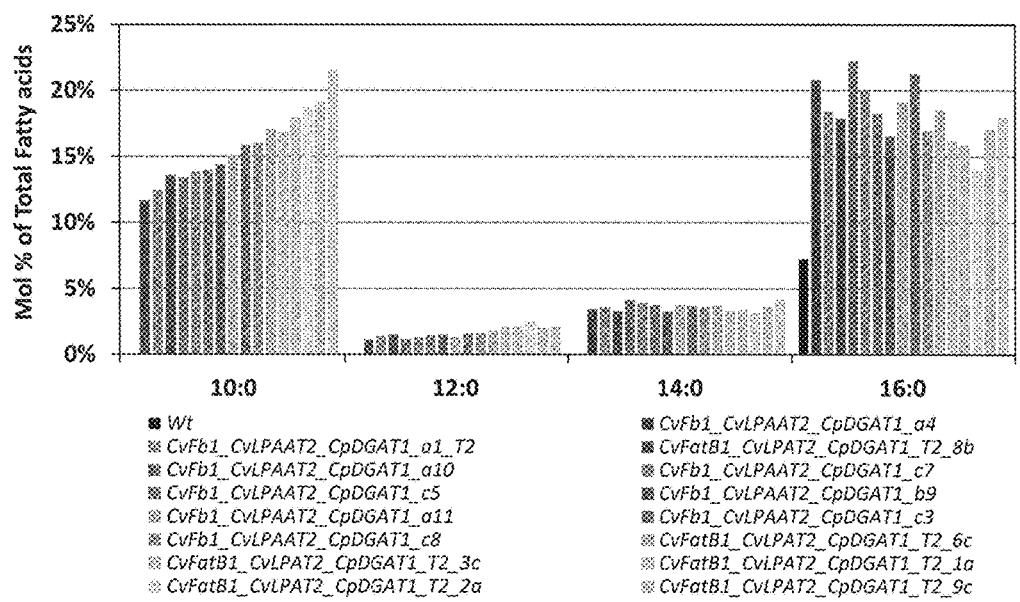

FIG. 15 is a graph showing the short and medium chain fatty acid profile in CvFatB1+CvLPAT2+CpDGAT1 (T2) lines.

Figure 16:
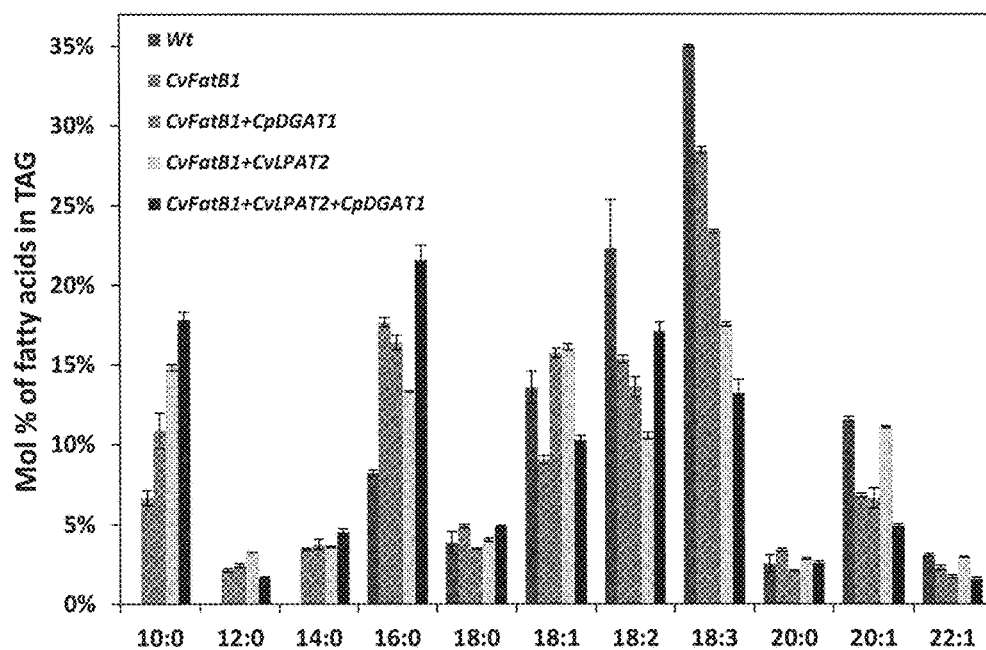
Figure 17:
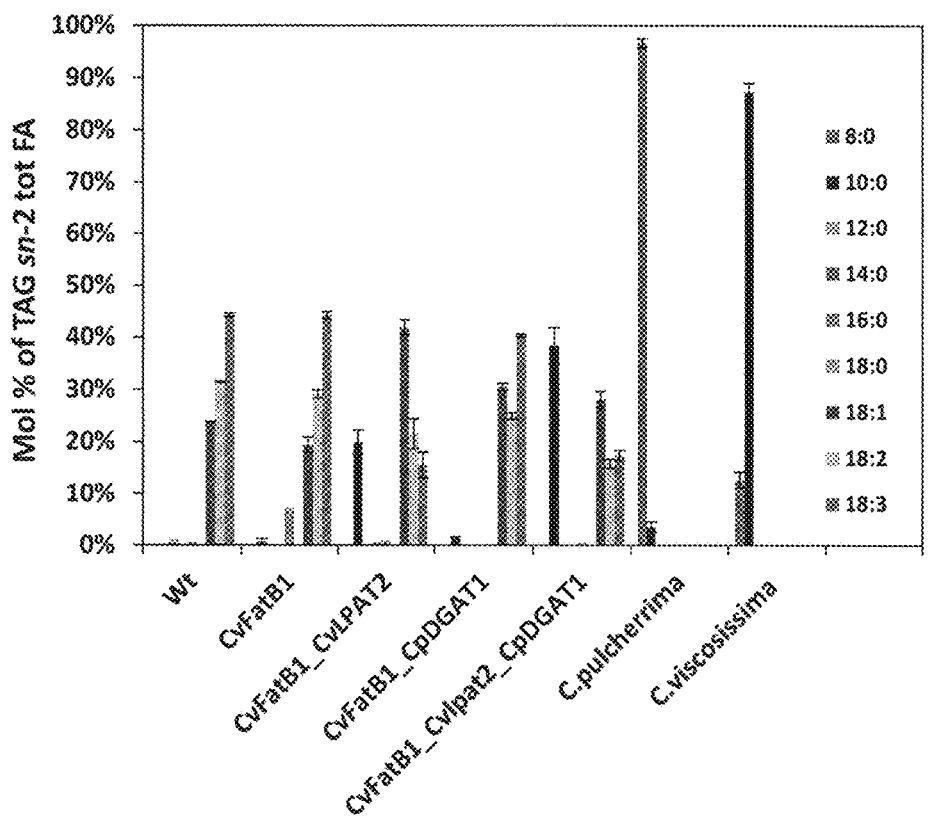

FIG. 16 is a graph showing the fatty acid profile of TAG from transgenic *Camelina* plants FIG. 17 is a graph showing the fatty acid profile of MAG species separated following the digestion of TAG from mature seeds of wild type and transgenic *Camelina* CvFatB1, CvFatB1+CvLPAT2, CvFatB1+CpDGAT1, CvFatB1+CvLPAT2+CpDGAT1 lines and *C. pulcherrima* and *C. viscosissima*.

Figure 18A:
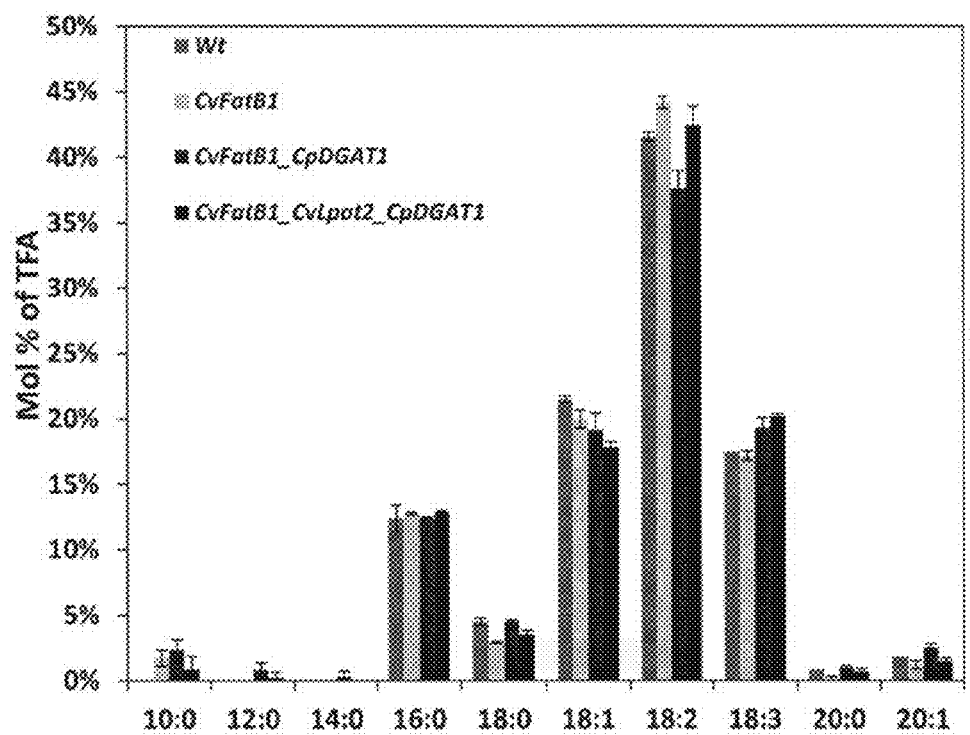

FIG. 18A is a graph showing the fatty acid profile in developing seeds from wild type and transgenic *Camelina* lines expressing CvFatB1, CvFatB1+CpDGAT1, or CvFatB1+CvLPAT2+CpDGAT1 at 10 DAF (days after flowering). At ten DAF, developing seeds contain very low amounts of 10:0 (~2.5 mol %); the main fatty acids were 16:0 (~14 mol %), 18:1 (20 mol %), 18:2 (40-44 mol %), and 18:3 (18-20 mol %). The percent share of each fatty acid (16:0 through 20:1) in TFA in transgenic lines was similar to that of wild type *Camelina* plants.

Figure 18B:
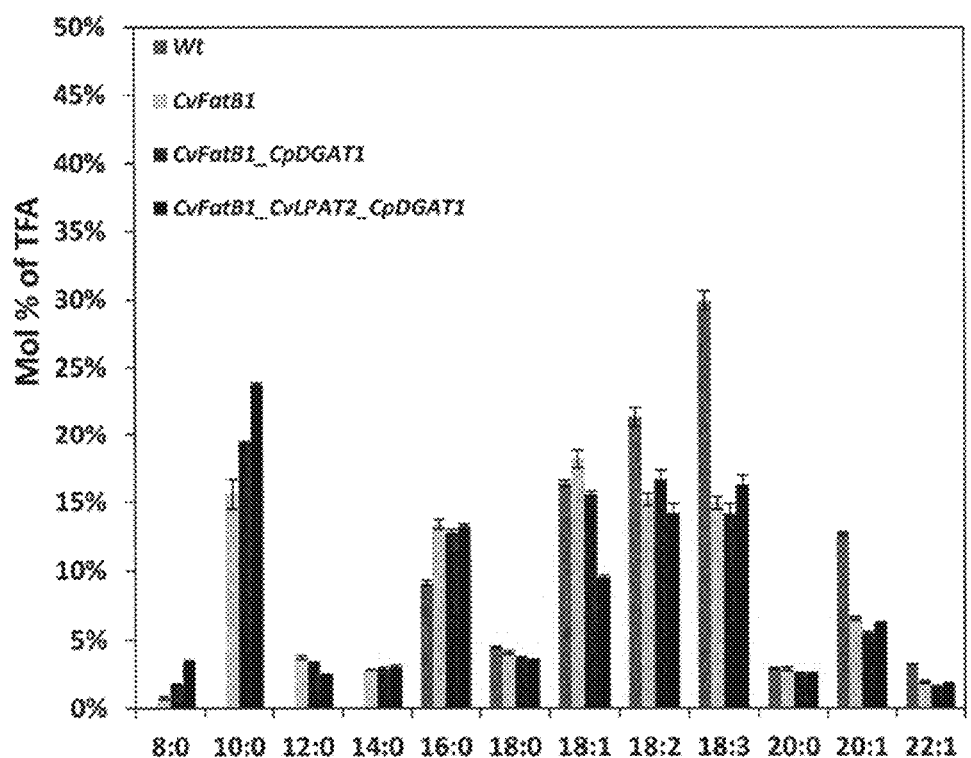

FIG. 18B is a graph showing the fatty acid profile in developing seeds from wild type and transgenic *Camelina* lines expressing CvFatB1, CvFatB1+CpDGAT1, or CvFatB1+CvLPAT2+CpDGAT1 at 17 DAF. 17 DAF seeds contain more medium-chain fatty acids (8:0 (4 mol %), 10:0 (up to 24 mol %), 12:0 (2.5-4 mol %), 14:0 (3 mol %)) and higher amounts of 16:0 (13 mol %) in transgenic lines. In CvFatB1+CvLpat2+CpDGAT1, the amount of 18:1 decreases, while 18:2, 18:3 and 20:1 are present in amounts of 15 mol %, 16 mol % and 6 mol %, respectively, as compared to 21.4 mol %, 30 mol % and 12.7 mol % in wild type *Camelina* plants.

Figure 18C:
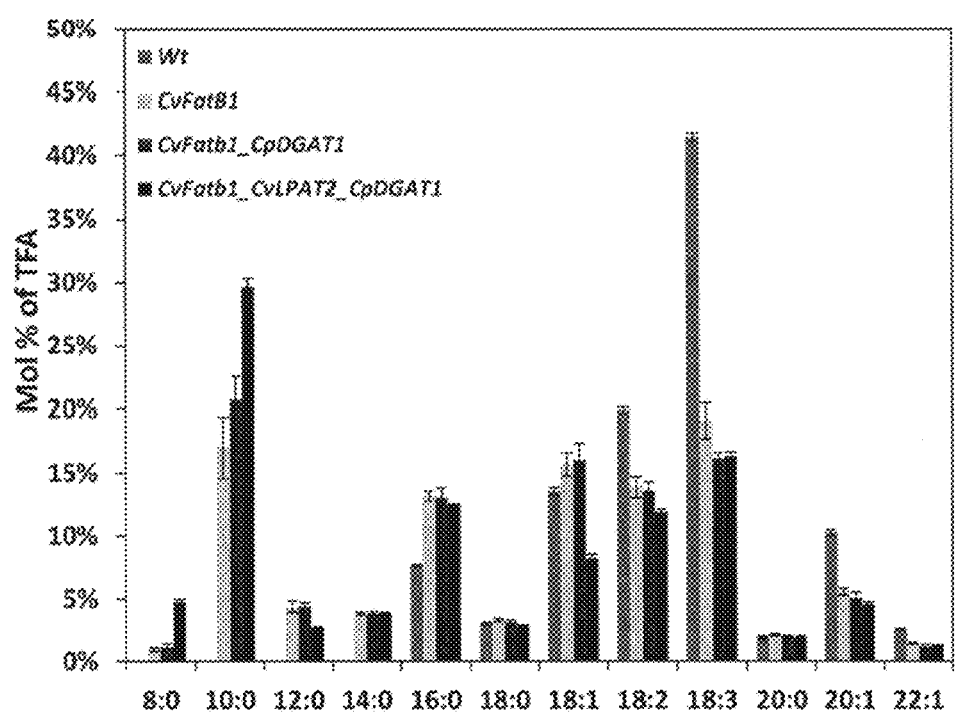

FIG. 18C is a graph showing the fatty acid profile in developing seeds from wild type and transgenic *Camelina* lines expressing CvFatB1, CvFatB1+CpDGAT1, or CvFatB1+CvLPAT2+CpDGAT1 at 22 DAF. 22 DAF seeds produce more medium chain fatty acids (5 mol % 8:0, 30 mol % 10:0, 7 mol % (12:0-14:0)). The amounts of 16:0, 18:0, 18:1, 18:2, 18:3 and 20:1 in CvFatB1+CvLPAT2+ CpDGAT1 line are 12 mol %, 8 mol %, 12 mol %, 16 mol %, and 5 mol % as compared to 8 mol %, 13 mol %, 20 mol %, 41 mol %, and 10 mol % in seeds of wild type plants. Thus, the total share of 8:0 to 16:0 fatty acids in this line reaches 54 mol % of TFA as compared to 39 mol % in CvFatB1 line, 43% in CvFatB1+CpDGAT1 line and just 8 mol % in wild type.

Figure 18D:
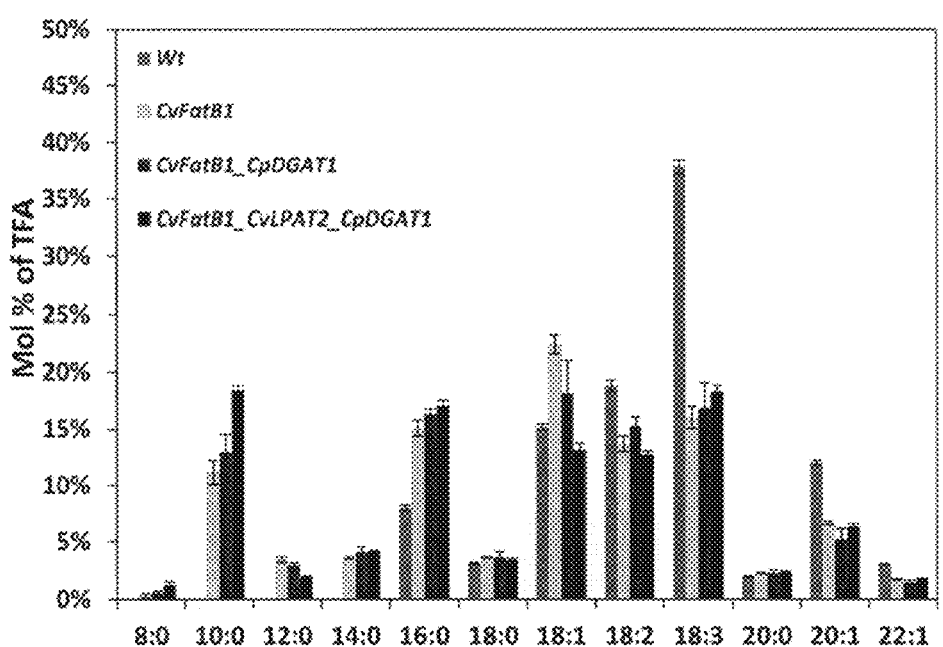

FIG. 18D is a graph showing the fatty acid profile in developing seeds from wild type and transgenic Camelina lines expressing CvFatB1, CvFatB1+CpDGAT1, or CvFatB1+CvLPAT2+CpDGAT1 at 30 DAF. In 30 DAF seeds from CvFatB1 line, there is 33.6 mol % of 8:0-16:0, 22.4 mol % 18:1, 13.7 mol % 18:2, 16.0 mol % 18:3 and 6.6 mol % 20:1. CvFatB1+CpDGAT1 transgenic lines accumulate more 10:0, and 8:0-16:0 total fatty acid amount is 37 mol % while amounts of 18:1, 18:2, 18:3 and 20:1 are similar to what is found in seeds from CvFatB1 line. In CvFatB1+CvLPAT2+CpDGAT1 lines, the average share of 8:0-16:0 fatty acids is 43 mol % of TFA, 18.5 mol % being 10:0 and 13.2 mol % 18:1, 12.8 mol % 18:2, 18.3 mol % 18:3, 6.3 mol % 20:1.

Figure 19:
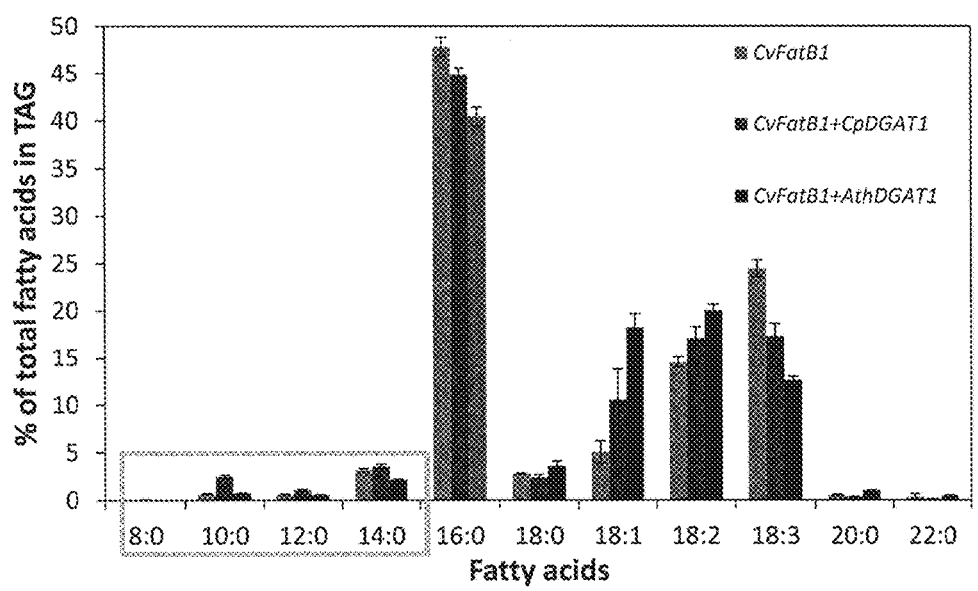

FIG. 19 is a graph showing fatty acid profile of TAG from N. benthamiana leaves infiltrated with CvFatB1, CvFatB1+ CpDGAT1, CvFatB1+AthDGAT1.

Figure 20:
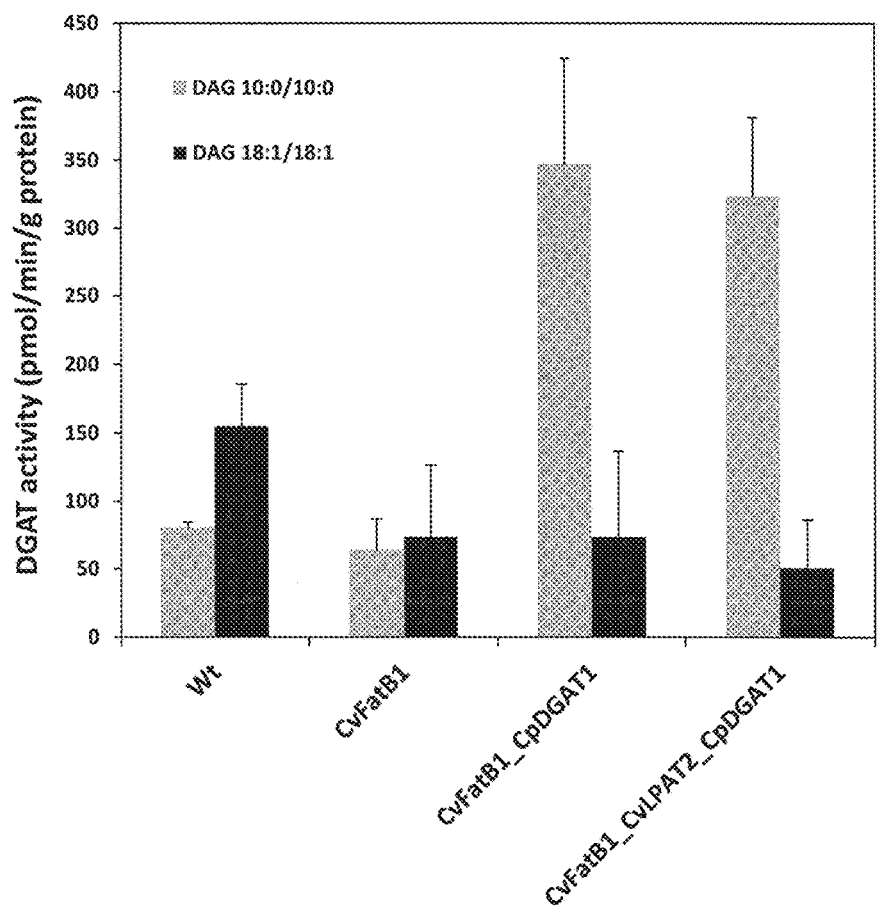

FIG. 20 is a graph showing DGAT activity in crude extracts of developing seeds from Wt and transgenic Camelina lines. Values are mean±SD (n=3). Results are for assays using [1-14C] 10:0-CoA, and diacylglycerol (DAG) species: 10:0/10:0 (1,2-didecanoyl-sn-glycerol) or 18:1/18:1 (1,2-dioleoyl-sn-glycerol).

Figure 21:
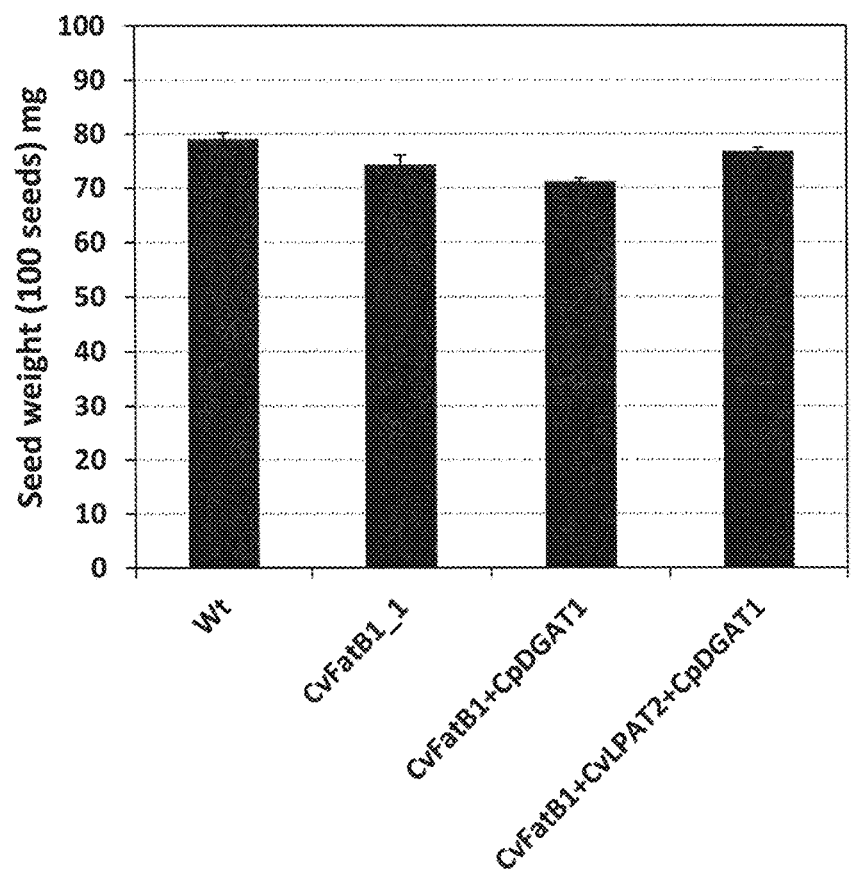

FIG. 21 is a graph showing the seed weight of mature seeds from Wt and transgenic Camelina.

Figure 22:
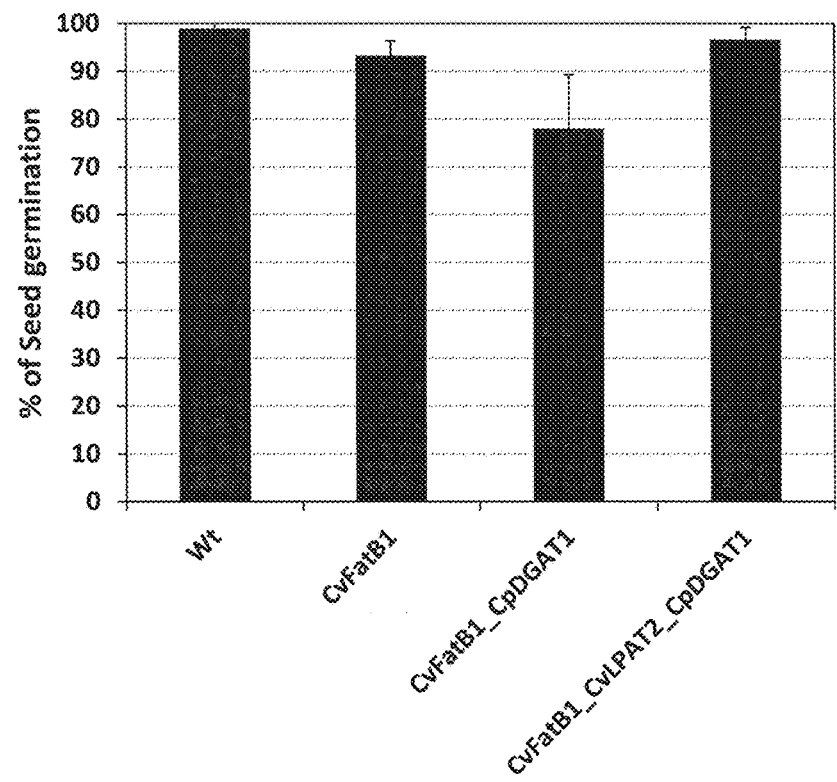

FIG. 22 is a graph showing the germination efficiency of transgenic Camelina seeds.

Figure 23:
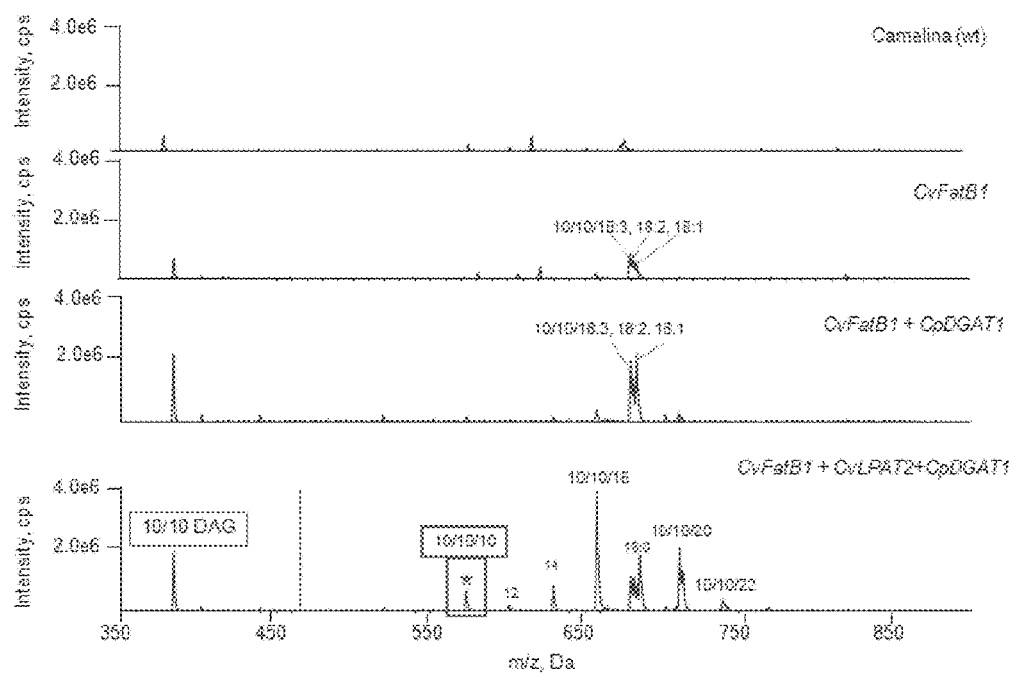

FIG. 23 is data showing 10:0/10:0 DAG containing TAG species detected by Precursor 383.3 m/z ESI-MS/MS scans.

Figure 24:
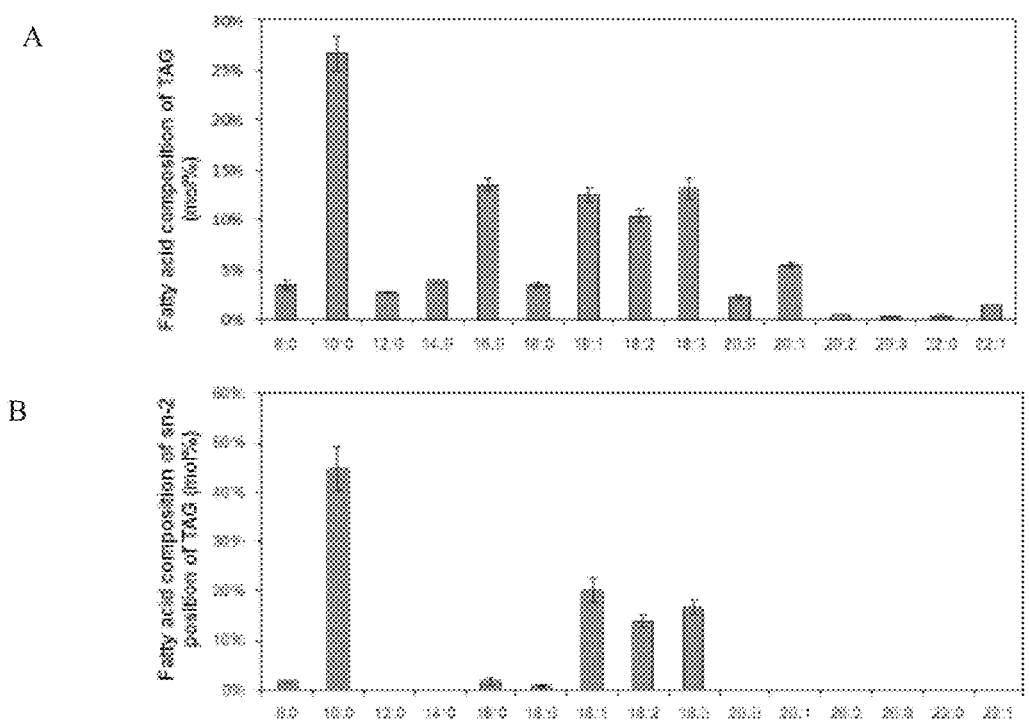

FIG. 24 are graphs showing fatty acid profiles of a Camelina transgenic line.

DETAILED DESCRIPTION

This disclosure is based on the discovery of novel nucleic acids encoding acyltransferase polypeptides. Such nucleic acids, SEQ ID NOs: 1, 3, 5, 7, or 9, and the polypeptides encoded thereby, SEQ ID NOs: 2, 4, 6, 8, or 10, are described and characterized herein. Based on this discovery, such nucleic acid sequences can be used to produce particular and unique medium-chain fatty acids (MCFAs).

As described herein, lysophosphatidic acid acyltransferase (LPAT) and diacylglycerol acyltransferase (DGAT) catalyze sequential reactions in the Kennedy pathway that produce triacylglycerols (TAG) in seeds and other plant tissues and organs. Triacylglycerols are the principal component of vegetable oils, which are used in a variety of edible applications (e.g., baking, frying) as well as non-food applications, such as biofuels, lubricants, and surfactants. LPAT uses fatty acids in the form of fatty acyl-Coenzyme A (CoA) as substrates for esterification to the sn-2 position of lysophosphatidic acid (LPA) to form phosphatidic acid (PA). Following dephosphorylation of PA, the resulting diacylglycerol (DAG) serves as a substrate for addition of a fatty acid in the form of fatty acyl-CoA to its sn-3 position to generate triacylglycerol, via the activity of DGAT. LPAT activity in seeds of the typical oilseed crops, such as canola (Brassica napus), camelina (Camelina sativa), and soybean (Glycine max) have strong specificity for unsaturated C18 fatty acid acyl-CoA substrates such as oleoyl (18:1)-, linoleoyl (18:2)-, and linolenoyl (18:3)-CoA, but little or no activity with saturated fatty acyl-CoA substrates (Sun et al., 1988, Plant Physiol., 88, 56-60; Oo et al., 1989, Plant Physiol., 91, 1288-1295). This activity arises predominantly from LPATs of the LPAT2 class, but also with contributions from LPATs of the bacterial-type LPATB class [Arroyo-Caro, J. M., Chileh, T., Kazachkov, M., Zou, J., Alonso, D. L., Garcia-Maroto, F. (2013) Plant Sci. 199-200:29-40]. The strict substrate specificity of oilseed LPATs for unsaturated fatty acyl-CoA substrates represents a major bottleneck for metabolic engineering of oilseeds to produce TAG with high levels of saturated medium-chain fatty acids with C6-C14 chain-lengths for applications such as biofuels, including bio-based Jet fuel A. These metabolic engineering strategies typically involve expression of divergent forms of the FatB acyl-ACP thioesterase that are able to produce medium-chain fatty acids of differing chain-lengths. An LPAT from coconut of the LPATB class has been previously shown to be effective at esterifying lauroyl (12:0)-CoA to the sn-2 position of LPA to produce lauric acid-rich oils when co-expressed with a 12:0-acyl carrier protein-specific FatB. The coconut LPATB enzyme, however, was ineffective for esterification of CoA forms of caprylic (8:0) or decanoic (10:0) acids to the LPA sn-2 position to generate 10:0-rich TAG in an engineered oilseed (Wiberg et al., 2000, Planta, 212, 33-40). In addition, no plant LPAT2 enzymes have been previously shown to have significant activity with any saturated medium-chain fatty acids.

DGAT enzymes occur in two forms, DGAT1 and DGAT2, based on their primary structures. These enzymes also represent potential bottlenecks for the accumulation of high levels of saturated medium-chain fatty acids in TAG of engineered oilseeds. DGAT2 enzymes from plants such as castor bean have been shown to enhance the accumulation of modified fatty acids such as ricinoleic acid. However, no specific plant DGAT1 or DGAT2 has been previously been shown to be effective at promoting increased accumulation of saturated medium-chain fatty acids in engineered oilseeds or to be active with DAGs rich in medium-chain fatty acids such as decanoic acid (10:0).

The embodiment of this invention is the discovery of LPAT2 and DGAT1 genes that are demonstrated in this disclosure to enhance the accumulation of medium-chain fatty acids, in particular, C8:0 and C10:0, in TAG and in the sn-2 position of TAG when expressed together with specialized FatB genes in seeds of the oilseed crop camelina (Camelina sativa). The co-expression of the LPAT2 genes with the DGAT1 genes is also shown to yield synergistic increases in medium-chain fatty acid accumulation in TAG and the sn-2 position of TAG in transgenic plants.

Nucleic Acids and Polypeptides

Novel nucleic acids encoding acyltransferases are provided herein (see, for example, SEQ ID NOs: 1, 3, 5, 7, or 9). Acyltransferases (PF01553; EC 2.3.1) are well known in the art and are defined as transferase enzymes that act on acyl groups. The acyltransferases exemplified herein include a lysophosphatidic acid acyltransferase (LPAT; EC 2.3.1.51) and a diacylglycerol acyltransferase (DGAT; EC 2.3.1.20). The LPAT2 and LPAT2a polypeptides disclosed herein are unique in that they esterify saturated C8-C16 fatty acyl-CoA, including a high affinity for saturated C8 and C10 fatty acyl-CoA, at the sn-2 position of triacylglycerols (TAGs), while the DGAT1 polypeptides disclosed herein have unique specificity for diacylglycerols (DAGs) substrates having a saturated C10 and, to a lesser extent, a saturated C8, at the sn-2 position.

Novel nucleic acids encoding medium-chain fatty acid (MCFA)-specific thioesterase, FatB polypeptides also are provided herein (see, for example, SEQ ID NO: 15). FatB polypeptides are a class of thioesterases (EC 3.2.1.14) that release C8 to C16 saturated fatty acids from acyl carrier protein (ACP) during de novo fatty acid synthesis. The typical FatB releases C16:0 from ACP, but FatBs that release other saturated fatty acids are known.

As used herein, nucleic acids can include DNA and RNA, and includes nucleic acids that contain one or more nucleotide analogs or backbone modifications. A nucleic acid can be single stranded or double stranded, which usually depends upon its intended use. The novel nucleic acids provided herein encode novel polypeptides (see, for example, SEQ ID NOs: 2, 4, 6, 8, 10, or 16). Also provided are nucleic acids and polypeptides that differ from SEQ ID NOs: 1, 3, 5, 7, 9, or 15, and SEQ ID NOs: 2, 4, 6, 8, 10, or 16, respectively. Nucleic acids and polypeptides that differ in sequence from SEQ ID NOs: 1, 3, 5, 7, 9, or 15, and SEQ ID NOs: 2, 4, 6, 8, 10, or 16, can have at least 50% sequence identity (e.g., at least 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity) to SEQ ID NOs: 1, 3, 5, 7, 9, or 15, and SEQ ID NOs: 2, 4, 6, 8, 10, or 16, respectively.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the computer program ClustalW and default parameters, which allows alignments of nucleic acid or polypeptide sequences to be carried out across their entire length (global alignment). Chenna et al., 2003, Nucleic Acids Res., 31(13): 3497-500. ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

Changes can be introduced into a nucleic acid molecule (e.g., SEQ ID NOs: 1, 3, 5, 7, 9, or 15), thereby leading to changes in the amino acid sequence of the encoded polypeptide (e.g., SEQ ID NOs: 2, 4, 6, 8, 10, or 16). For example, changes can be introduced into nucleic acid coding sequences using mutagenesis (e.g., site-directed mutagenesis, PCR-mediated mutagenesis) or by chemically synthesizing a nucleic acid molecule having such changes. Such nucleic acid changes can lead to conservative and/or non-conservative amino acid substitutions at one or more amino acid residues. A "conservative amino acid substitution" is one in which one amino acid residue is replaced with a different amino acid residue having a similar side chain (see, for example, Dayhoff et al. (1978, in Atlas of Protein Sequence and Structure, 5(Suppl. 3):345-352), which provides frequency tables for amino acid substitutions), and a non-conservative substitution is one in which an amino acid residue is replaced with an amino acid residue that does not have a similar side chain.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is "purified."

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

A vector or construct containing a nucleic acid (e.g., a nucleic acid that encodes a polypeptide) also is provided. Vectors, including expression vectors, are commercially available or can be produced by recombinant DNA techniques routine in the art. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6xHis tag (SEQ ID NO: 43), glutathione S-transferase (GST)).

Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins. As used herein, operably linked means that a promoter or other expression element(s) are positioned in a vector relative to a nucleic acid in such a way as to direct or regulate expression of the nucleic acid (e.g., in-frame).

Vectors as described herein can be introduced into a host cell. As used herein, "host cell" refers to the particular cell into which the nucleic acid is introduced and also includes the progeny of such a cell that carry the vector. A host cell can be any prokaryotic or eukaryotic cell. For example, nucleic acids can be expressed in bacterial cells such as E. coli, or in insect cells, yeast or mammalian cells (such as Chinese hamster ovary cells (CHO) or COS cells). Other suitable host cells are known to those skilled in the art. Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer.

Nucleic acids can be detected using any number of amplification techniques (see, e.g., PCR Primer: A Laboratory Manual, 1995, Dieffenbach & Dveksler, Eds., Cold Spring Harbor Laboratory Press, Cold Spring Harbor, N.Y.; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid.

Nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.; Sections 7.37-7.57, 9.47-9.57, 11.7-11.8, and 11.45-11.57). Sambrook et al. discloses suitable Southern blot conditions for oligonucleotide probes less than about 100 nucleotides (Sections 11.45-11.46). The Tm between a sequence that is less than 100 nucleotides in length and a second sequence can be calculated using the formula provided in Section 11.46. Sambrook et al. additionally discloses Southern blot conditions for oligonucleotide probes greater than about 100 nucleotides (see Sections 9.47-9.54). The Tm between a sequence greater than 100 nucleotides in length and a second sequence can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a nucleic acid but not to another nucleic acid if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantitated directly on a membrane or from an autoradiograph using, for example, a PhosphorImager or a Densitometer (Molecular Dynamics, Sunnyvale, Calif.).

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed.

Detection (e.g., of an amplification product, a hybridization complex, or a polypeptide) is usually accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

Medium-Chain Fatty Acids and Methods of Making Medium-Chain Fatty Acids

The nucleic acids described herein, and the polypeptides encoded thereby, can be used to engineer a variety of useful medium-chain fatty acids and triacylglycerols that incorporate such medium-chain fatty acids. As used herein, medium-chain fatty acids refer to 6- to 14-carbon long saturated fatty acids; specifically, caprioc (C6:0), caprylic (C8:0), capric (C10:0), lauric (C12:0), and myristic (C14:0) acids. Coconut and palm-kernel oils naturally contain high amounts of medium-chain fatty acids. Medium-chain triacylglycerols (MCTs) usually contain unsaturated 6- to 14-carbon fatty acid esters of glycerol, but the nucleic acids described herein and the polypeptides encoded thereby can be used to produce TAGs containing predominantly C8:0, C10:0, or C12:0 fatty acid esters at the sn-2 position. As used herein, "predominantly" refers to at least 20% of the TAGs (e.g., at least 25%, 30%, 40%, 50%, 60%, 70%, 75%, 80%, 90% or 95% of the TAGs) having a C8:0 or a C10:0 at the sn-2 position.

For example, FatBs that can generate C8 and C10 fatty acids (e.g., ChFatB2 or CvFatB1) can be used in combination with at least one of the novel acyltransferases described herein to strongly enhance the production of TAGs having a saturated C8 or C10 at the sn-2 position. Also for example, a FatB that can generate C14 and C16 fatty acids (e.g., CpFatB2) can be used in combination with at least one of the novel acyltransferases described herein to strongly enhance the production of TAGs having a saturated C14 or C16 at the sn-2 position. It would be appreciated that other FatB sequences can be used in combination with at least one of the acyltransferases described herein to engineer useful medium-chain fatty acids and the TAGs incorporating them.

Significantly, the LPATs and DGATs described herein have unprecedented specificity for C8 and C10 fatty acids. Also significantly, the combination of one of the LPAT sequences disclosed herein and one of the DGAT sequences disclosed herein, in combination with a FatB sequence, results in a synergistic effect on the production of fatty acids and, consequently, the TAGs incorporating such fatty acids. Although not wishing to be bound by any particular mechanism, the observed synergy likely is because the LPATs described herein generate higher levels of DAGs with saturated fatty acids at the sn-2 position, which likely is the preferred substrate for DGATs described herein.

At least one of the acyltransferase sequences described herein can be expressed (e.g., overexpressed) in a transgenic organism in order to produce oils or triacylglycerols one or more medium-chain fatty acids. Therefore, transgenic organisms are provided that are transformed with at least one of the acyltransferase nucleic acid molecules described herein (e.g., SEQ ID NOs: 1, 3, 5, 7, or 9) or a functional fragment thereof, under control of a promoter that is able to drive expression. As discussed herein, a nucleic acid molecule used in a plant expression vector can have a different sequence than a sequence described herein, which can be expressed as a percent sequence identity (relative to, e.g., SEQ ID NOs: 1, 3, 5, 7, or 9) or based on the conditions under which the sequence hybridizes to, e.g., SEQ ID NOs: 1, 3, 5, 7, or 9.

As an alternative to using a full-length sequence, a portion of the sequence can be used that encodes a polypeptide fragment having the desired functionality (referred to herein as a "functional fragment"). When used with respect to nucleic acids, it would be appreciated that it is not the nucleic acid fragment that possesses functionality but the encoded polypeptide fragment. Based on the disclosure herein, one of skill in the art can predict the portion(s) of a polypeptide (e.g., one or more domains) that may impart the desired functionality.

In addition to at least one of the acyltransferases disclosed herein, the organisms also can contain a nucleic acid encoding a MCFA-specific thioesterase (FatB). Numerous FatB sequences are known in the art (e.g., without limitation, SEQ ID NOs: 11 and 13), or the novel FatB sequence disclosed herein (e.g., SEQ ID NO:15) can be used. In some embodiments, the FatB sequence is heterologous to the organism; in some embodiments, the FatB sequence is endogenous to the organism.

Methods of introducing one or more nucleic acids (e.g., one or more heterologous nucleic acids, one or more transgenes) into cells, including plant cells, are known in the art and include, for example, particle bombardment, *Agrobacterium*-mediated transformation, microinjection, polyethylene glycol-mediated transformation (e.g., of protoplasts, see, for example, Yoo et al. (2007, *Nature Protocols*, 2(7):1565-72)), liposome-mediated DNA uptake, or electroporation. Following transformation of plant cells, the transgenic cells can be regenerated into transgenic plants. As described herein, expression of the transgene results in an organism that produces, or exhibits an increased amount of, medium-chain fatty acids (relative to a corresponding organism not containing or not expressing the transgene). The transgenic organisms can be screened for the amount of medium-chain fatty acids, and the medium-chain fatty acids can be obtained (e.g., purified) from the organism.

Methods of detecting medium-chain fatty acids, and methods of determining the amount of one or more medium-chain fatty acids, are known in the art and are described herein. For example, high performance liquid chromatography (HPLC), gas liquid chromatography (GLC), liquid chromatography (LC), and ESI-MS/MS scans can be used to detect the presence of one or more medium-chain fatty acids and/or determine the amount of one or more medium-chain fatty acids. Lipase digestion of triacylglycerols can also be used to establish the content of medium-chain fatty acids at the sn-2 position of triacylglycerols.

As used herein, an "increase" refers to an increase (e.g., a statistically significant increase) in the amount of medium-chain fatty acids or oils or triacylglycerols in plants by at least about 5% up to about 95% (e.g., about 5% to about 10%, about 5% to about 20%, about 5% to about 50%, about 5% to about 75%, about 10% to about 25%, about 10% to about 50%, about 10% to about 90%, about 20% to about 40%, about 20% to about 60%, about 20% to about 80%, about 25% to about 75%, about 50% to about 75%, about 50% to about 85%, about 50% to about 95%, and about 75% to about 95%) relative to the amount from a non-transgenic organism. As used herein, statistical significance refers to a p-value of less than 0.05, e.g., a p-value of less than 0.025 or a p-value of less than 0.01, using an appropriate measure of statistical significance, e.g., a one-tailed two sample t-test.

When the organism is a microbe, a highly expressing or constitutive promoter can be used to direct expression of the at least one acyltransferase. Transgenic microbes then can be cultured or fermented in order to obtain the medium-chain fatty acids. When the organism is a plant, it generally is desirable, although not absolutely required, to use a seed-specific promoter to direct expression of the at least one acyltransferase. Significantly, the promoters of the acyltransferases described herein are seed-specific, and thus, can be used to direct expression of the sequences in a transgenic plant. Transgenic plants having increased amounts of medium-chain fatty acids, compared to the amount in a corresponding non-transgenic plant, can be selected for use in, for example, a breeding program as discussed in more detail below.

Following transformation, transgenic To plants are regenerated from the transformed cells and those plants, or a subsequent generation of that population (e.g., $T_1$, $T_2$, $T_3$, etc.), can be screened for the presence of the at least one acyltransferase (e.g., SEQ ID NOs: 1, 3, 5, 7, or 9) or for the phenotype (e.g., an increase in the amount of medium-chain fatty acids compared to a non-transgenic plant or a transgenic plant not expressing the transgene). Screening for plants carrying at least one acyltransferase can be performed using methods routine in the art (e.g., hybridization, amplification, combinations thereof) or by evaluating the phenotype (e.g., detecting and/or determining the amount of one or more medium-chain fatty acids in the plant (e.g., in the seed)). Generally, the presence and expression of the at least one acyltransferase (e.g., SEQ ID NOs: 1, 3, 5, 7, or 9) results in an increase of one or more medium-chain fatty acids in the plants (e.g., in seeds from the plants) compared to a corresponding plant (e.g., having the same varietal background) lacking or not expressing the at least one acyltransferase.

A plant carrying the at least one acyltransferase (e.g., SEQ ID NOs: 1, 3, 5, 7, or 9) can be used in a plant breeding program to create novel and useful cultivars, lines, varieties and hybrids. Thus, in some embodiments, a $T_1$, $T_2$, $T_3$ or later generation plant containing the at least one acyltransferase is crossed with a second plant, and progeny of the cross are identified in which the at least one acyltransferase is present. It will be appreciated that the second plant can be one of the species and varieties described herein. It will also be appreciated that the second plant can contain the same transgene or combination of transgenes as the plant to which it is crossed, a different transgene, or the second plant can carry a mutation or be wild type at the endogenous locus. Additionally or alternatively, a second line can exhibit a phenotypic trait such as, for example, disease resistance, high yield, height, plant maturation, stalk size, and/or leaf number per plant.

Breeding is carried out using known procedures. DNA fingerprinting, SNP or similar technologies may be used in a marker-assisted selection (MAS) breeding program to transfer or breed the transgene(s) into other lines, varieties or cultivars, as described herein. Progeny of the cross can be screened for the transgene(s) using methods described herein, and plants having the transgenes described herein (e.g., SEQ ID NOs: 1, 3, 5, 7, or 9) can be selected. For example, plants in the $F_2$ or backcross generations can be screened using a marker developed from a sequence described herein or a fragment thereof, using one of the techniques listed herein. Seed from progeny plants also can be screened for the amount of one or more medium-chain fatty acids, and those plants having increased amounts, compared to a corresponding plant that lacks the transgene, can be selected. Plants identified as possessing the transgene and/or the expected phenotype can be backcrossed or self-pollinated to create a second population to be screened. Backcrossing or other breeding procedures can be repeated until the desired phenotype of the recurrent parent is recovered.

Successful crosses yield $F_1$ plants that are fertile and that can be backcrossed with one of the parents if desired. In some embodiments, a plant population in the $F_2$ generation is screened for the transgene using standard methods (e.g., PCR with primers based upon the nucleic acid sequences disclosed herein). Selected plants are then crossed with one of the parents and the first backcross ($BC_1$) generation plants are self-pollinated to produce a $BC_1F_2$ population that is again screened for the transgene or the phenotype. The process of backcrossing, self-pollination, and screening is repeated, for example, at least four times until the final screening produces a plant that is fertile and reasonably similar to the recurrent parent. This plant, if desired, is self-pollinated and the progeny are subsequently screened again to confirm that the plant contains the transgene and exhibits the expected phenotype. Breeder's seed of the selected plant can be produced using standard methods including, for example, field testing, confirmation of the presence of the transgene, and/or chemical analyses of the plant (e.g., of the seed) to determine the level of medium-chain fatty acids.

The result of a plant breeding program using the transgenic plants described herein are novel and useful cultivars, varieties, lines, and hybrids. As used herein, the term "variety" refers to a population of plants that share constant characteristics which separate them from other plants of the same species. A variety is often, although not always, sold commercially. While possessing one or more distinctive traits, a variety is further characterized by a very small overall variation between individuals within that variety. A "pure line" variety may be created by several generations of self-pollination and selection, or vegetative propagation from a single parent using tissue or cell culture techniques. A "line," as distinguished from a variety, most often denotes a group of plants used non-commercially, for example, in plant research. A line typically displays little overall variation between individuals for one or more traits of interest, although there may be some variation between individuals for other traits.

A variety can be essentially derived from another line or variety. As defined by the International Convention for the Protection of New Varieties of Plants (Dec. 2, 1961, as revised at Geneva on Nov. 10, 1972, On Oct. 23, 1978, and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it confirms to the initial variety in the expression of the essential characteristics that result from the genotype or combination of genotypes of the initial variety. Essentially derived varieties can be obtained, for example, by the selection of a natural or induced mutant, a somaclonal variant, a variant individual plant from the initial variety, backcrossing, or transformation.

Hybrids can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), nuclear male sterility, genetic male sterility, molecular male sterility wherein a transgene inhibits microsporogenesis and/or pollen formation, or self-incompatibility. Female parent plants containing CMS are particularly useful. In embodiments in which the female parent plants are CMS, the male parent plants typically contain a fertility restorer gene to ensure that the $F_1$ hybrids are fertile. In other embodiments in which the female parents are CMS, male parents can be used that do not contain a fertility restorer. $F_1$ hybrids produced from such parents are male sterile. Male sterile hybrid seed can be interplanted with male fertile seed to provide pollen for seed-set on the resulting male sterile plants.

Varieties, lines and cultivars described herein can be used to form single-cross $F_1$ hybrids. In such embodiments, the plants of the parent varieties can be grown as substantially homogeneous adjoining populations to facilitate natural cross-pollination from the male parent plants to the female parent plants. The $F_2$ seed formed on the female parent plants is selectively harvested by conventional means. One also can grow the two parent plant varieties in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

The microbial organisms used in the methods described herein include, without limitation, bacteria (*E. coli, Pseudomonas* sp.), cyanobacteria (*Synechocystis* sp), and green microalgae (*C. reinhardtii, Phaeodactylum tricornutum, Chlorella* sp., *Nannochloropsis* sp.) species, fungal (*Yarrowia lipolytica, Saccharomyces cerevisiae*) species. The plants used in the methods described herein can be oilseed plants such as, without limitation, *Camelina* spp. (e.g., *Camelina sativa, Camelina alyssum, Camelina rumelica*) or other Brassicaceae spp. (e.g., *Brassica oleracea, Brassica rapa, Brassica napus, B. carinata*), *Limnanthes alba* (meadowfoam), *Glycine max* (soybean), *Linum* spp. (e.g., *Linum usitatissimum*, flax), *Crambe* spp. (e.g. *Crambe abyssinica*), *Ricinus communis* (castor bean), *Gossypium* spp. (e.g. *Gossypium hirsutum* cotton), or non-oilseed plants such as, without limitation, legumes (e.g., peas, beans), tuberous crops (potato, cassava), or other crop plant.

The MCFAs or TAGs comprising MCFAs produced in the methods herein can be used in any number of products in which a medium-chain fatty acid or a TAG containing such a medium-chain fatty acid is desired. Such products include, without limitation, biofuel and/or jet fuel. For example, vegetable oils with TAGs containing fatty acid chains having 10 or less carbons are more desirable feedstocks for the biofuel industry due to their lower viscosity and because such vegetable oils may not require trans-esterification, which is usually a required step when converting vegetable oils to biodiesel. In addition, the MCFAs or the TAGs comprising MCFAs produced as described herein can be used in detergents, cosmetics, surfactants, or feedstocks for preparation of other specialized chemicals.

In addition, in some embodiments, one or more of the acyltransferases described herein can be used in industrial inter-esterification of fatty acids to generate particular TAGs or one or more of the acyltransferases described herein can be used in a bioreactor (e.g., one or more of the acyltransferases described herein can be immobilized) to make particular TAGs for specialized nutritional or industrial applications.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Part A

Example 1—Plant Material, Growth and Transformation Conditions

*Camelina sativa* seed was sowed into 81 cm² square green plastic pots with Fafard Germination Mix based soil. Natural ambient light was supplemented in the greenhouses with a combination of metal halide and high pressure sodium lights. Lights was provided for a 14 hour day-length. During the daytime temperatures were set at a range of 24° C.-26° C. and during the nighttime temperatures were set at a range 18° C.-20° C. When outdoor temperatures were above 29° C. the supplemental lights were shut off to reduce the need for extra cooling. *Agrobacterium tumefaciens* cells (strain C58C1) were transformed with the binary vectors containing LPAT cDNA by the electroporation. *Camelina* plants were transformed by floral dip followed by vacuum infiltration and a fluorescent protein (DsRed) was used as a visual selection marker (Lu & Kang, 2008, Plant Cell Rep., 27:273-8). Segregation analyses were performed on the T2 showed fluorescence seeds to determine the number of T-DNA insertion loci. Plants homozygous for the transgene were identified by screening T3 seeds for 100% red fluorescence.

Example 2—RNA Isolation from *Cuphea* Species and cDNA Conversion

Total RNAs were isolated from different *Cuphea* tissues such as roots, stems, leaves, flowers and developing seeds using slightly modified methods described in the previous report (Chang et al., 1993, Plant Mol. Biol. Report., 11:113-6) and RNeasy Plant Mini Kit (Qiagen). The first step was performed by the CTAB-based procedure. A pre-heated 10 ml of extraction buffer (2% w/v CTAB, 2% w/v PVP, 2 M NaCl, 100 mM Tris-HCl pH 8.0, 25 mM EDTA pH 8.0 and 0.05% w/v of spermidine) was added to the sample (200-300 mg) ground in liquid nitrogen, mixed vigorously by vortexing and incubated at 65° C. for 10 min. The sample was divided into several new microcentrifuge tubes. An equal volume of chloroform was added and the tubes, mixed vigorously and then centrifuged at 13,000 rpm for 10 min at 4° C. The supernatant was transferred to new microcentrifuge tubes and ⅓ volume of 8 M LiCl was added. The mixture was incubated in ice for overnight, and the RNA was selectively collected after centrifugation at 13000 rpm for 1 hour at 4° C. The pellet was resuspended in 500 µl of RLT buffer in RNeasy Plant Mini Kit and was then carried out as indicated in the manufacturer's handbook including DNase I treatment. The first-strand cDNA was synthesized from 2 ug total RNA using RevertAid First Strand cDNA Synthesis Kit (Thermo Scientific) with oligo-(dT) primer.

Example 3—Confocal Laser Scanning Microscope

The expression of transient fluorescent fusion proteins in tobacco leaves was performed using the agro-infiltration methods as described previously (Sparkes et al., 2006, Nature Protocols, 1:2019-25). Two days after infiltration, the abaxial leaf surface was observed with a confocal laser scanning microscope (Olympus). For YFP and mCherry, the excitation wavelengths were respectively 488 nm and 545 nm, and the emitted fluorescence was collected at 495~530 nm and 565~600 nm, respectively.

Example 4—Complementation of *Cuphea* LPAT cDNAs by Expression in *Escherichia coli* Mutant The thermo-sensitive strain, *E. coli* JC201, was used to complement the deficient of LPAT activity (Coleman, 1992, Mol. Gen. Genet., 232:295-303). The *Cuphea* LPAT cDNAs were cloned into the into the pBluescript SK$^+$ multicloning site using SacI and NotI. JC201 was transformed via heat shock and was selected on ampicillin plates at 30° C. Complementing colonies were inoculated into starter cultures and grown to an optical density at 600 nm of 0.5 at 30° C. with or without 1 mM isopropylthio-β-galactoside (IPTG). Aliquots were grown in the presence of IPTG at 30° C. and 44° C., and growth curves were constructed using data obtained from three individual complementation experiments.

Example 5—Fatty Acid Analysis of Seed Oils

Fatty acid methyl esters (FAMEs) were generated by grinding 10 mg of dry seeds in 2 mL of 2.5% H2SO4 (v/v) in methanol including 900 μg of tri 17:0-TAG (Nu-Chek Prep, Elysian, Minn., USA) in toluene (10 mg/mL) as an internal standard and heated for 45 min at 90° C. in tightly capped tubes. Following cooling, 1.5 mL of water and 1.5 mL hexane were added to tubes and mixed vigorously. The organic phase was transferred to autosampler vials and analyzed on an Agilent Technologies 7890A gas chromatograph (GC) fitted with a 30 m length×0.25 mm inner diameter HP-INNOWax column (Agilent, Santa Clara, Calif., USA) using H2 carrier gas. The GC was programmed for an initial temperature of 90° C. (1 min hold) followed by an increase of 30° C. min-1 to 235° C. and maintained for a further 5 min. Detection was achieved using flame ionization.

Example 6—Neutral Loss ESI-MS/MS Analysis

Mass spectrometry analyses were conducted using an Applied Biosystems (Foster City, Calif.) 4000 QTRAP linear ion trap quadrupole mass spectrometer to characterize TAG molecular species. The total neutral lipid extract for ESI-MS/MS analysis was prepared as described for seed oil content measurement below but without added internal standard and diluted 1:5000 in water/isopropyl alcohol/methanol (55:35:10 v/v/v) containing 25 mm ammonium formate and 4 μL/L formic acid and directly infused into the mass spectrometer at a rate of 20 μL per minute. Instrument settings were as follows: Source temperature 400° C., ESI needle voltage 5.5 kV (positive mode), desolvation potential (DP) 90, entrance potential (EP) 10, Curtain gas (CUR) 10, and gas 1 (GS1) 50 arbitrary units, gas 2 (GS2) 40 arbitrary units. Neutral loss spectra showing the loss of a specific fatty acid from TAG species were generated by monitoring the loss of 189.1 m/z (for C10:0) and 245.1 m/z (for C14:0). Scans were taken over a mass range of 500-1475 m/z with a cycle time of 3 s. Data was collected for five cycles.

Example 7—RNA Isolation from Developing Seeds and cDNA Library Construction

Total RNA was isolated from *Cuphea pulcherrima* and *Cuphea viscosleaves* and developing seeds collected from greenhouse grown plants and immediately frozen in liquid nitrogen and stored at −80° C. until use in RNA isolation. Total RNA was isolated according to a method described previously (Mattheus et al., 2003, Phytochemical Analysis, 14:209-15; Suzuki et al., 2004, Biotechniques, 37:542-44). In brief, developing seeds were grounded to a fine powder in liquid nitrogen. The powders were transferred to a chilled centrifuge tube containing cold extraction buffer consisting of 100 mM Tris-HCl, pH 8.0, 50 mM ethylenebis (oxyethylenenitrilo) tetraacetic acid, pH 8.0, 100 mM sodium chloride, 1% 6-(p-toluidino)-2-naphthalenesulphonic acid, 6% sodium p-aminosalicylic acid, 1% SDS, 1% PVP-40, 3% PVPP:chloroform and 1% β-mercaptoethanol. The sample was centrifuged for 10 min with Sorvall SS-34 rotor, 10500 rpm at 4° C. The supernatant was transferred to a fresh tube. An equal volume of chloroform was added and the mixture was vortexed for 2 min, centrifuged for 10 min at 10500 rpm and 4° C. The aqueous phase was transferred to a fresh tube. The aqueous fraction was extracted twice with phenol:chloroform (1:1, v/v), and extracted once with chloroform. The RNA was precipitated overnight with 0.1 volume of 3 M sodium acetate (pH 5.2) and 2.5 volume of 95% ethanol at −20° C. The RNA was precipitated by centrifugation for 30 min at 10500 rpm and 4° C., rinsed once with 70% ethanol, briefly dried, and dissolved in DEPC-water.

Example 8-454 Transcriptome Analysis 200 ng of polyA+-enriched RNA prepared from developing seeds of *Cuphea pulcherrima* and *Cuphea viscosissma* was used in the preparation of a single sequencing library with custom adaptors according to methods of Nguyen, H. T., Silva, J. E., Podicheti, R., Macrander, J., Yang, W., Nazarenus, T. J., Nam, J. W., Jaworski, J. G., Lu, C, Scheffler, B. E., Mockaitis, K & Cahoon, E. B. (2013). The double-stranded cDNA library intermediate was partially normalized by DSN treatment (Evrogen) to reduce the representation of the transcripts of greatest abundance. Shearing prior to adaptor ligation was by nebulization (30 sec, 30 psi). The final library was assessed on a Bioanalyzer DNA7500 chip (Agilent) and showed a peak size of 660 bp. Emulsion PCR and sequencing was done according to the manufacturer (Roche/454 Sequencing). Two regions of two-region plus three regions of four-region GS-FLX Titanium PicoTitre™ plate were run to 800 cycles.

The *Cuphea pulcherrima* and *Cuphea viscosissma* transcriptome assemblies were matched by BLASTX using BLOSUM62 scoring matrix and a word size of 3, to protein sequences of TAIR10 representative gene models (*Arabidopsis*.org on the World Wide Web) with an E-value limit of 1 e-5. The top hit(s) for each query sequence was retained based on best bit score and E-value. Secondly TAIR10 models (above) were matched to assembly elements (isotigs and singletons) using tBLASTN with an E-value limit of 1 e-5. Candidate acyl lipid metabolism gene sequences were retrieved from BLAST result sets above were trimmed to include only these genes. The best isotig for each isogroup was retained, trimming out putative alternative transcripts of the same gene (as described in Nguyen et al., 2013, *Plant Biotechnol. J.*, 11(6), 759-769.

Example 9—Isolation of Multiple Putative LPAT Paralogs in *Cuphea* Species

To isolate specialized LPAT for medium chain acyl-CoA, we performed the RNA sequencing and assembly of over 2 million 454 sequencing pyrosequencing reads from the developing seeds of *C. pulcherrima* (recently re-classified as

*C. avigera* var. *pulcherrima*) and *C. viscosissima*. Nucleotide sequence similarity to *Arabidopsis* LPAT2 was used for identification of potential LPAT orthologs. Six full-lengths of LPAT candidate genes were isolated in the 454 sequencing transcriptome of *C. pulcherrima*, and one full-length of LPAT candidate gene was found in the 454 sequencing transcriptome of *C. viscosissima*. We used the 7 full-lengths of putative LPAT genes for further studies.

The evolutionary relationship of *cuphea* LPAT genes was investigated based on their deduced amino acid sequences to collect more information about relationships and to predict function for TAG accumulation. The sequences were aligned with putative orthologs of higher plants, which were described by Manas-Fernandez et al. (2013, Europ. J. Lipid Sci. Technol., 115:1334-6) and Arroyo-Caro et al. (2013, Plant Sci., 199:29-40), and obtained the sequences from the protein database of the National Center for Biotechnology Information (NCBI). LPATs have been sub-grouped by plastid LPAT (LPAT1) and microsomal LPAT, and then the latter was further categorized into two classes, A and B. The class A microsomal LPATs are typical enzymes involved in synthesis of membrane glycerolipids, they show ubiquitous expression in plants and have a substrate preference for 18:1-CoA. Based on the category of *Arabidopsis* LPATs, the class A microsomal LPATs were further divided into 2 subgroups as LPAT2/LPAT3 group and LPAT4/LPAT5 group. The class B microsomal LPAT (LPATB) is classified as a seed-specific isoform and is found in plants accumulating unusual fatty acids in their seed oil. Even though LPATB is a microsomal LPAT, the class has a closer relationship with plastidal LPAT1 than other plant groups. However, LPATB is closer to the enzyme of other organisms, such as *E. coli*, yeast, and human.

Figure 1:
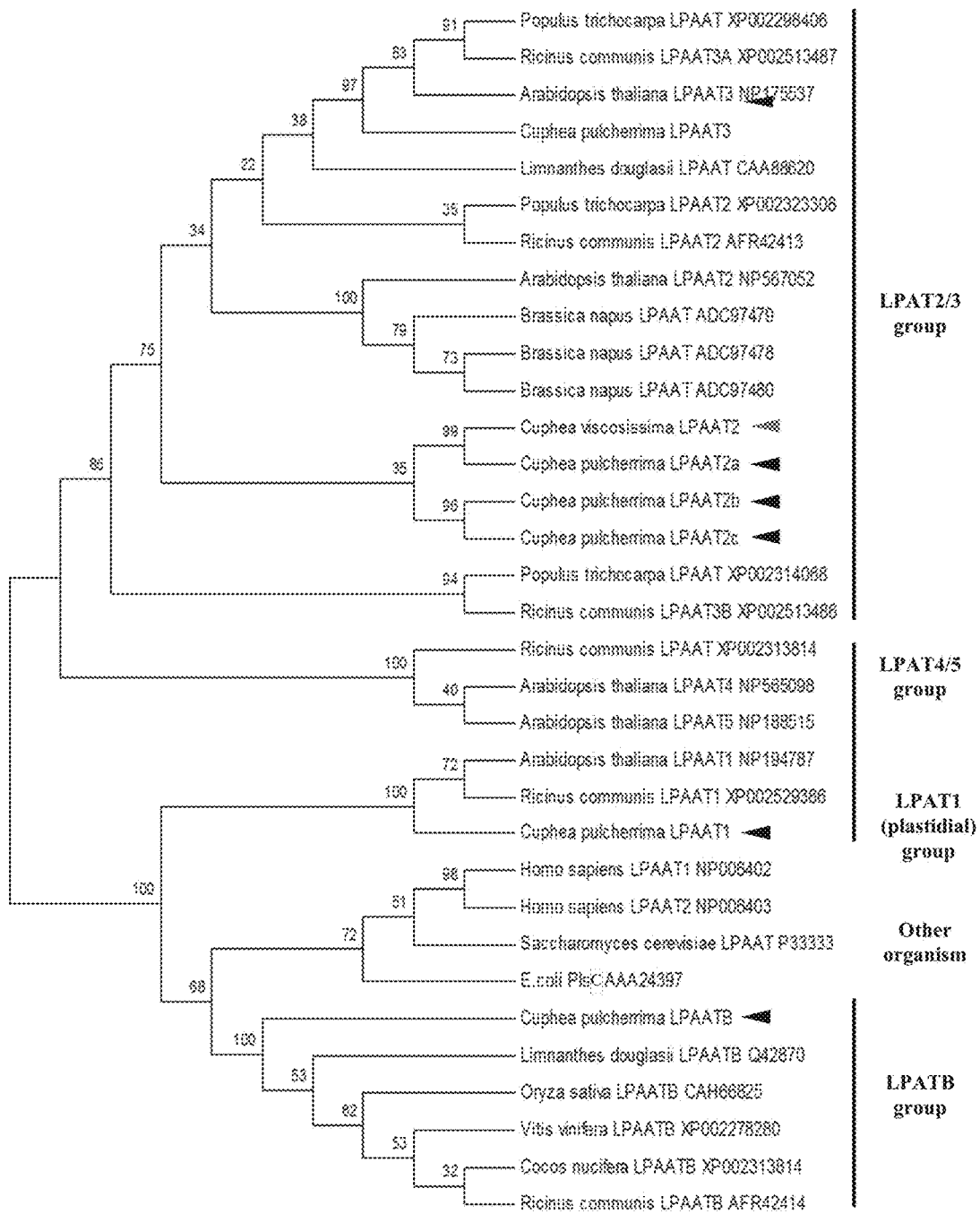
FIG. 1 shows the phylogenic relationship in deduced amino acid sequences of LPATs. Amino acid sequences of 6

Four genes of class A LPAT, one gene of LPATB, and one gene of LPAT1 were found in *C. pulcherrima*. Based on the classification, these LPATs were named as CpuLPAT1, CpuLPAT2a, CpuLPAT2b, CpuLPAT2c, CpuLPAT3 and CpuLPATB (FIG. 1). One LPAT gene from *C. viscosissima* was isolated, classified as class A, and named as CvLPAT2 (FIG. 1). CpuLPATB belonged to the same group as CnLPAT, which was isolated in coconut and related to increase of lauric acid by incorporating this fatty acid into the sn-2 position of TAG in transgenic plants seeds (Knutzon, et al., 1999, Plant Physiol., 109:999-1006). Based on the relationship between coconut LPATB and MCFA, we assumed that CpuLPATB might involve the increase of MCFA in TAG. So the studies were focused to reveal the function of CpuLPATB. Because CvLPAT2 was the only LPAT gene isolated from *C. viscosissima*, the functional studies of CvLPAT2 were performed in parallel.

Example 10—Acyltransferase Motifs and Topology of Transmembrane Domain in *Cuphea* LPATs An amino acid alignment reveals a high level of amino acid identity among plant LPATBs (FIG. 2A). The LPLAT-AGPAT-like domain of CpuLPATB shared 82%, 79%, 77%, 74% and 70% identities with *Vitis vinifera* (XP 002278280), *Ricinus communis* [AFR42414], *Oryza sativa* (CAH66825), *Cocos nucifera* [Q42670], and *Limnanthes douglasii* [Q42870], respectively. The domain showed a low identity with other organisms such as 40% (*Homo sapiens*, NP006402), 39% (*Homo sapiens*, NP006403), 36% (*Saccharomyces cerevisiae*, SLC1, P33333), and 34% (*Escherichia coli*, PlsC, AAA24397). We predicted that there were 4 conserved acyltransferase motifs in CpuLPATB, which are $NH(X)_4D$ (motif I, residues 137-143), GHLRIDR (SEQ ID NO: 44) (motif II, residues 178-183), FPEGTR (SEQ ID NO: 45) (motif III, residues 210-215), and LPIVPIVL (SEQ ID NO: 46) (motif IV, residues 237-244) (FIG. 7A). These are significantly important on acyltransferase activities. Hydrophobic motif II was first characterized as an acyl-CoA-binding site in animal cells and might modulate acyl-CoA selectivity and residue "EGT" in motif III has been presumed to be involved in the binding of the LPA.

To predict transmembrane domain sequences, structural analysis of the gene model-translated protein sequences was carried out in silico using SOSUI [bp.nuap.nagoya-u.ac.jp/sosui/on the World Wide Web], PSORTII [psort.hgc.jp/form2.html on the World Wide Web], HMMTOP [enzim.hu/hmmtop/on the World Wide Web], and TMHMM server 2.0 [cbs.dtu.dk/services/TMHMM/ on the World Wide Web]. All programs predicted only one transmembrane domain in CpuLPATB in a similar region (FIG. 7B). Based on the analysis of motif and transmembrane domain, the predicted topology of CpuLPATB was presented in FIG. 7C, where all acyltransferase motifs were on the cytosolic side of the ER membrane.

The deduced amino acid sequence alignment of CvLPAT2 with CpuLPAT2a, CpuLPAT2b CpuLPAT2c, and CpuLPAT3 showed the amino acid identities as 82%, 79%, 79% and 66%, respectively, in full amino acid sequences, and 87%, 79%, 79% and 66%, respectively, in LPLAT-AGPAT-like domain. The amino acid identity between CpuLPAT2b and CpuLPAT2c was the highest at 97% in LPLAT-AGPAT-like domain. The key motifs in LPLAT-AGPAT-like domains were conserved well among the LPAT2s in diverse plant species (FIG. 8A). As for Motif I [$NH(X)_4D$] and motif III (FPEGTR) (SEQ ID NO: 45), the same sequences with LPATTB, were observed in CvLPAT2 and in LPAT2/3 group from *C. pulcherrima*. Motif II (LPVLGW) (SEQ ID NO: 47) and motif IV (NVLIPRTKGFV) (SEQ ID NO: 48) were conserved in plant LPAT2/3 group, but those sequences were completely different with the LPATB's. There was a putative tyrosine phosphate site in motif V [$R(X)_6Y(X)_4A$] from CvLPAT2 like the other LPAT2/3 group. Transmembrane domain of CvLAAPT2 was predicted as different numbers by different programs; 4 by SOSUI, 3 by PSORTII and HMMTOP and 5 by TMHMM (FIG. 8B). All programs predicted the N-terminal located in cytosol and C-terminal located in the ER lumen. Therefore, we predicted that there are five transmembrane domains in CvLPAT2 as seen in caster bean and presented the predicted topology of CvLPAT2 in FIG. 8C, where motif I is located in cytosol and motif II-IV is located in the ER lumen by separating the third transmembrane domain.

Example 11—Tissue-Specific Expression of *Cuphea* LPAT Isoforms

Different LPAT isoforms showed the various expression patterns and levels in the diverse tissues of a plant. Because LPAT has been considered a narrow substrate specificity, tissue specific expression is one of the clues to presume their function. RT-PCR was performed using cDNAs from diverse tissues, such as roots, stems, leaves, flowers and developing seeds, to investigate the tissue specificity and the expression level of LPAT genes in *C. pulcherrima* and *C. viscosissima* (FIG. 2). The transcripts of CpuLPAT1 were abundant in all tested tissues except developing seeds. CpuLPAT2b and CpuLPAT3 showed ubiquitous expression patterns with a low expression levels. CpuLPAT2c was undetectable at the same PCR cycle numbers as other LPAT genes, however, when PCR cycle numbers were increased it was slightly detected in all tissues tested. Interestingly, CpuLPAT2a and CvLPAT2, which have very high sequence similarity (82% in amino acid), showed the developing seed-specific expressions. CpuLPATB was also exclusively detected in the developing seeds. These results indicate that CpuLPATB, CpuLPAT2a and CvLPAT2 might be involved in the accumulation of MCFAs at the sn-2 position of TAG.

Example 12—CpuLPATB, CpuLPAT2a, and CvLPAT2 Localize in the ER

The ER localization of LPAT2 was confirmed in *Arabidopsis* and *Brasicca* by immunofluorescence microscopy of tapetum cells and by immunoblotting of subcellular fraction. We investigated the subcellular localization of CpuLPAT2a, CpuLPATB, and CvLPAT2 by using a laser scanning confocal microscope. Yellow fluorescence protein (YFP) was fused with C-terminal of each LPAT driven by 35S promoter. Each pro35S:LPAT:YFP was transiently co-expressed with the ER-rk CD3-959 as the ER marker (FIG. 3A-C) in tobacco leaves by agro-infiltration method. YFP signals of CpuLPAT2a, CpuLPATB, and CvLPAT2 were detected as the reticular shape and co-localized with ER marker. The result demonstrated that CpuLPAT2a, CpuLPATB, and CvLPAT2 are microsomal LPAT localized in the ER. We also tested the subcellular localization of CpuLPAT1, which is classified as a plastidal form. YFP signal of CpuLPAT1 was detected in the out membrane of chloroplasts (FIG. 3D).

Example 13—CpuLPATB Complemented the *E. coli* Mutant, JC201

To test the activities of *Cuphea*. LPATs, a complementation test was performed in an *E. coli* JC201 mutant, which is a temperature-sensitive mutant of plsC and able to grow at 30° C., but not at 42° C. The full-length open reading frames of *Cuphea* LPATs were cloned into the pBluescript SK+ vector. FIG. 4A showed that all *Cuphea* LPATs and an empty vector grew at 30° C. Occasionally the JC201 cells with an empty vector grew at 42° C., and we increased the incubation temperature as 44° C. Only JC201 containing CpuLPATB was able to grow at 44° C., but few colonies were observed in the JC201 containing other LPATs (FIG. 4A). To confirm the result, we tested their growth rate by measuring the ODconcentration in process of time. As seen in FIG. 4B, the cell concentration of JC201 increased in all tested *Cuphea* LPATs and empty vector control at 30° C. However, only CpuLPATB showed the increase of OD concentration at 44° C. We tested the LPAT activity in the inducible vector, pET-duet, but the results were the same as above, even in the presence or absence of IPTG, Only CpuLPATB complemented the *E. coli* mutant JC201 a LPAT activity. This result was correlated with the amino acid homology of LPATs between plant and *E. coli*. CpuLPATB shares the most similar homology with *E. coli* LPAT (34% in domain).

Example 14—CpuLPATB and CvLPAT2 Preferentially Incorporated 14:0 and 10:0, Respectively, into the Sn-2 Position of TAG To investigate the activities of *Cuphea* LPATs in planta and its utility for oilseed metabolic engineering, the CpuLPATB and CvLPAT2 genes were introduced into *Camelina* along with the variant FatB thioesterase genes. CpFatB2 is 14:0 specific thioesterase of *Cuphea palustris* (Dehesh et al., 1996, Plant Physiol., 110:203-10) and ChFatB2 is 8:0 and 10:0 specific FatB thioesterase of *Cuphea hookeriana* (Dehesh et al., 1996, The Plant J., 9:167-72). The seed-specific glycinin promoter was used to drive the CpuLPATB and the seed-specific oleosin promoter was used to drive the CvLPAT2 for exclusive gene expression in seed. Lauric acid-specific CnLPAT was used for a comparison with CpuLPATB and CvLPAT2. The expression of CpFatB2 in *Camelina* showed 26.3 mol % of 14:0 fatty acid. When CpFatB2 was co-experessed with CnLPAT, CpuLPATB or CvLPAT2, the levels of 14:0 fatty acid were further increased as 33.1 mol %, 36.5 mol % or 32.9 mol %, respectively. The expression of ChFatB2 in *Camelina* showed 7.4 mol % of 10:0 fatty acid. Co-expression of ChFatB2 with CnLPAT or CvLPAT2 increased the 10:0 fatty acid as 10.2 mol % or 11.8 mol %, respectively. However, CpuLPATB didn't increase the 10:0 fatty acid with ChFatB2 (FIG. 5). The positional distribution of the MCFA was also determined in TAG. Trace amounts of 16:0 and 18:0 were detected at the sn-2 position of TAG in wild type. The composition of MCFA at the sn-2 position of TAG was 2.9 mol % (14:0) and 1.1 mol % (16:0) in CpFatB2 *Camelina* seeds. Myristic acid the sn-2 position of TAG from CpFatB2 *Camelina* seeds was significantly increased up to 14.2 mol % with CnLPAT, 19.7 mol % with CpuLPATB, and 14.8 mol % with CvLPAT2 (FIG. 5B). The sn-2 position of TAG in ChFatB2 was not occupied by any MCFA or saturated fatty acid. Co-expression of ChFatB2 with CvLPAT2 resulted in the significant increase of 10:0 (15.4 mol %) at the sn-2 position of TAG. However, 10:0 fatty acid was barely detected in the coexpression line of ChFatB2 and CnLPAT. CpuLPATB didn't effect on the increase of 10:0 fatty acid with ChFatB2 in the transgenic *Camelina* seeds. These results indicate that CpuLPATB and CvLPAT2 enhance the accumulation of the saturated MCFAs in the TAG of *Camelina* seed by incorporating medium chain acyl-CoA into the sn-2 position of LPA. CpuLPATB has a preference toward 14:0 fatty acid and CvLPAT2 has a preference toward myristic acid and capric acid.

Example 15—The Distribution of MCFA in TAG Molecular Species

To further investigate the metabolism of MCFA in transgenic *Camelina* seeds, we performed ESI-MS analysis for the molecular species of TAG from *Camelina* producing the FatB TE. Absolute peak intensity of mass spectra of TAG species from seeds expressing the FatB TE and LPAT were presented in FIG. 6 and FIG. 10. TAG species with at least one 14:0 represent in plants expressing CpFatB2 with CnLPAT, CpuLPATB, and CvLPAT2, respectively, while any MCFA was not detected in the TAG in wild-type *Camelina* (FIG. 6). The levels of tri-MCFA-TAG species increased when CpFatB2 expressed with LPATs and the highest amount tri-MCFA-TAG species was observed in CvLPAT2. Tri-MCFA-TAG species in transgenic *Camelina* seeds confirmed that tested LPATs contain the preference to saturated MCFAs and CvLPAT2 is the best FatB TE for those substrates.

Part B

Example 16—Cloning CpDGAT1 Sequence from *C. pulcherrima*

The CpDGAT1 gene sequence was identified in the *C. pulcherrima* 454 sequence data generated as described before (Nguyen et al., 2013, Plant Biotechnol. J., 11:759-

69). The ORF designated as CpDGAT1 of 1482 bp encoding 484 amino acids was PCR amplified from *C. pulcherrima* cDNA using the gene specific primers.

For expression in yeast the native version of CpDGAT1 ORF was amplified using the primer pair CpDGAT1BamHIf and CpDGAT1XbaIr. The ORFs for N terminus truncated and mutated versions were generated using the forward primers CpDGAT1trunc_BamHI and CpDGAT1AlaBamHIf, respectively. The ORF for the truncated version (CpDGAT1trunc) of CpDGAT1 is 70 amino acids shorter at N terminus than the native version. The alignment showed that the 70 amino acid N terminus of CpDGAT1 is unique and is different from that of other DGAT1s while the amino acid sequence downstream the 70 amino acids is highly similar to that of DGAT1s from *A. thaliana*, *O. europea*, *B. napus* and *O. sativa*. The length of the differing N terminus region of the DGAT1s from different plant species varies. In the mutated version the CAT coding for $^1$His was replaced by GAG coding for Ala in the forward primer, CpDGAT1AlaBamHIf. Thus three constructs pYes2_CpDGAT1, pYes2_CpDGAT1Ala, and pYes2_CpDGAT1trunc were made for expression in yeast.

For generating plant transformation vectors the ORF encoding for CpDGAT1 and CpDGAT1trunc were subcloned into NotI sites of pKMS3 vector generating Glycinin promoter and terminator containing CpDGAT1 gene cassette. The cassette was subsequently released by AscI to be cloned into MluI site of pBinGlyRed3+CvFatB1 yielding pBinGlyRed3_CvFatB1+CpDGAT1 or pBinGlyRed3_CvFatB1+CpDGAT1trunc. The backbone of the vector is derived from pCAMBIA0380 and was engineered with the DsRed marker gene under the control of the constitutively-expressed cassava mosaic virus promoter for selection of transgenic seeds by fluorescence (Lu and Kang, 2008, Plant Cell Rep., 27:273-8). Similarly, *A. thaliana* DGAT1 was subcloned into the binary vector generating pBinGlyRed3_CvFatB1+AthDGAT1 for transformation into *Camelina*.

Example 17—Phylogenetic Analysis

An unrooted phylogenetic tree of CpDGAT1 deduced amino acid sequence along with other amino acid sequences homologous to DGAT1 or DGAT2 including several functionally characterized ones was constructed. The functional and phylogenetic relationships were identified by the neighbor joining program in MEGA4 (Tamura et al., 2007, Mol. Biol. Evol., 24:1596-9). The bootstrap analysis was performed with 1,000 replicates.

Example 18—Yeast Transformation and Selection

The constructs pYes2_CpDGAT1, pYes2_CpDGAT1Ala, and pYes2_CpDGAT1trunc were transformed into *S. cerevisiae* strain H1246 (W303; MATα are1-Δ::HIS3 are2-Δ:: LEU2 dga1::KanMX4 lro1-Δ::TRP1 ADE2 met ura3) (Sandager et al., 2002, J. Biol. Chem., 277:6478-82) using PEG/lithium acetate method (Gietz et al., 1995, Yeast, 11:355-60). The yeast cells harboring the empty pYes2 vector were used as negative control. Transformants were selected by uracil prototrophy on yeast synthetic medium (YSM) containing 2% (w/v) glucose and lacking uracil (Invitrogen, Carlsbad, Calif. USA). For functional expression YSM containing 2% (w/v) raffinose was inoculated with the yeast transformants and grown at 28° C. for 24 h in a shaker at 350 rpm. For induction, YSM containing 2% (w/v) galactose was inoculated with raffinose-grown cultures to obtain an OD of 0.2 at 600 nm and grown at 28° C. for 48 h. For fatty acid feeding experiments cultures were grown for 2.5 hs in YSM containing 2% galactose followed by addition of 1% (w/v) Tergitol-40 and 250 μM of the appropriate fatty acid substrate. Cells were harvested by centrifugation, washed twice with 0.1% NaHCO3, freeze-dried and used for fatty acid, TAG analysis and microsome isolation.

Example 19—*Camelina* Transformation and Selection

The binary vector containing a cassette for seed specific expression of CpDGAT1, CpDGAT1trunc or AthDGAT1 was introduced into *Agrobacterium tumefaciens* by electroporation. Transgenic plants were generated by floral dip of *Camelina* wt plants (Lu and Kang, 2008, Plant Cell Reports, 27:273-8). Transgenic seeds among mature seeds were selected using DsRed marker and were also PCR confirmed. Expression of transgenes in developing seeds was confirmed by RT-PCR.

Example 20—TAG Quantification and FA Profiling

Total lipid extraction by Bligh Dyer: 30 mg of *Camelina* seeds was weighed in glass test tubes, followed by addition of 270 μl (10 mg/ml) C17-TAG and 50 μl (1 mg/ml) C17-PC. Seeds were crushed in 3 ml methanol: chloroform (2:1 v/v) by grinding with a grinder and incubated for 1 h at room temperature with agitation. Extraction was continued by adding 1 ml of chloroform and 1.9 ml of water to a test tube and vortexed, centrifuged at 4000 rpm for 10 minutes. The organic (lower) phase was transferred to a new test tube, 400 μl was saved for transesterification. The rest was used for separation of TAG, DAG and Polar lipids using Supelco Supel Clean LC-Si SPE (Sigma) columns. Dried total lipids were redissolved in 1 ml of heptane and loaded onto LC-Si SPE columns equilibrated according to manufacturer's guidelines, once the sample ran through the column first wax esters were eluted with 1.5 ml of 95:5 heptane: ethyl ether, second TAG fraction was eluted with 5 ml of heptane: ethyl ether 80:20 (v/v). DAG was eluted with 3 ml chloroform: acetone 80:20 (v/v). Columns were washed with 6 ml of acetone followed by elution of phospholipids with 5 ml methanol:chloroform:water 100:50:40 (v/v/v). Total phospholipids were pooled with addition of 1.33 ml chloroform and 1.31 ml water followed by vortexing and centrifugation at 4000 rpm for 10 minutes. The organic phase containing total phospholipids was transferred into a new tube.

600 μl of polar lipid fraction was dried and transesterified the rest was redessolved in 100 μl chloroform and separated by TLC in a solvent system consisting of CHCl3:MeOH: H2O:30% ammonium hydroxide (65:35:3:2.5 v/v/v/v). Bands from the TLC plates corresponding to PC were scraped onto wax paper and transferred to 13×100 mm test tubes. Transesterification of total lipids, TAG, and phospholipid fractions was done in 1 ml of 2% sulphuric acid in methanol by heating at 90° C. for 30 min. Upon cooling the samples to room temperature 1 ml H2O and 1 ml heptane was added followed by vortexing and centrifuging. Heptane layer was transferred to GC vials and analyzed in GC.

Example 21—Isolation of *C. pulcherrima* DGAT1 and DGAT2 Genes

Potential genes identified as DGATs were blasted against *A. thaliana* gene database in TAIR BLAST 2.2.8. The blast identified one gene model highly similar to *A. thaliana* DGAT1 thus named CpDGAT1. In addition three genes two of which are similar to *R. communis*, *V. fordii* DGAT2 were identified and designated as CpDGAT2_A and CpDGAT2_C, the third one is similar to *A. thaliana* DGAT2 and was named CpDGAT2_B. The ORF of CpDGAT1 is 1482 bp encoding a 484 amino acid polypeptide (Altschul et al., 1997, Nucl. Acids Res., 25:3389-402). Homology search blast analysis of 484 deduced amino acid showed it being most identical, 59 and 54%, to functionally characterized DGAT1s from *A. thaliana* and *B. napus*, respectively, while it shares ~39% identity with mammalian DGAT1s (FIG. 11). The N terminus 78 amino acids has no sequence homology in other known homologous DGAT1s (FIG. 12), the hydrophilic N-terminus of 151 and 80 residues in plants and animals, respectively, were found to be unique for every DGAT1. Nevertheless, the rest is highly conserved and identical to DGAT1s from plant species such as *A. thaliana*, *B. napus*, *R. communis* and *O. sativa* (FIG. 12). The SOSUI secondary structure prediction program predicted ten transmembrane regions in CpDGAT1. Similarly 8-10 hydrophobic regions were identified in DGAT1s of different origins (Liu et al., 2012, Plant Biotechnol. J., 10:862-70). The average number of residues is higher for DGAT1s than that of DGAT2s corresponding to 20 kDa difference in molecular mass. Expression of CpDGAT1 in H1246 mutant, which contains disruptions of four acyltransferase genes that contribute to TAG synthesis, did not store TAG biosynthesis to the *S. cerevisiae* while AthDGAT1 expressing H1246 yeast cells make TAG. Expression of codon optimized CpDGAT1 in H1246 yeast cells did not lead to any differences. Similarly, DGAT assay using radiolabelled 10:0 and DAG 10:0/10:0 substrates with microsomes from CpDGAT1 expressing yeast cells did not result in formation of TAG.

Example 22—Tissue-Specific Expression of *C. pulcherrima* DGATs

Expression profile of CpDGAT1, CpDGAT2_A, CpDGAT2_B and CpDGAT2_C in root, stem, leaf, flower and developing seeds of *C. pulcherrima* was analyzed (FIG. 13). The transcript abundance of the genes was normalized to that of *C. pulcherrima* eukaryotic initiation factor and actin (CpeIF4 and CpActin) genes. It was found that CpDGAT1 is specifically expressed in developing seeds. The three *C. pulcherrima* DGAT2 genes expression was observed in all tissues, stronger expression of CpDGAT2_A, CpDGAT2_B can be seen in developing seeds while CpDGAT2_C is expressed at similar levels in all tissues analyzed.

Example 23—Seed-Specific Expression of CpDGAT1 and CvLPAT2 Enhances Decanoic Acid and Caprylic Acid Content in *Camelina sativa* Seeds CpDGAT1 was expressed under seed specific glycinin-1 promoter along with the *C. viscosissima* thioesterase (Cv-FatB1), known to be specific for C10:0, C12:0, C14:0 and C16:0 Acyl-ACP. CvLPAT2 the ORF of 1155 bp was amplified from a cDNA prepared from total RNA from *C. viscosissima* from developing seeds. It was cloned into pBinGlyred vector under glycinin-1 promoter.

Analysis of seeds from T2 plants of 24 independent lines expressing CvFatB1+CpDGAT1 and CvFatB1+CvLPAT2+CpDGAT1, as confirmed by reverse-transcription PCR, showed increased amounts of 10:0 (FIGS. 14 and 15). The 10:0 fatty acid levels in transgenic CvFatB1+CpDGAT1 and CvFatB1+CvLPAT2+CpDGAT1 T2 seeds reached as high as 13.5 and 21.5 mol % of TFA as compared to 8.0 mol % in lines expressing only CvFatB1, while that of C12:0, C14:0 and C16:0 stayed similar (FIGS. 14 and 15). Significant decrease in the amounts of 18:2, 18:3 and 20:1 by 10, 18 and 6 mol %, respectively, was seen in all CvFatB1+CpDGAT1 transgenic lines. The oil content in seeds from T3 homozygous transgenic lines from CvFatB1+CpDGAT1 (FIG. 14) and CvFatB1+CvLPAT2+CpDGAT1 (FIG. 15), which had the highest amounts of 10:0, was not significantly affected. In addition to C10:0, 3 to 5 mol % of C8:0 was detected in TAG in the seeds engineered to express CvFatB1+CvLPAT2+CpDGAT1.

Example 24—Enhanced Amounts of C8:0 and C10:0 are Detected at Sn-2 Position of TAG from Seeds of Transgenic *Camelina* Lines Expressing CvLPAT2 or/and CpDGAT1

Stereospecific analysis of fatty acid species at sn-2 position of TAG from engineered seeds was conducted to assess the efficiency of assembly of short and medium chain fatty acids in TAG. Fatty acid profile of sn-2 monoacylglycerol obtained by digesting with TAG sn-1 and sn-3 specific lipase from *Rhizomucor miehei* (Sigma) revealed that while trace amounts of 10:0 is seen at sn-2 position of TAG from seeds of CvFatB1+CpDGAT1 lines, there is a striking increase up to 20 mol % in CvFatB1+CvLPAT2 line and 33.1 mol % in the relative content of 10:0 at sn-2 of TAG from CvFatB1+CvLPAT2+CpDGAT1 line was observed (FIG. 17). In addition to C10:0, 3 to 5 mol % of C8:0 was detected in TAG sn-2 position in the seeds engineered to express CvFatB1+CvLPAT2+CpDGAT1.

The increase of 10:0 at the sn-2 position of TAG from CvFatB1 expressing lines is accompanied by reduction of 18:2 and significantly that of 18:3 which is 17.4 mol % as compared to 44.3 mol % at this position in TAG from Wt camelina seeds. In *C. pulcherrima* fatty acid species at sn-2 position of TAG are 8:0 (up to 97 mol %) and C10:0 (3 mol %) while in *C. viscosissima* it is 12.6 mol % of C8:0 and 87.4 mol % of 10:0 (FIG. 17).

Example 25—DAG Species from *C. sativa* Transgenic Lines Overexpressing *Cuphea* Species Acyltransferases Contain Increased Amounts of Shorter Chain Saturated Fatty Acids Fatty acid profile of DAG species from the transgenic lines was analyzed (FIG. 18). The data showed higher amounts of C10:0 and C16:0 fatty acids in lines expressing the *Cuphea* acyltransferases CvLPAT2 and CpDGAT1 in addition to the thioesterase, CvFatB1. The seeds of CvFatB1 expressing lines contain ~4 mol % of C10:0, ~12 mol % of C16:0, while that of CvFatB1+CpDGAT1 and CvFatB1+CvLPAT2 contain up to 8 mol % of C10:0, 3 mol % of C14:0 and 20 mol % of C16:0. DAG species from CvFatB1+CvLPAT2+CpDGAT1 contain highest amount of C10:0 up to 14 mol %. The increase in the amounts of short and medium chain fatty acids in DAG species is accompanied by substantial decrease of 18:3. DAGs from developing seeds of *C. viscosissima* contain up to 12, 53, 8 and 32 mol % of C8:0, C10:0, C14:0 and C16:0, respectively.

Example 26—Accumulation of Short- and Medium-Chain Fatty Acids in Transgenic *Camelina* Lines Starts at Midstage in Developing Seeds Fatty acid composition of developing seeds from transgenic *Camelina* lines were analyzed at four stages after flowering: 10 DAF, 17 DAF, 22DAF and 30 DAF. Ten day developing seeds contain very low 10:0 (~2.5 mol %), main fatty acids are 16:0 (~14 mol %), 18:1 (20 mol %), 18:2 (40-44 mol %), and 18:3 (18-20 mol %), the predominant one. The percent share of each fatty acid (C16:0 through 20:1) in TFA in transgenic lines is similar to that of wild type *Camelina* plants. 17 day seeds produce more of shorter chain fatty acids 8:0 (4 mol %), 10:0 (up to 24 mol %), 12:0 (2.5-4 mol %), 14:0 (3 mol %) and higher amounts of 16:0 (13 mol %) in transgenic lines. In CvFatB1+CvLpat2+CpDGAT1 the amount of 18:1 decreases, while 18:2, 18:3 and 20:1 make 15 mol %, 16 mol % and 6 mol %, respectively, as compared to 21.4, 30 and 12.7 mol % in wild type *Camelina* plants.

22 day seeds produce more of short chain fatty acids 5 mol % C8:0, 30 mol % 10:0, 7 mol % (12:0-14:0). The amounts of 16:0, 18:0, 18:1, 18:2, 18:3 and 20:1 in CvFatB1+CvLPAT2+CpDGAT1 line are 12, 8, 12, 16, and 5 mol % as compared to 8, 13, 20, 41, and 10 mol % in seeds of wild type plants. Thus the share of 8:0 through 16:0 fatty acids total amount in this line reaches 54 mol % of TFA as compared to 39 mol % in CvFatB1 line, 43% in CvFatB1+CpDGAT1 line and 8 mol % in wild type.

In 30 days in seeds from CvFatB1 line there is 33.6 mol % of 8:0-16:0, 22.4 mol % 18:1, 13.7 mol % 18:2, 16.0 mol % 18:3 and 6.6 mol % 20:1. CvFatB1+CpDGAT1 transgenic lines accumulate more 10:0, and 8:0-10:0 total fatty acids amount is 37.5 mol % while amounts of 18:1, 18:2, 18:3 and 20:1 are similar to what is found in seeds from CvFatB1 line. In CvFatB1+CvLPAT2+CpDGAT1 line the average share of 8:0-16:0 fatty acids is 43 mol % of TFA, 18.5 mol % being 10:0 and 13.2 mol % 18:1, 12.8 mol % 18:2, 18.3 mol % 18:3, 6.3 mol % 20:1.

As seeds develop oil content increases in both wild type and transgenic *Camelina* lines. Major oil accumulation started in 17 days at which oil content doubled 26.5% as compared to 13% of dry weight in 10 days, followed by 33.4% and 28%, after 22 and 30 days, respectively, in wild type. In CvFatB1+CvLPAT2+CpDGAT1 lines average oil content was 13%, 26%, 30% and 22.7%, as compared to thioesterase only expressing lines 11.8, 23.0, 24.6, and 23.4%, in 10, 17, 22 and 30 days, respectively.

Example 27—CpDGAT1 has Preference for 10:0 Containing Substrates and Decanoyl CoA Substrate preferences of CpDGAT1 were tested using extracts from 22 day developing seeds of CvFATB1, CvFatB1+CpDGAT1, and CvFatB1+CvLPAT2+CpDGAT1 (FIG. 20). Acyl-CoA dependent DGAT activity was examined by measuring the incorporation of [$^{14}$C] acyl-CoA into DAG acceptors 10:0/10:0 (1,2-didecanoyl-sn-glycerol) or 18:1/18:1 (1,2-dioleoyl-sn-glycerol). In seed extracts of CpDGAT1 expressing lines TAG formation from 1,2-DAG 10:0/10:0 and 10:0-CoA was enhanced. DGAT activity with 1,2-DAG 10:0/10:0 and 10:0-CoA was similar 80.6±4.1 and 63.6±23.4 pmol TAG/min/g protein in Wt and CvFatB1 expressing line, respectively. In CvFatB1+CpDGAT1 and CvFatB1+CvLPAT2+CpDGAT1 lines the activity was 346±77.5 and 323±57.9 pmol TAG/min/g protein, respectively.

Example 28—Germination Efficiency of Short- and Medium-Chain Fatty Acid Rich Transgenic *Camelina* Seeds High levels of short and medium chain fatty acids did not affect average seed weight observed for transgenic seeds obtained in greenhouse conditions (FIG. 20). The weight of 100 seeds from wild type *Camelina* was 79 mg, 74 mg for CvFatB1, 71 and 77 mg for CvFatB1+CpDGAT1, and CvFatB1+CvLPAT2+CpDGAT1 lines, respectively.

Germination efficiency of homozygous 10:0-16:0 rich transgenic *Camelina* seeds was not significantly affected by high levels of 10:0 or increased amounts of 16:0 (FIG. 22). Up to 93% of seeds from CvFatB1 line germinated in 10 days in greenhouse conditions, for CvFatB1+CpDGAT1 it was 78% and 97% for CvFatB1+CvLPAT2+CpDGAT1, which contains highest amounts of short and medium chain fatty acids.

Example 29—Seed-Specific Expression of CpDGAT1 and CvLPAT2a Further Enhances Decanoic Acid Content in *Camelina sativa* Seeds CpDGAT1 was expressed under seed specific glycinin-1 promoter along with the *C. viscosissima* thioesterase (CvFatB1), known to be specific for C8:0 and C10:0 Acyl-ACP. The CpuPAT2a ORF of 1164 bp was amplified from cDNA prepared from total RNA from *C. pulcherrima* developing seeds and was sub-cloned into pKMS3 vector under glycinin-1 promoters. A cassette comprising the glycinin-1 promoter and CpuLPAT2a gene was inserted into the pBinGlyRed-CvFatB1+CpDGAT1 to make the pBinGlyRed-CvFatB1+CpuLPAT2a+CpDGAT1.

Analysis of seeds from T2 lines expressing CvFatB1+CvLPAT2+CpDGAT1 and T3 lines expressing CvFatB1+CpuLPAT2a+CpDGAT1 showed increased amounts of 10:0 in TAG (FIGS. 16 and 24). The 10:0 fatty acid levels in transgenic CvFatB1+CvLPAT2a+CpDGAT1 T3 seeds reached as high as 18.5 and 27 mol % of TAG TFA as compared to 8.0 mol % in lines expressing only CvFatB1, while that of C18:1, C18:2 and C18:3 stayed similar (FIGS. 16 and 24). The oil content in seeds from T3 transgenic lines from CvFatB1+CvLPAT2+CpDGAT1 (7,11), which had high amounts of 10:0, was not significantly affected (FIG. 24A). The amount of C10:0 is even higher in seeds of *Camelina* lines expressing CpuLPAT2a in addition to CvFatB1 and CpDGAT1 (CvFatB1+CpuLPAT2a+CpDGAT1). Fatty acid profile of sn-2 monoacylglycerol obtained by digesting with TAG sn-1 and sn-3 specific lipase from *Rhizomucor miehei* (Sigma) indicated a significant increase in 10:0 at sn-2 position of TAG from seeds of both CvFatB1+CvLPAT2+CpDGAT1 (FIG. 17) and CvFatB1+CpuLPAT2a+CpDGAT1 (FIG. 24B) lines. It is notable also that 8:0 was detected in amounts of ~3 mol % in the total TAG and in the TAG sn-2 position in seeds engineered to express CvFatB1+CvLPAT2CpuLPAT2a+CpDGAT1.

TABLE 1

Primers used for cloning CpDGAT1 and AthDGAT1 into yeast and Camelina expression vectors
*C. pulcherrima* primers used for expression in yeast and Camelina

| | | |
|---|---|---|
| CpDGAT1BamHIf | CTAGGATCCAccATGgctCATGAGGCAGTCAG (SEQ ID NO: 49) | HisBamHI |

TABLE 1-continued

Primers used for cloning CpDGAT1 and AthDGAT1 into yeast and Camelina expression vectors
C. pulcherrima primers used for expression in yeast and Camelina

| | | |
|---|---|---|
| CpDGAT1AlaBamHIf | CTAGGATCCAccATGgctGAGGCAGTCAGC (SEQ ID NO: 50) | BamHI |
| CpDgat1trunc_BamH1f | GTCGGATCCAccATGGCTCACCGGACTTCA (SEQ ID NO: 51) | BamHI |
| CpDGAT1XbaIr | ATATCTAGACTAGTCGATCCTTAATCCTC (SEQ ID NO: 52) | XbaIr |
| CpDG1not1F | ATAgcggccgcATGCATGAGGCAGTCAG (SEQ ID NO: 53) | BamH1 |
| CpDg1trF_Not1 | ATAgcggccgcATGGCTCACCGGACTTCA (SEQ ID NO: 54) | NotI |
| CpDg1R_Not1 | AATGCGGCCGCCTAGTCGATCCTTAAT (SEQ ID NO: 55) | NotI |

TABLE 2

Primers used for SQRT-PCR of CpDGAT1, CpDGAT2_A, CpDGAT2_B, and CpDGAT2_C

| Gene name | Primer name | Primer sequence 5'-3' Forward/Reverse | Amplicon size (bp) |
|---|---|---|---|
| CpDGAT1 | SQCpDG1f | CTTCAATCTCTGTATGGTCACTCTC (SEQ ID NO: 66)/ | 298 |
| | SQCpDG1r | GACATCAAGGCACAATCAAATCTC (SEQ ID NO: 67) | |
| CpDGAT2_A | Cp1DGsqf | GGAGATTCGCGAGGAGCTTAAGTAGG (SEQ ID NO: 68)/ | 347 |
| | Cp1DGsqr | CATATGGAATGTCTCCTGCACACCAC (SEQ ID NO: 69) | |
| CpDGAT2_B | CPDG2_2_sqF | GAGCGAGATGCTGAGATTGTGTTCCT (SEQ ID NO: 70)/ | 308 |
| | CPDG2_2_sqR | TCACTGTGCACCTCATTCACCTCTTC (SEQ ID NO: 71) | |
| CpDGAT2_C | CpDG2_3hinsq_F | TGGTGTGCAGGAGACATTCTACATGG/ (SEQ ID NO: 72) | 381 |
| | CpDG2_3xbsq_R | ACTTGTGCCTTGTGTCGCTCGAATAG (SEQ ID NO: 73) | |
| CpActin | CpACTf | TTGCTTTGGACTACGAGCAGGAGA/ (SEQ ID NO: 74) | 189 |
| | CpACTr | TGGAGTTGTAAGTCGTCTCGTGGA (SEQ ID NO: 75) | |
| CpeIF4 | CpeIF4_RT_F | GGTGAAGCGTGACGAACTGAC/ (SEQ ID NO: 76) | 140 |
| | CpeIF4_RT_R | CTCTAGTGTTCTGGTCCATGTCTCC (SEQ ID NO: 77) | |

Primers used for expression of CpDGAT2 genes in yeast

| | | |
|---|---|---|
| Cpdg1 | CTAGGATCCAccATGCGGGAGGAGACGAA (SEQ ID NO: 56) | BamHI |
| Cpdg2 | atatctagaTCAAAGGATTCTCAGTTTGA (SEQ ID NO: 57) | XbaI |
| Cpdg3 | CTAGGATCCAccATGATAGGGTTCaATGA (SEQ ID NO: 58) | BamHI |
| Cpdg4 | atatctagaTCACAAAATTCTCAGTTCGA (SEQ ID NO: 59) | XbaI |
| Cpdg5 | ctaAAGCTTAccATGGGAGAGGAGGCGGAC (SEQ ID NO: 60) | HindIII |
| Cpdg6 | atactcgagTTAAAGTATTCTCAGTTTGA (SEQ ID NO: 61) | XhoI |

A. thaliana DGAT1 primers used for cloning into yeast and Camelina transformation

| | | |
|---|---|---|
| AthBamHIDGAT1F | CTAGGATCCAccATGGCGATTTGGATTC (SEQ ID NO: 62) | BamHI |
| AthXbaIDGAT1R | ATATCTAGATCATGACATCGATCCTTTTC (SEQ ID NO: 63) | XbaI |

TABLE 2-continued

Primers used for SQRT-PCR of CpDGAT1, CpDGAT2_A, CpDGAT2_B, and CpDGAT2_C

| Gene name | Primer name | Primer sequence 5'-3'<br>Forward/Reverse | Amplicon size (bp) |
|---|---|---|---|
| AthNotIf | | ATAgcggccgcATGGCGATTTTGGATT<br>(SEQ ID NO: 64) | NotIf |
| AthNotIr | | TATGCGGCCGCTCATGACATCGATCCTTT<br>(SEQ ID NO: 65) | NotIr |

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of producing triacylglycerols (TAGs) comprising medium-chain fatty acids (MCFAs) in an organism, said method comprising:
   introducing a first transgene into the organism, wherein the first transgene comprises at least one nucleic acid sequence encoding a lysophosphatidic acid acyltransferase (LPAT) that exhibits a substrate specificity for saturated fatty acids, wherein the nucleic acid sequence encoding the LPAT has at least 95% sequence identity to SEQ ID NO: 1 or SEQ ID NO: 3; and
   introducing a second transgene into the organism, wherein the second transgene comprises at least one nucleic acid sequence encoding a diacylglycerol acyltransferase (DGAT) that exhibits a substrate specificity for saturated fatty acids, wherein the nucleic acid sequence encoding the DGAT has at least 95% sequence identity to SEQ ID NO: 7 or SEQ ID NO: 9, thereby producing TAGs comprising MCFAs in the organism, wherein the organism is a plant or a microbe.

2. The method of claim 1, wherein at least 20% of the TAGs comprising MCFAs have a C8:0 or a C10:0 at sn-2 position.

3. The method of claim 1, wherein the saturated fatty acids are selected from the group consisting of C8:0 and C10:0.

4. The method of claim 1, wherein the nucleic acid sequence encoding the LPAT is a sequence having at least 95% sequence identity to SEQ ID NO:1.

5. The method of claim 1 wherein the nucleic acid sequence encoding the DGAT is a sequence having at least 95% sequence identity to SEQ ID NO:7.

6. The method of claim 1, wherein the organism further comprises a nucleic acid sequence encoding a medium-chain fatty acid (MCFA)-specific thioesterase FatB.

7. The method of claim 6, wherein the nucleic acid sequence encoding the MCFA-specific thioesterase FatB is selected from the group consisting of a nucleic acid sequence having at least 95% sequence identity to SEQ ID NO:11, a nucleic acid sequence having at least 95% sequence identity to SEQ ID NO:13, and a nucleic acid sequence having at least 95% sequence identity to SEQ ID NO:15.

8. The method of claim 1, wherein the organism is a plant, and wherein the plant is Camelina sativa.

9. The method of claim 1, wherein the first transgene and the second transgene each comprises a promoter.

10. The method of claim 9, wherein the organism is a plant, and wherein each promoter is a seed-specific promoter.

11. The method of claim 1, wherein the at least one nucleic acid sequence encoding a LPAT is operably linked to a seed-specific promoter, and wherein the at least one nucleic acid sequence encoding a DGAT is operably linked to a seed-specific promoter.

12. The method of claim 11, wherein the medium-chain fatty acids are produced in the seed.

13. The method of claim 1, wherein the introducing step is performed using Agrobacterium transformation, particle bombardment, or electroporation of protoplasts.

14. A method of producing triacylglycerols (TAGs) comprising medium-chain fatty acids (MCFAs), comprising:
    providing an organism comprising a first and a second transgene, wherein the organism is a plant or a microbe, wherein the first transgene comprises at least one nucleic acid sequence encoding a lysophosphatidic acid acyltransferase (LPAT) that exhibits a substrate specificity for saturated fatty acids, wherein the nucleic acid sequence encoding the LPAT has at least 95% sequence identity to SEQ ID NO:1 or SEQ ID NO:3,
    wherein the second transgene comprises at least one nucleic acid sequence encoding a diacylglycerol acyltransferase (DGAT) that exhibits a substrate specificity for saturated fatty acids, wherein the nucleic acid sequence encoding the DGAT has at least 95% sequence identity to SEQ ID NO:7 or SEQ ID NO:9;
    growing the organism under appropriate conditions; and
    obtaining TAGs comprising MCFAs from the organism.

15. The method of claim 14, wherein the TAGs are used in biofuel, jet fuel, detergents, and chemical feedstocks.

* * * * *

SEQUENCE LISTING

```
<160> NUMBER OF SEQ ID NOS: 77

<210> SEQ ID NO 1
<211> LENGTH: 1155
<212> TYPE: DNA
<213> ORGANISM: Cuphea viscosissima

<400> SEQUENCE: 1
atggcgattg cagcggcagc tgtcatcttc ctcttcggcc ttatcttctt cgcctccggc      60
ctcattatca atctcttcca ggcgctttgc tttgtcctta ttcggcctct ttcgaaaaac     120
gcctaccgga gaataaacag agtttttgca gaattgttgt tgtcggagct tttatgccta     180
ttcgattggt gggctggtgc taagctcaaa ttatttaccg accctgaaac cttctcgcctt    240 atgggcaagg aacatgctct ggtcataatt aatcacatga ctgaacttga ctggatggtt     300
ggatgggtta tgggtcagca ttttggttgc cttgggagca taatatctgt tgcgaagaaa     360
tcaacaaaat ttcttccggt attggggtgg tcaatgtggt tttcagagta cctatatctt     420
gagagaagct gggccaagga taaaagtaca ttaaagtcac atatcgagag gctgatagac     480
taccccctgc ccttctggtt ggtaattttt gtggaaggaa ctcggtttac tcggacaaaa     540
ctcttggcag cccagcagta tgctgtctca tctgggctac cagtgccgag aaatgttttg     600
atcccacgta ctaagggttt tgtttcatgt gtgagtcaca tgcgatcatt tgttccagca     660
gtatatgatg tcacagtggc attccctaag acttcacctc caccaacgtt gctaaatctt     720
ttcgagggtc agtccataat gcttcatgtt cacatcaagc gacatgcaat gaaagattta     780
ccagaatccg atgatgcagt agcagagtgg tgtagagaca aatttgtgga aaaggatgct     840
ttgttggaca agcataatgc tgaggacact ttcagtggtc aagaagttcg tcataccggc     900
agccgccagt taagtctctc tctggtggta atatcttggg tggttgtaac aacatttggg     960
gctctaaagt tccttcagtg gtcatcatgg aaggggaaag cattttcagc tatcgggctg    1020
```

```
ggcatcgtca ctctacttat gcacgtattg attctatcct cacaagcaga gcggtccaac      1080
cctgcggagg tggcacaggc aaagctaaag accgggttgt cgatctcaaa gaaggtaacg      1140
gacaaggaaa actag                                                       1155
```

<210> SEQ ID NO 2
<211> LENGTH: 384
<212> TYPE: PRT
<213> ORGANISM: Cuphea viscosissima

<400> SEQUENCE: 2

```
Met Ala Ile Ala Ala Ala Val Ile Phe Leu Phe Gly Leu Ile Phe
1               5                   10                  15

Phe Ala Ser Gly Leu Ile Ile Asn Leu Phe Gln Ala Leu Cys Phe Val
            20                  25                  30

Leu Ile Arg Pro Leu Ser Lys Asn Ala Tyr Arg Arg Ile Asn Arg Val
        35                  40                  45

Phe Ala Glu Leu Leu Leu Ser Glu Leu Leu Cys Leu Phe Asp Trp Trp
50                  55                  60

Ala Gly Ala Lys Leu Lys Leu Phe Thr Asp Pro Glu Thr Phe Arg Leu
65                  70                  75                  80

Met Gly Lys Glu His Ala Leu Val Ile Ile Asn His Met Thr Glu Leu
                85                  90                  95

Asp Trp Met Val Gly Trp Val Met Gly Gln His Phe Gly Cys Leu Gly
            100                 105                 110

Ser Ile Ile Ser Val Ala Lys Lys Ser Thr Lys Phe Leu Pro Val Leu
        115                 120                 125

Gly Trp Ser Met Trp Phe Ser Glu Tyr Leu Tyr Leu Glu Arg Ser Trp
    130                 135                 140

Ala Lys Asp Lys Ser Thr Leu Lys Ser His Ile Glu Arg Leu Ile Asp
145                 150                 155                 160

Tyr Pro Leu Pro Phe Trp Leu Val Ile Phe Val Glu Gly Thr Arg Phe
                165                 170                 175

Thr Arg Thr Lys Leu Leu Ala Ala Gln Gln Tyr Ala Val Ser Ser Gly
            180                 185                 190

Leu Pro Val Pro Arg Asn Val Leu Ile Pro Arg Thr Lys Gly Phe Val
        195                 200                 205

Ser Cys Val Ser His Met Arg Ser Phe Val Pro Ala Val Tyr Asp Val
    210                 215                 220

Thr Val Ala Phe Pro Lys Thr Ser Pro Pro Thr Leu Leu Asn Leu
225                 230                 235                 240

Phe Glu Gly Gln Ser Ile Met Leu His Val His Ile Lys Arg His Ala
                245                 250                 255

Met Lys Asp Leu Pro Glu Ser Asp Asp Ala Val Ala Glu Trp Cys Arg
            260                 265                 270

Asp Lys Phe Val Glu Lys Asp Ala Leu Leu Asp Lys His Asn Ala Glu
        275                 280                 285

Asp Thr Phe Ser Gly Gln Glu Val Arg His Thr Gly Ser Arg Gln Leu
    290                 295                 300

Lys Ser Leu Leu Val Val Ile Ser Trp Val Val Thr Thr Phe Gly
305                 310                 315                 320

Ala Leu Lys Phe Leu Gln Trp Ser Ser Trp Lys Gly Lys Ala Phe Ser
                325                 330                 335

Ala Ile Gly Leu Gly Ile Val Thr Leu Leu Met His Val Leu Ile Leu
            340                 345                 350
```

```
Ser Ser Gln Ala Glu Arg Ser Asn Pro Ala Glu Val Ala Gln Ala Lys
        355                 360                 365

Leu Lys Thr Gly Leu Ser Ile Ser Lys Lys Val Thr Asp Lys Glu Asn
    370                 375                 380

<210> SEQ ID NO 3
<211> LENGTH: 1164
<212> TYPE: DNA
<213> ORGANISM: Cuphea pulcherrima

<400> SEQUENCE: 3
atgacgattg catcggcagc tgtcgtcttt ctgttcggca ttctcctctt cacctccggc      60
ctcattatca atctcttcca ggcgttttgc tctgtccttg tttggcctct ttcgaagaac     120
gcctaccgga gaattaaccg agttttttgca gaatttttgc ccttggagtt tttatggcta     180
ttccattggt gggctggtgc taagctcaaa ttatttaccg accctgaaac ctttcgcctt     240
atgggcaagg aacatgctct tgtcataatt aatcacaaga ttgagcttga ctggatggtt     300
ggatgggttc tgggtcagca tttaggttgc cttgggagca tattatccgt tgcgaagaaa     360
tcaacaaaat ttcttccggt ttttgggtgg tcattatggt tttcagagta tctatttctt     420
gagagaaact gggccaagga taaaaaaaca ttaaagtcac atatagagag gctgaaagat     480
tacccccctgc cctctggtt gataattttt gtggaaggaa ctcggtttac tcggacaaaa     540
ctcttggcag cccagcagta tgctgcctca gctgggttac cagtgccgag aaatgttttg     600
atcccacata ctaagggttt tgtttcatct gtgagtcaca tgcgatcatt tgttccggca     660
atatacgatg tcacggtggc attccctaag acttcacctc caccaacgat gctaaaactt     720
ttcgagggtc attccgtaga gcttcacgtt cacatcaagc ggcatgcaat gaaagattta     780
ccagaatccg aagatgcagt agcacagtgg tgtagagaca aatttgttga aaggatgct      840
ttgttggaca gcataatgc tgaggacact ttcagtggtc aagaagttca tcatgtcggc     900
cgcccgataa agtctcttct ggtggtaata tcgtgggtgg ttgtaataat atttggggct     960
ctaaagttcc ttcagtggtc atcactctta tcatcatgga aggggaaagc attttcagtt    1020
atcgggttgg gcactgtcgc actactcatg caaatattga ttctatcctc acaagcagag    1080
cggtctatcc ctgccaagga gacaccggca atctaaaaga ccgagttgtc gtcctcaaag    1140
aaggtaacga acaaggaaaa ctag                                           1164

<210> SEQ ID NO 4
<211> LENGTH: 387
<212> TYPE: PRT
<213> ORGANISM: Cuphea pulcherrima

<400> SEQUENCE: 4

Met Thr Ile Ala Ser Ala Ala Val Val Phe Leu Phe Gly Ile Leu Leu
1               5                   10                  15

Phe Thr Ser Gly Leu Ile Ile Asn Leu Phe Gln Ala Phe Cys Ser Val
            20                  25                  30

Leu Val Trp Pro Leu Ser Lys Asn Ala Tyr Arg Arg Ile Asn Arg Val
        35                  40                  45

Phe Ala Glu Phe Leu Pro Leu Glu Phe Leu Trp Leu Phe His Trp Trp
    50                  55                  60

Ala Gly Ala Lys Leu Lys Leu Phe Thr Asp Pro Glu Thr Phe Arg Leu
65                  70                  75                  80

Met Gly Lys Glu His Ala Leu Val Ile Ile Asn His Lys Ile Glu Leu
```

```
                    85                  90                  95
Asp Trp Met Val Gly Trp Val Leu Gly Gln His Leu Gly Cys Leu Gly
                100                 105                 110

Ser Ile Leu Ser Val Ala Lys Lys Ser Thr Lys Phe Leu Pro Val Phe
                115                 120                 125

Gly Trp Ser Leu Trp Phe Ser Glu Tyr Leu Phe Leu Glu Arg Asn Trp
            130                 135                 140

Ala Lys Asp Lys Lys Thr Leu Lys Ser His Ile Glu Arg Leu Lys Asp
145                 150                 155                 160

Tyr Pro Leu Pro Phe Trp Leu Ile Ile Phe Val Glu Gly Thr Arg Phe
                165                 170                 175

Thr Arg Thr Lys Leu Leu Ala Ala Gln Gln Tyr Ala Ala Ser Ala Gly
            180                 185                 190

Leu Pro Val Pro Arg Asn Val Leu Ile Pro His Thr Lys Gly Phe Val
                195                 200                 205

Ser Ser Val Ser His Met Arg Ser Phe Val Pro Ala Ile Tyr Asp Val
            210                 215                 220

Thr Val Ala Phe Pro Lys Thr Ser Pro Pro Thr Met Leu Lys Leu
225                 230                 235                 240

Phe Glu Gly His Ser Val Glu Leu His Val His Ile Lys Arg His Ala
                245                 250                 255

Met Lys Asp Leu Pro Glu Ser Glu Asp Ala Val Ala Gln Trp Cys Arg
            260                 265                 270

Asp Lys Phe Val Glu Lys Asp Ala Leu Leu Asp Lys His Asn Ala Glu
            275                 280                 285

Asp Thr Phe Ser Gly Gln Glu Val His His Val Gly Arg Pro Ile Lys
            290                 295                 300

Ser Leu Leu Val Val Ile Ser Trp Val Val Ile Ile Phe Gly Ala
305                 310                 315                 320

Leu Lys Phe Leu Gln Trp Ser Ser Leu Ser Ser Trp Lys Gly Lys
                325                 330                 335

Ala Phe Ser Val Ile Gly Leu Gly Thr Val Ala Leu Leu Met Gln Ile
                340                 345                 350

Leu Ile Leu Ser Ser Gln Ala Glu Arg Ser Ile Pro Ala Lys Glu Thr
            355                 360                 365

Pro Ala Asn Leu Lys Thr Glu Leu Ser Ser Ser Lys Lys Val Thr Asn
            370                 375                 380

Lys Glu Asn
385

<210> SEQ ID NO 5
<211> LENGTH: 927
<212> TYPE: DNA
<213> ORGANISM: Cuphea pulcherrima

<400> SEQUENCE: 5
atggcgagta tcggaatcag ctccttattg aagaacagga aactggagag ttctttcagc      60
actggctttg cgaaagattc gttcccgcat tcgcctgaaa agacgatgat tagggatgat    120
tccgaacata ggactataat agctgatggc ttgtctgtcg atgatgacga tggatggatg    180
gctgtgttga tatcgtgggc gaggctcgtt atgtgttttg tgttggtgtt gatcacgaca    240
tccatttgga ccttgatcat ggttattctt atcccgtggc catgcgagcg atcaaacaa    300 agcaacgtct tcggtcacgt ctcgggcaga atgctgatgt ggttattagg aaatcccgta    360
```

```
aagatcgaag gcgccgagca tgctaatgag agagctatct acatctgcaa tcatgcgtcg      420
cctctcgata tagttctcac catgtggttg acaccgaaag gcactgtctg tatcgcaaag      480
aaagagatcg tctggtaccc gctaattggg caactctatg cattggctgg tcatctccgt      540
atagatcgct cgaacccggt tgctgctatt caatctatga aggaggtagc tcgtgctgtc      600
gttaaaaacg acctgtcttt gatcatattt ccagagggca cccgtcgaa agacgggcga       660 ctccttccat tcaaaaaggg ctttgtgcac ttggctctgc agactcggcg ccccattgtc      720
ccgatcgtgt tgacaggaac ccacatggcg tggagaaagg gtagtttgca catcagaccg      780
acgcctctca ccgtgaagta cctcccgccg atagtaacca ccgactggac acccgataga     840
gtcgaagact acacaaagat gatccatgac atatacgtga atcatctgcc agagtctcag     900
cagcctctga ggcctaaaga aagctag                                          927
```

<210> SEQ ID NO 6
<211> LENGTH: 308
<212> TYPE: PRT
<213> ORGANISM: Cuphea pulcherrima

<400> SEQUENCE: 6

```
Met Ala Ser Ile Gly Ile Ser Ser Leu Leu Lys Asn Arg Lys Leu Glu
1               5                   10                  15

Ser Ser Phe Ser Thr Gly Phe Ala Lys Asp Ser Phe Pro His Ser Pro
            20                  25                  30

Glu Lys Thr Met Ile Arg Asp Asp Ser Glu His Arg Thr Ile Ile Ala
        35                  40                  45

Asp Gly Leu Ser Val Asp Asp Asp Gly Trp Met Ala Val Leu Ile
    50                  55                  60

Ser Trp Ala Arg Leu Val Met Cys Phe Val Leu Val Leu Ile Thr Thr
65                  70                  75                  80

Ser Ile Trp Thr Leu Ile Met Val Ile Leu Ile Pro Trp Pro Cys Glu
                85                  90                  95

Arg Ile Lys Gln Ser Asn Val Phe Gly His Val Ser Gly Arg Met Leu
            100                 105                 110

Met Trp Leu Leu Gly Asn Pro Val Lys Ile Glu Gly Ala Glu His Ala
        115                 120                 125

Asn Glu Arg Ala Ile Tyr Ile Cys Asn His Ala Ser Pro Leu Asp Ile
    130                 135                 140

Val Leu Thr Met Trp Leu Thr Pro Lys Gly Thr Val Cys Ile Ala Lys
145                 150                 155                 160

Lys Glu Ile Val Trp Tyr Pro Leu Ile Gly Gln Leu Tyr Ala Leu Ala
                165                 170                 175

Gly His Leu Arg Ile Asp Arg Ser Asn Pro Val Ala Ala Ile Gln Ser
            180                 185                 190

Met Lys Glu Val Ala Arg Ala Val Val Lys Asn Asp Leu Ser Leu Ile
        195                 200                 205

Ile Phe Pro Glu Gly Thr Arg Ser Lys Asp Gly Arg Leu Leu Pro Phe
    210                 215                 220

Lys Lys Gly Phe Val His Leu Ala Leu Gln Thr Arg Arg Pro Ile Val
225                 230                 235                 240

Pro Ile Val Leu Thr Gly Thr His Met Ala Trp Arg Lys Gly Ser Leu
                245                 250                 255

His Ile Arg Pro Thr Pro Leu Thr Val Lys Tyr Leu Pro Pro Ile Val
            260                 265                 270
```

```
Thr Thr Asp Trp Thr Pro Asp Arg Val Glu Asp Tyr Thr Lys Met Ile
        275                 280                 285

His Asp Ile Tyr Val Asn His Leu Pro Glu Ser Gln Gln Pro Leu Arg
    290                 295                 300

Pro Lys Glu Ser
305

<210> SEQ ID NO 7
<211> LENGTH: 1482
<212> TYPE: DNA
<213> ORGANISM: Cuphea pulcherrima

<400> SEQUENCE: 7
atgcatgagg cagtcagcca ttttctccac cgccacgccc cactctctct ctccggcttc      60
gccatggcga tcgtcagcgg cactctcggc gtcgcagcct cctccttcat ccccgactcc     120
gatcactcca ccacctctcc ttctctccgc aagcgcaact cctcttcact ttttcccaag     180
gcctcagaca cttcttctgt cgacggcaag gccgctcacc ggacttcatc tccggttcac     240
ttgaaactgg cagagagtcc tctcagctcg agaaatatct tcaagcagaa tcatgaaggt     300
ctcttcaatc tctgtatggt cactctcgtt gctgtcatca tccgactctt cctcgagaat     360
ctcctcaagt atggttggct aatgaagaga gacttttggt tgagtacgtt cacagcctgg     420
ccgctcttca tttgtagcct cggtcttccc attttccccc ttgcagcatt cgtagtcgag     480
aagttggccc agaagaatct tctgccggaa ccgattgttt tatgttctca tgtcattatc     540
acttcggcat ccgtccttta tcccgcactt gtaattctga gatttgattg tgccttgatg     600
tctggtatcg gtctgatgct ctattcttgc gctctttggt taaaattggt gtcctatgcg     660
cacacaagtt acgatatgag atgtgaggcc aagtctcgtc ttgagggaaa aagtagtgcg     720
gattcaaaaa atggagagct tccttaccgc gtaaacatca aagatcttgc gtacttcatg     780
gttgcaccga ccctatgtta ccagcttttcg tatcctcgca cacaatttat acgtaaattt     840
tgggtggctc gccaagtctt gaagttgata ttggtcaatg tagtaatggg attcatcatt     900
gaacaatata tgattcccgt tatgcataac tctaaacccc cacggcgggg atattggtta     960
catttcatcg agaaaatttt gaagcttgcg gttccaagta taggcctgtg gttttgcata    1020
ttctactcca tttttcatct ctggctgaat atagtggcgg agctcctccg ttttggcgat    1080
cgtgaatttt ataagagttg gtggaatgcc aagaatatgg aggagtactg gaagatgtgg    1140
aacatacctg ttcataggtg gatggttcga catttatacg gtccttgcat gaagagaaaa    1200
ttaccgaggt gggtcgcgat ttctatctca tttctcttgt ctgcagtgtt gcatgagatc    1260
tgtgtaagtg ttccatgcca tgtgttccag ctttgggcat tcaacggaat gatgcttcag    1320
attccgctgg tgttgagttc gaaaccctta caaaagaggt tcccaagctc taaggctggg    1380
aatgtattct tctggttctt gttttgtatc tatgccagc ctaattgtgt gcttatgtac    1440
taccacgcct tgatggaacg gagaggatta aggatcgact ag                      1482

<210> SEQ ID NO 8
<211> LENGTH: 493
<212> TYPE: PRT
<213> ORGANISM: Cuphea pulcherrima

<400> SEQUENCE: 8

Met His Glu Ala Val Ser His Phe Leu His Arg His Ala Pro Leu Ser
1               5                   10                  15

Leu Ser Gly Phe Ala Met Ala Ile Val Ser Gly Thr Leu Gly Val Ala
```

-continued

```
                20                  25                  30
Ala Ser Ser Phe Ile Pro Asp Ser Asp His Ser Thr Thr Ser Pro Ser
            35                  40                  45
Leu Arg Lys Arg Asn Ser Ser Leu Phe Pro Lys Ala Ser Asp Thr
    50                  55                  60
Ser Ser Val Asp Gly Lys Ala Ala His Arg Thr Ser Ser Pro Val His
65                  70                  75                  80
Leu Lys Leu Ala Glu Ser Pro Leu Ser Ser Arg Asn Ile Phe Lys Gln
                85                  90                  95
Asn His Glu Gly Leu Phe Asn Leu Cys Met Val Thr Leu Val Ala Val
            100                 105                 110
Ile Ile Arg Leu Phe Leu Glu Asn Leu Leu Lys Tyr Gly Trp Leu Met
        115                 120                 125
Lys Arg Asp Phe Trp Leu Ser Thr Phe Thr Ala Trp Pro Leu Phe Ile
        130                 135                 140
Cys Ser Leu Gly Leu Pro Ile Phe Pro Leu Ala Ala Phe Val Val Glu
145                 150                 155                 160
Lys Leu Ala Gln Lys Asn Leu Leu Pro Glu Pro Ile Val Leu Cys Ser
                165                 170                 175
His Val Ile Ile Thr Ser Ala Ser Val Leu Tyr Pro Ala Leu Val Ile
            180                 185                 190
Leu Arg Phe Asp Cys Ala Leu Met Ser Gly Ile Gly Leu Met Leu Tyr
        195                 200                 205
Ser Cys Ala Leu Trp Leu Lys Leu Val Ser Tyr Ala His Thr Ser Tyr
    210                 215                 220
Asp Met Arg Cys Glu Ala Lys Ser Arg Leu Glu Gly Lys Ser Ser Ala
225                 230                 235                 240
Asp Ser Lys Asn Gly Glu Leu Pro Tyr Arg Val Asn Ile Lys Asp Leu
                245                 250                 255
Ala Tyr Phe Met Val Ala Pro Thr Leu Cys Tyr Gln Leu Ser Tyr Pro
            260                 265                 270
Arg Thr Gln Phe Ile Arg Lys Phe Trp Val Ala Arg Gln Val Leu Lys
        275                 280                 285
Leu Ile Leu Val Asn Val Val Met Gly Phe Ile Ile Glu Gln Tyr Met
    290                 295                 300
Ile Pro Val Met His Asn Ser Lys Pro Pro Arg Arg Gly Tyr Trp Leu
305                 310                 315                 320
His Phe Ile Glu Arg Asn Leu Lys Leu Ala Val Pro Ser Ile Gly Leu
                325                 330                 335
Trp Phe Cys Ile Phe Tyr Ser Ile Phe His Leu Trp Leu Asn Ile Val
            340                 345                 350
Ala Glu Leu Leu Arg Phe Gly Asp Arg Glu Phe Tyr Lys Asp Trp Trp
        355                 360                 365
Asn Ala Lys Asn Met Glu Glu Tyr Trp Lys Met Trp Asn Ile Pro Val
    370                 375                 380
His Arg Trp Met Val Arg His Leu Tyr Gly Pro Cys Met Lys Arg Lys
385                 390                 395                 400
Leu Pro Arg Trp Val Ala Ile Ser Ile Ser Phe Leu Leu Ser Ala Val
                405                 410                 415
Leu His Glu Ile Cys Val Ser Val Pro Cys His Val Phe Gln Leu Trp
            420                 425                 430
Ala Phe Asn Gly Met Met Leu Gln Ile Pro Leu Val Leu Ser Ser Lys
        435                 440                 445
```

Pro Leu Gln Lys Arg Phe Pro Ser Ser Lys Ala Gly Asn Val Phe Phe
        450                 455                 460

Trp Phe Leu Phe Cys Ile Tyr Gly Gln Pro Asn Cys Val Leu Met Tyr
465                 470                 475                 480

Tyr His Ala Leu Met Glu Arg Arg Gly Leu Arg Ile Asp
                485                 490

<210> SEQ ID NO 9
<211> LENGTH: 1419
<212> TYPE: DNA
<213> ORGANISM: Cuphea viscosissima

<400> SEQUENCE: 9

```
atggcgatcg ttggcgtcga cgcttcctcc ctcagtcccg actctctccg ccggcgcaac      60
ttcgaccaag cttcactctc tcccaagacc accggcggca gtgttgtcga tgacgctgat     120
aacttgaagc tggagcgcga cgccaagaaa gctcaccgga cttcatctcc ggtacactgg     180
aagttggctg agagtcctct cagctccacc aatatcttca gcagagtca tgcaggtctc      240
ttaaacctct gcatggtcgt tcttattgct gtcaacagcc gactcatcct cgagaatctc     300
atcaagtatg gttggctcat gaagaggaac ttttggttgc atacgtttac agactggcct    360
ctcttcatgt gtagccttgg tcttcccatt ttccctcttg cagcattcct agtcgagaag     420
ttggcgcagc ggaatcgttt gcctgaacct attgtatttt gttctcatgt cattatcact     480
acggcatccg tcctttatcc cgcacttgta attctgggat ctgattctgc cttgatctct    540
ggtattgttc tgatgctcat tgcttgcact ctttggttaa aattggtgtc atatgcgcac     600
acaagttacg atatgagatg tgaggccaag tctcttcttg agggacaatc tagtgctgct    660
tcaaaaaatg tagagcttcc ttaccgcgta aacttcaaag atcttgtgta tttcatggtt    720
gcaccgaccc tatgttacca gatttcctat cctcgcacac aatgtgtacg taaaggttgg    780
gttgctcgcg aagtcttgaa gttgatattg ttcaatggag taatgggatt catcattgaa    840
caatatatga ttcctcttat gcataactct aaaggcccac agaggggaga ttggttacat    900
ttcatcgaaa ggattttgaa gcttgcggtt ccaggcgtat acctgtggtt ttgcatattc    960
tactgcattt ttcatctctg gttgaatata ctggcagagc tcctatgttt tggcgatcgt   1020
gaattttata gagactggtg gaatgccaag aacatggagg agtactggaa gatgtggaac   1080
atacctgttc ataagtggat ggtgcggcat ttatacggtc cctgcttgaa gaggaaaata   1140
ccgaggtcgg tcgcaatttc tatctcattt ctcttgtctg cagtgttgca tgagcttatt   1200
gtcagtattc catgccatgt gttcatgctg tgggcattca ctggaatgat acttcagatt   1260
ccgctggttt tgagttcgaa acccttacaa aaaatgttcc agagctccgt ggctgggaat   1320
atgttcttct ggttcttctt ttgcatcttt ggccagccca tgtgtgtgct tatgtactac   1380
catgccatga tggatcgtaa aatatcacag accgactag                          1419
```

<210> SEQ ID NO 10
<211> LENGTH: 472
<212> TYPE: PRT
<213> ORGANISM: Cuphea viscosissima

<400> SEQUENCE: 10

Met Ala Ile Val Gly Val Asp Ala Ser Ser Leu Ser Pro Asp Ser Leu
1               5                   10                  15

Arg Arg Arg Asn Phe Asp Gln Ala Ser Leu Ser Pro Lys Thr Thr Gly
            20                  25                  30

```
Gly Ser Val Val Asp Asp Ala Asp Asn Leu Lys Leu Glu Arg Asp Ala
         35                  40                  45

Lys Lys Ala His Arg Thr Ser Ser Pro Val His Trp Lys Leu Ala Glu
 50                  55                  60

Ser Pro Leu Ser Ser Thr Asn Ile Phe Lys Gln Ser His Ala Gly Leu
 65                  70                  75                  80

Leu Asn Leu Cys Met Val Val Leu Ile Ala Val Asn Ser Arg Leu Ile
                 85                  90                  95

Leu Glu Asn Leu Ile Lys Tyr Gly Trp Leu Met Lys Arg Asn Phe Trp
             100                 105                 110

Leu His Thr Phe Thr Asp Trp Pro Leu Phe Met Cys Ser Leu Gly Leu
             115                 120                 125

Pro Ile Phe Pro Leu Ala Ala Phe Leu Val Glu Lys Leu Ala Gln Arg
130                 135                 140

Asn Arg Leu Pro Glu Pro Ile Val Phe Cys Ser His Val Ile Ile Thr
145                 150                 155                 160

Thr Ala Ser Val Leu Tyr Pro Ala Leu Val Ile Leu Gly Ser Asp Ser
                 165                 170                 175

Ala Leu Ile Ser Gly Ile Val Leu Met Leu Ile Ala Cys Thr Leu Trp
             180                 185                 190

Leu Lys Leu Val Ser Tyr Ala His Thr Ser Tyr Asp Met Arg Cys Glu
             195                 200                 205

Ala Lys Ser Leu Leu Glu Gly Gln Ser Ser Ala Ala Ser Lys Asn Val
210                 215                 220

Glu Leu Pro Tyr Arg Val Asn Phe Lys Asp Leu Val Tyr Phe Met Val
225                 230                 235                 240

Ala Pro Thr Leu Cys Tyr Gln Ile Ser Tyr Pro Arg Thr Gln Cys Val
                 245                 250                 255

Arg Lys Gly Trp Val Ala Arg Glu Val Leu Lys Leu Ile Leu Phe Asn
             260                 265                 270

Gly Val Met Gly Phe Ile Ile Glu Gln Tyr Met Ile Pro Leu Met His
             275                 280                 285

Asn Ser Lys Gly Pro Gln Arg Gly Asp Trp Leu His Phe Ile Glu Arg
290                 295                 300

Ile Leu Lys Leu Ala Val Pro Gly Val Tyr Leu Trp Phe Cys Ile Phe
305                 310                 315                 320

Tyr Cys Ile Phe His Leu Trp Leu Asn Ile Leu Ala Glu Leu Leu Cys
                 325                 330                 335

Phe Gly Asp Arg Glu Phe Tyr Arg Asp Trp Trp Asn Ala Lys Asn Met
             340                 345                 350

Glu Glu Tyr Trp Lys Met Trp Asn Ile Pro Val His Lys Trp Met Val
             355                 360                 365

Arg His Leu Tyr Gly Pro Cys Leu Lys Arg Lys Ile Pro Arg Ser Val
370                 375                 380

Ala Ile Ser Ile Ser Phe Leu Leu Ser Ala Val Leu His Glu Leu Ile
385                 390                 395                 400

Val Ser Ile Pro Cys His Val Phe Met Leu Trp Ala Phe Thr Gly Met
                 405                 410                 415

Ile Leu Gln Ile Pro Leu Val Leu Ser Ser Lys Pro Leu Gln Lys Met
             420                 425                 430

Phe Gln Ser Ser Val Ala Gly Asn Met Phe Phe Trp Phe Phe Cys
             435                 440                 445
```

Ile Phe Gly Gln Pro Met Cys Val Leu Met Tyr Tyr His Ala Met Met
        450                 455                 460

Asp Arg Lys Ile Ser Gln Thr Asp
465                 470

<210> SEQ ID NO 11
<211> LENGTH: 1260
<212> TYPE: DNA
<213> ORGANISM: Cuphea viscosissima

<400> SEQUENCE: 11

```
atggtggctg ctgcagcaac ttctgcattc ttccccgttc cagccccggg aacctcccct    60
aaacccggga agtccggcaa ctggccatcg agcttgagcc taccttcaa gcccaagtca   120
atccccaatg gcggatttca ggttaaggca aatgccagtg cccatcctaa ggctaacggt   180
tctgcagtaa atctaaagtc tggcagcctc aacactcagg aggacacttc gtcgtcccct   240
cctccccggg ctttccttaa ccagttgcct gattggagta tgcttctgac tgcaatcacg   300
accgtcttcg tggcggcaga gaagcagtgg accatgcttg ataggaaatc taagaggcct   360
gacatgctcg tggactcggt tgggttgaag agtattgttc gagatgggct cgtgtccaga   420
cacagttttt cgattagatc ttatgaaata ggcgctgatc gaacagcctc tatagagacg   480
ctgatgaacc acttgcagga acaactatc aatcattgta gagtttggg tcttcataat   540
gacggctttg tcgtactcc tgggatgtgt aaaaacgacc tcatttgggt gcttacaaaa   600
atgcagatca tggtgaatcg ctacccaact ggggtgata ctgttgagat caatacctgg   660
ttctctcagt cggggaaaat cggtatggct agcgattggc taataagtga ttgcaacaca   720
ggagaaattc ttataagagc aacgagcgtg tgggctatga tgaatcaaaa gacgagaaga   780
ttctcaagac ttccatacga ggttcgccag gagttaacac tcatttttgt ggactctcct   840
catgtcattg aagacaatga tcagaaattg cgtaagtttg atgtgaagac tggtgattcc   900
attcgcaagg gtctaactcc gaggtggaat gacttggatg tgaatcagca cgtaagcaac   960
gtgaagtaca ttgggtggat tctcgagagt atgccaatag aagttttgga cccccaggag  1020
ctatgctctc tcaccgttga atataggcgg aatgcggaa tggacagtgt gctggagtcc  1080
gtgactgctg tggatccctc agaaaatgga ggccggtctc agtacaagca ccttctgcgg  1140
cttgaggatg ggactgatat cgtgaagagt agaactgagt ggcgaccgaa gaatgcagga  1200
actaacgggg cgatatcaac atcaacagca aagacttcaa atggaaactc ggtctcttag  1260
```

<210> SEQ ID NO 12
<211> LENGTH: 419
<212> TYPE: PRT
<213> ORGANISM: Cuphea viscosissima

<400> SEQUENCE: 12

Met Val Ala Ala Ala Ala Thr Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Thr Phe Lys Pro Lys Ser Ile Pro Asn Gly Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

```
Pro Pro Arg Ala Phe Leu Asn Gln Leu Pro Asp Trp Ser Met Leu Leu
                85                  90                  95
Thr Ala Ile Thr Thr Val Phe Val Ala Ala Glu Lys Gln Trp Thr Met
            100                 105                 110
Leu Asp Arg Lys Ser Lys Arg Pro Asp Met Leu Val Asp Ser Val Gly
        115                 120                 125
Leu Lys Ser Ile Val Arg Asp Gly Leu Val Ser Arg His Ser Phe Ser
130                 135                 140
Ile Arg Ser Tyr Glu Ile Gly Ala Asp Arg Thr Ala Ser Ile Glu Thr
145                 150                 155                 160
Leu Met Asn His Leu Gln Glu Thr Thr Ile Asn His Cys Lys Ser Leu
                165                 170                 175
Gly Leu His Asn Asp Gly Phe Gly Arg Thr Pro Gly Met Cys Lys Asn
            180                 185                 190
Asp Leu Ile Trp Val Leu Thr Lys Met Gln Ile Met Val Asn Arg Tyr
        195                 200                 205
Pro Thr Trp Gly Asp Thr Val Glu Ile Asn Thr Trp Phe Ser Gln Ser
210                 215                 220
Gly Lys Ile Gly Met Ala Ser Asp Trp Leu Ile Ser Asp Cys Asn Thr
225                 230                 235                 240
Gly Glu Ile Leu Ile Arg Ala Thr Ser Val Trp Ala Met Met Asn Gln
                245                 250                 255
Lys Thr Arg Arg Phe Ser Arg Leu Pro Tyr Glu Val Arg Gln Glu Leu
            260                 265                 270
Thr Pro His Phe Val Asp Ser Pro His Val Ile Glu Asp Asn Asp Gln
        275                 280                 285
Lys Leu Arg Lys Phe Asp Val Lys Thr Gly Asp Ser Ile Arg Lys Gly
290                 295                 300
Leu Thr Pro Arg Trp Asn Asp Leu Asp Val Asn Gln His Val Ser Asn
305                 310                 315                 320
Val Lys Tyr Ile Gly Trp Ile Leu Glu Ser Met Pro Ile Glu Val Leu
                325                 330                 335
Glu Thr Gln Glu Leu Cys Ser Leu Thr Val Glu Tyr Arg Arg Glu Cys
            340                 345                 350
Gly Met Asp Ser Val Leu Glu Ser Val Thr Ala Val Asp Pro Ser Glu
        355                 360                 365
Asn Gly Gly Arg Ser Gln Tyr Lys His Leu Leu Arg Leu Glu Asp Gly
        370                 375                 380
Thr Asp Ile Val Lys Ser Arg Thr Glu Trp Arg Pro Lys Asn Ala Gly
385                 390                 395                 400
Thr Asn Gly Ala Ile Ser Thr Ser Thr Ala Lys Thr Ser Asn Gly Asn
                405                 410                 415
Ser Val Ser

<210> SEQ ID NO 13
<211> LENGTH: 1248
<212> TYPE: DNA
<213> ORGANISM: Cuphea hookeriana

<400> SEQUENCE: 13
atggtggctg ctgcagcaag ttccgcattc ttccctgttc cagcccctgg agcctcccct    60
aaacctggga agttcggaaa ttggccctcg agcttgagcc cttccttcaa gcccaagtca   120
atccccaatg gcggatttca ggttaaggca aatgacagcg cccatccaaa ggctaacggt   180
```

```
tctgcagtta gtctaaagtc tggcagcctc aacactcagg aggacacttc gtcgtcccct    240
cctcctcgga ctttccttca ccagttgcct gattggagta ggcttctgac tgcaatcacg    300
accgtgttcg tgaaatctaa gaggcctgac atgcatgatc ggaaatccaa gaggcctgac    360
atgctggtgg actcgtttgg gttggagagt actgttcagg atgggctcgt gttccgacag    420 agttttcga ttaggtctta tgaaataggc actgatcgaa cggcctctat agagacactt     480
atgaaccact gcaggaaac atctctcaat cattgtaaga gtaccggtat ctccttgac      540 ggcttcggtc gtactcttga gatgtgtaaa agggacctca tttgggtggt aataaaaatg    600
cagatcaagg tgaatcgcta tccagcttgg ggcgatactg tcgagatcaa tacccggttc    660
tcccggttgg ggaaaatcgg tatgggtcgc gattggctaa taagtgattg caacacagga    720
gaaattcttg taagagctac gagcgcgtat gccatgatga atcaaaagac gagaagactc    780
tcaaaacttc catacgaggt tcaccaggag atagtgcctc tttttgtcga ctctcctgtc    840
attgaagaca gtgatctgaa agtgcataag tttaaagtga agactggtga ttccattcaa    900
aagggtctaa ctccggggtg gaatgacttg gatgtcaatc agcacgtaag caacgtgaag    960
tacattgggt ggattctcga gagtatgcca acagaagttt tggagaccca ggagctatgc    1020
tctctcgccc ttgaatatag gcgggaatgc ggaagggaca gtgtgctgga gtccgtgacc    1080
gctatggatc cctcaaaagt tggagtccgt tctcagtacc agcaccttct gcggcttgag    1140
gatgggactg ctatcgtgaa cggtgcaact gagtggcggc cgaagaatgc aggagctaac    1200
ggggcgatat caacgggaaa gacttcaaat ggaaactcgg tctcttag                 1248
```

<210> SEQ ID NO 14
<211> LENGTH: 415
<212> TYPE: PRT
<213> ORGANISM: Cuphea hookeriana

<400> SEQUENCE: 14

```
Met Val Ala Ala Ala Ser Ser Ala Phe Phe Pro Val Pro Ala Pro
1               5                   10                  15

Gly Ala Ser Pro Lys Pro Gly Lys Phe Gly Asn Trp Pro Ser Ser Leu
                20                  25                  30

Ser Pro Ser Phe Lys Pro Lys Ser Ile Pro Asn Gly Gly Phe Gln Val
                35                  40                  45

Lys Ala Asn Asp Ser Ala His Pro Lys Ala Asn Gly Ser Ala Val Ser
                50                  55                  60

Leu Lys Ser Gly Ser Leu Asn Thr Gln Glu Asp Thr Ser Ser Ser Pro
65                  70                  75                  80

Pro Pro Arg Thr Phe Leu His Gln Leu Pro Asp Trp Ser Arg Leu Leu
                85                  90                  95

Thr Ala Ile Thr Thr Val Phe Val Lys Ser Lys Arg Pro Asp Met His
                100                 105                 110

Asp Arg Lys Ser Lys Arg Pro Asp Met Leu Val Asp Ser Phe Gly Leu
                115                 120                 125

Glu Ser Thr Val Gln Asp Gly Leu Val Phe Arg Gln Ser Phe Ser Ile
                130                 135                 140

Arg Ser Tyr Glu Ile Gly Thr Asp Arg Thr Ala Ser Ile Glu Thr Leu
145                 150                 155                 160

Met Asn His Leu Gln Glu Thr Ser Leu Asn His Cys Lys Ser Thr Gly
                165                 170                 175

Ile Leu Leu Asp Gly Phe Gly Arg Thr Leu Glu Met Cys Lys Arg Asp
                180                 185                 190
```

```
Leu Ile Trp Val Val Ile Lys Met Gln Ile Lys Val Asn Arg Tyr Pro
        195                 200                 205

Ala Trp Gly Asp Thr Val Glu Ile Asn Thr Arg Phe Ser Arg Leu Gly
210                 215                 220

Lys Ile Gly Met Gly Arg Asp Trp Leu Ile Ser Asp Cys Asn Thr Gly
225                 230                 235                 240

Glu Ile Leu Val Arg Ala Thr Ser Ala Tyr Ala Met Met Asn Gln Lys
                245                 250                 255

Thr Arg Arg Leu Ser Lys Leu Pro Tyr Glu Val His Gln Glu Ile Val
            260                 265                 270

Pro Leu Phe Val Asp Ser Pro Val Ile Glu Asp Ser Asp Leu Lys Val
        275                 280                 285

His Lys Phe Lys Val Lys Thr Gly Asp Ser Ile Gln Lys Gly Leu Thr
    290                 295                 300

Pro Gly Trp Asn Asp Leu Asp Val Asn Gln His Val Ser Asn Val Lys
305                 310                 315                 320

Tyr Ile Gly Trp Ile Leu Glu Ser Met Pro Thr Glu Val Leu Glu Thr
                325                 330                 335

Gln Glu Leu Cys Ser Leu Ala Leu Glu Tyr Arg Glu Cys Gly Arg
            340                 345                 350

Asp Ser Val Leu Glu Ser Val Thr Ala Met Asp Pro Ser Lys Val Gly
        355                 360                 365

Val Arg Ser Gln Tyr Gln His Leu Leu Arg Leu Glu Asp Gly Thr Ala
    370                 375                 380

Ile Val Asn Gly Ala Thr Glu Trp Arg Pro Lys Asn Ala Gly Ala Asn
385                 390                 395                 400

Gly Ala Ile Ser Thr Gly Lys Thr Ser Asn Gly Asn Ser Val Ser
                405                 410                 415

<210> SEQ ID NO 15
<211> LENGTH: 1245
<212> TYPE: DNA
<213> ORGANISM: Cuphea pulcherrima

<400> SEQUENCE: 15
atggtggcta ccgctgcaag ctctgcattc ttccccgtgt cgtccccggt cacctcctct      60
agaccgggaa agcccggaaa tgggtcatcg agcttcagcc ccatcaagcc caaatttgtc     120
gccaatggcg ggttgcaggt taaggcaaac gccagtgccc ctcctaagat caatggttcc     180
tctgttggtc taaagtcctg cagtctcaag actcaggaag acactccttc ggcccctgct     240
ccacggactt ttatcaacca gttgcccgat tggagtatgc ttcttgctgc aattactact     300
gccttcttgg cagcagagaa gcagtggatg atgcttgatt ggaaacctaa gaggcctgac     360
atgcttgtgg acccgttcgg attgggaagt attgtccagc atgggcttgt gttcaggcag     420 aattttcga ttaggtccta tgaaataggc gctgatcgca ctgcgtctat agagacggtg     480
atgaaccact tgcaggaaac ggctctcaat catgttaaga gtgcgggct tatgaatgac     540 ggctttggtc gtactccaga gatgtataaa aaggacctta tttggttgt cgcgaaaatg     600 caggtcatgg ttaaccgcta tcctacttgg ggtgacacgg ttgaagtgaa tacttgggtt     660
gacaagttag ggaaaaatgg tatgcgtcgt gattggctca ttagtgattg caatacagga     720
gaaattctta ctagagcatc aagcgtgtgg gtcatgatga tcaaaagac aagaagattg     780 tcaaaaattc cagatgaggt tcgacgtgag atcgagcctc attttgtgga ctcacctcca     840
```

```
gtcattgaag acgatgaccg aaaacttccc aagctggatg acaagactgc tgactccatc    900
cgcaagggtc taactccgaa gtggaatgac ttggatgtca atcagcacgt caacaacgtg    960
aagtacatcg gctggattct tgagagtact ccacaagaaa ttctggagac ccaggagcta   1020 tgttcccttra ccctggaata caggcgaaa tgcggaaggg agagcgtgct ggagtccctc   1080
tctgctgcgg accctctgg aaagggctt gggtccagt tccagcacct tctgagactt   1140
gaggatggag gtgagatcgt gaaggggaga actgagtggc gaccaaagac tgcaggtatt   1200 aatgggggcga taccatccgg ggagacctca cctggagact cttag                  1245
```

<210> SEQ ID NO 16
<211> LENGTH: 414
<212> TYPE: PRT
<213> ORGANISM: Cuphea pulcherrima

<400> SEQUENCE: 16

```
Met Val Ala Thr Ala Ala Ser Ser Ala Phe Phe Pro Val Ser Pro
1               5                   10                  15

Val Thr Ser Ser Arg Pro Gly Lys Pro Gly Asn Gly Ser Ser Phe
            20                  25                  30

Ser Pro Ile Lys Pro Lys Phe Val Ala Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Cys Ser Leu Lys Thr Gln Glu Asp Thr Pro Ser Ala Pro Ala
65                  70                  75                  80

Pro Arg Thr Phe Ile Asn Gln Leu Pro Asp Trp Ser Met Leu Leu Ala
                85                  90                  95

Ala Ile Thr Thr Ala Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Ser Ile Val Gln His Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Met Asn Asp Gly Phe Gly Arg Thr Pro Glu Met Tyr Lys Lys Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Asp Lys Leu Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg Arg Glu Ile Glu
            260                 265                 270

Pro His Phe Val Asp Ser Pro Val Ile Glu Asp Asp Arg Lys
        275                 280                 285

Leu Pro Lys Leu Asp Asp Lys Thr Ala Asp Ser Ile Arg Lys Gly Leu
    290                 295                 300
```

```
Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Gln Glu Ile Leu Glu
            325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Ser Ala Ala Asp Pro Ser Gly Lys
            355                 360                 365

Gly Phe Gly Ser Gln Phe Gln His Leu Leu Arg Leu Glu Asp Gly Gly
            370                 375                 380

Glu Ile Val Lys Gly Arg Thr Glu Trp Arg Pro Lys Thr Ala Gly Ile
385                 390                 395                 400

Asn Gly Ala Ile Pro Ser Gly Glu Thr Ser Pro Gly Asp Ser
                405                 410

<210> SEQ ID NO 17
<211> LENGTH: 148
<212> TYPE: PRT
<213> ORGANISM: Limnanthes douglasii

<400> SEQUENCE: 17

Asn His Ala Ser Pro Ile Asp Ala Phe Phe Val Met Trp Leu Ala Pro
1               5                   10                  15

Ile Gly Thr Val Gly Val Ala Lys Lys Glu Val Ile Trp Tyr Pro Leu
            20                  25                  30

Leu Gly Gln Leu Tyr Thr Leu Ala His His Ile Arg Ile Asp Arg Ser
            35                  40                  45

Asn Pro Ala Ala Ala Ile Gln Ser Met Lys Glu Ala Val Arg Val Ile
50                  55                  60

Thr Glu Lys Asn Leu Ser Leu Ile Met Phe Pro Glu Gly Thr Arg Ser
65                  70                  75                  80

Arg Asp Gly Arg Leu Leu Pro Phe Lys Lys Gly Phe Val His Leu Ala
                85                  90                  95

Leu Gln Ser His Leu Pro Ile Val Pro Met Ile Leu Thr Gly Thr His
            100                 105                 110

Leu Ala Trp Arg Lys Gly Thr Phe Arg Val Arg Pro Val Pro Ile Thr
            115                 120                 125

Val Lys Tyr Leu Pro Pro Ile Asn Thr Asp Asp Trp Thr Val Asp Lys
    130                 135                 140

Ile Asp Asp Tyr
145

<210> SEQ ID NO 18
<211> LENGTH: 148
<212> TYPE: PRT
<213> ORGANISM: Vitis vinifera

<400> SEQUENCE: 18

Asn His Ala Ser Pro Ile Asp Ile Phe Leu Met Met Trp Leu Thr Pro
1               5                   10                  15

Thr Gly Thr Val Gly Ile Ala Lys Lys Glu Ile Val Trp Tyr Pro Leu
            20                  25                  30

Phe Gly Gln Leu Tyr Val Leu Ala Asn His Leu Arg Ile Asp Arg Ser
            35                  40                  45

Asn Pro Thr Ala Ala Ile Gln Ser Met Lys Glu Val Ala Arg Ala Ile
50                  55                  60
```

```
Val Lys Asn Lys Leu Ser Leu Ile Leu Phe Pro Glu Gly Thr Arg Ser
 65                  70                  75                  80

Lys Asp Gly Arg Leu Leu Pro Phe Lys Lys Gly Phe Val His Leu Ala
                 85                  90                  95

Met Gln Ser His Leu Pro Ile Val Pro Ile Val Leu Thr Gly Thr His
            100                 105                 110

Leu Ala Trp Arg Lys Gly Ser Leu His Val Arg Pro Ala Pro Leu Thr
            115                 120                 125

Val Lys Tyr Leu Pro Pro Ile Lys Thr Asp Asp Trp Thr Ala Asp Lys
130                 135                 140

Ile Asp Asp His
145
```

<210> SEQ ID NO 19
<211> LENGTH: 148
<212> TYPE: PRT
<213> ORGANISM: Cocos nucifera

<400> SEQUENCE: 19

```
Asn His Ala Ser Leu Val Asp Ile Phe Leu Ile Met Trp Leu Ile Pro
  1               5                  10                  15

Lys Gly Thr Val Thr Ile Ala Lys Lys Glu Ile Ile Trp Tyr Pro Leu
                 20                  25                  30

Phe Gly Gln Leu Tyr Val Leu Ala Asn His Gln Arg Ile Asp Arg Ser
             35                  40                  45

Asn Pro Ser Ala Ala Ile Glu Ser Ile Lys Glu Val Ala Arg Ala Val
         50                  55                  60

Val Lys Lys Asn Leu Ser Leu Ile Phe Pro Gly Gly Thr Arg Ser
 65                  70                  75                  80

Lys Thr Gly Arg Leu Leu Pro Phe Lys Lys Gly Phe Ile His Ile Ala
                 85                  90                  95

Leu Gln Thr Arg Leu Pro Ile Val Pro Met Val Leu Thr Gly Thr His
            100                 105                 110

Leu Ala Trp Arg Lys Asn Ser Leu Arg Val Arg Pro Ala Pro Ile Thr
            115                 120                 125

Val Lys Tyr Phe Ser Pro Ile Lys Thr Asp Asp Trp Glu Glu Glu Lys
130                 135                 140

Ile Asn His Tyr
145
```

<210> SEQ ID NO 20
<211> LENGTH: 148
<212> TYPE: PRT
<213> ORGANISM: Oryza sativa

<400> SEQUENCE: 20

```
Asn His Ala Ser Pro Leu Asp Ile Phe Leu Val Met Trp Leu Ala Pro
  1               5                  10                  15

Thr Gly Thr Val Gly Ile Ala Lys Lys Glu Ile Ile Trp Tyr Pro Leu
                 20                  25                  30

Phe Gly Gln Leu Tyr Val Leu Ala Asn His Leu Arg Ile Asp Arg Ser
             35                  40                  45

Asn Pro Ala Ala Ala Ile Glu Ser Met Lys Glu Val Ala Arg Ala Val
         50                  55                  60

Thr Lys Asn Asn Leu Ser Leu Ile Leu Phe Pro Glu Gly Thr Arg Ser
 65                  70                  75                  80
```

```
Lys Thr Gly Arg Leu Leu Pro Phe Lys Lys Gly Phe Val His Thr Ala
                 85                  90                  95
Leu Gln Thr Arg Leu Pro Ile Val Pro Met Val Val Thr Gly Thr His
            100                 105                 110
Leu Ala Trp Arg Lys Asn Ser Leu Arg Val Arg Pro Ala Pro Leu Thr
            115                 120                 125
Val Lys Val Leu Pro Pro Ile Glu Thr Asp Gly Trp Val Glu Glu Arg
        130                 135                 140
Ile Asp Glu Tyr
145

<210> SEQ ID NO 21
<211> LENGTH: 148
<212> TYPE: PRT
<213> ORGANISM: Ricinus communis

<400> SEQUENCE: 21

Asn His Ser Ser Pro Ile Asp Ile Phe Leu Ile Met Trp Leu Thr Pro
1               5                   10                  15
Thr Gly Thr Val Gly Val Ala Lys Lys Glu Ile Ile Trp Tyr Pro Leu
            20                  25                  30
Phe Gly Gln Leu Tyr Val Leu Ala Asn His Leu Arg Ile Asp Arg Ser
        35                  40                  45
Asn Pro Ala Ala Ala Ile Gln Ser Met Lys Val Ala Cys Ala Val
50                  55                  60
Ile Lys Asn Asn Leu Ser Leu Ile Ile Phe Pro Glu Gly Thr Arg Ser
65                  70                  75                  80
Lys Ser Gly Arg Leu Leu Pro Phe Lys Lys Gly Phe Val His Leu Ala
                85                  90                  95
Leu Gln Thr Arg Leu Pro Ile Val Pro Ile Val Leu Thr Gly Thr His
            100                 105                 110
Arg Ala Trp Arg Lys Asp Ser Leu His Val Arg Pro Ala Pro Ile Asn
            115                 120                 125
Val Lys Tyr Leu Arg Pro Ile Lys Thr Asp Asn Trp Thr Asp Asp Lys
        130                 135                 140
Val Asp Asp Tyr
145

<210> SEQ ID NO 22
<211> LENGTH: 148
<212> TYPE: PRT
<213> ORGANISM: Cuphea pulcherrima

<400> SEQUENCE: 22

Asn His Ala Ser Pro Leu Asp Ile Val Leu Thr Met Trp Leu Thr Pro
1               5                   10                  15
Lys Gly Thr Val Cys Ile Ala Lys Lys Glu Ile Val Trp Tyr Pro Leu
            20                  25                  30
Ile Gly Gln Leu Tyr Ala Leu Ala Gly His Leu Arg Ile Asp Arg Ser
        35                  40                  45
Asn Pro Val Ala Ala Ile Gln Ser Met Lys Glu Val Ala Arg Ala Val
50                  55                  60
Val Lys Asn Asp Leu Ser Leu Ile Ile Phe Pro Glu Gly Thr Arg Ser
65                  70                  75                  80
Lys Asp Gly Arg Leu Leu Pro Phe Lys Lys Gly Phe Val His Leu Ala
                85                  90                  95
```

```
Leu Gln Thr Arg Arg Pro Ile Val Pro Ile Val Leu Thr Gly Thr His
            100                 105                 110

Met Ala Trp Arg Lys Gly Ser Leu His Ile Arg Pro Thr Pro Leu Thr
            115                 120                 125

Val Lys Tyr Leu Pro Pro Ile Val Thr Thr Asp Trp Thr Pro Asp Arg
            130                 135                 140

Val Glu Asp Tyr
145

<210> SEQ ID NO 23
<211> LENGTH: 148
<212> TYPE: PRT
<213> ORGANISM: Homo sapiens

<400> SEQUENCE: 23

Asn His Gln Ser Ser Leu Asp Leu Leu Gly Met Met Glu Val Leu Pro
1               5                   10                  15

Gly Arg Cys Val Pro Ile Ala Lys Arg Glu Leu Leu Trp Ala Gly Ser
            20                  25                  30

Ala Gly Leu Ala Cys Trp Leu Ala Gly Val Ile Phe Ile Asp Arg Lys
        35                  40                  45

Arg Thr Gly Asp Ala Ile Ser Val Met Ser Glu Val Ala Gln Thr Leu
    50                  55                  60

Leu Thr Gln Asp Val Arg Val Trp Val Phe Pro Glu Gly Thr Arg Asn
65                  70                  75                  80

His Asn Gly Ser Met Leu Pro Phe Lys Arg Gly Ala Phe His Leu Ala
                85                  90                  95

Val Gln Ala Gln Val Pro Ile Val Pro Ile Val Met Ser Ser Tyr Gln
            100                 105                 110

Asp Phe Tyr Cys Lys Lys Glu Arg Arg Phe Thr Ser Gly Gln Cys Gln
        115                 120                 125

Val Arg Val Leu Pro Pro Val Pro Thr Glu Gly Leu Thr Pro Asp Asp
    130                 135                 140

Val Pro Ala Leu
145

<210> SEQ ID NO 24
<211> LENGTH: 148
<212> TYPE: PRT
<213> ORGANISM: Homo sapiens

<400> SEQUENCE: 24

Asn His Gln Ser Ile Leu Asp Met Met Gly Leu Met Glu Val Leu Pro
1               5                   10                  15

Glu Arg Cys Val Gln Ile Ala Lys Arg Glu Leu Leu Phe Leu Gly Pro
            20                  25                  30

Val Gly Leu Ile Met Tyr Leu Gly Gly Val Phe Phe Ile Asn Arg Gln
        35                  40                  45

Arg Ser Ser Thr Ala Met Thr Val Met Ala Asp Leu Gly Glu Arg Met
    50                  55                  60

Val Arg Glu Asn Leu Lys Val Trp Ile Tyr Pro Glu Gly Thr Arg Asn
65                  70                  75                  80

Asp Asn Gly Asp Leu Leu Pro Phe Lys Lys Gly Ala Phe Tyr Leu Ala
                85                  90                  95

Val Gln Ala Gln Val Pro Ile Val Pro Val Val Tyr Ser Ser Phe Ser
            100                 105                 110
```

Ser Phe Tyr Asn Thr Lys Lys Phe Phe Thr Ser Gly Thr Val Thr
        115                 120                 125

Val Gln Val Leu Glu Ala Ile Pro Thr Ser Gly Leu Thr Ala Ala Asp
    130                 135                 140

Val Pro Ala Leu
145

<210> SEQ ID NO 25
<211> LENGTH: 147
<212> TYPE: PRT
<213> ORGANISM: Saccharomyces cerevisiae

<400> SEQUENCE: 25

Asn His Gln Ser Thr Leu Asp Ile Phe Met Leu Gly Arg Ile Phe Pro
1               5                   10                  15

Pro Gly Cys Thr Val Thr Ala Lys Lys Ser Leu Lys Tyr Val Pro Phe
            20                  25                  30

Leu Gly Trp Phe Met Ala Leu Ser Gly Thr Tyr Phe Leu Asp Arg Ser
        35                  40                  45

Lys Arg Gln Glu Ala Ile Asp Thr Leu Asn Lys Gly Leu Glu Asn Val
    50                  55                  60

Lys Lys Asn Lys Arg Ala Leu Trp Val Phe Pro Gly Thr Arg Ser
65                  70                  75                  80

Tyr Thr Ser Glu Leu Thr Met Leu Pro Phe Lys Lys Gly Ala Phe His
                85                  90                  95

Leu Ala Gln Gln Gly Lys Ile Pro Ile Val Pro Val Val Ser Asn
            100                 105                 110

Thr Ser Thr Leu Val Ser Pro Lys Tyr Gly Val Phe Asn Arg Gly Cys
        115                 120                 125

Met Ile Val Arg Ile Leu Lys Pro Ile Ser Thr Glu Asn Leu Thr Lys
    130                 135                 140

Asp Lys Ile
145

<210> SEQ ID NO 26
<211> LENGTH: 146
<212> TYPE: PRT
<213> ORGANISM: Escherichia coli

<400> SEQUENCE: 26

Asn His Gln Asn Asn Tyr Asp Met Val Thr Ala Ser Asn Ile Val Gln
1               5                   10                  15

Pro Pro Thr Val Thr Val Gly Lys Lys Ser Leu Leu Trp Ile Pro Phe
            20                  25                  30

Phe Gly Gln Leu Tyr Trp Leu Thr Gly Asn Leu Leu Ile Asp Arg Asn
        35                  40                  45

Asn Arg Thr Lys Ala His Gly Thr Ile Ala Glu Val Val Asn His Phe
    50                  55                  60

Lys Lys Arg Arg Ile Ser Ile Trp Met Phe Pro Gly Thr Arg Ser
65                  70                  75                  80

Arg Gly Arg Gly Leu Leu Pro Phe Lys Thr Gly Ala Phe His Ala Ala
                85                  90                  95

Ile Ala Ala Gly Val Pro Ile Ile Pro Val Cys Val Ser Thr Thr Ser
            100                 105                 110

Asn Lys Ile Asn Leu Asn Arg Leu His Asn Gly Leu Val Ile Val Glu
        115                 120                 125

```
Met Leu Pro Pro Ile Asp Val Ser Gln Tyr Gly Lys Asp Gln Val Arg
    130                 135                 140

Glu Leu
145

<210> SEQ ID NO 27
<211> LENGTH: 148
<212> TYPE: PRT
<213> ORGANISM: Cuphea pulcherrima

<400> SEQUENCE: 27

Asn His Gln Ser Phe Leu Asp Ile Tyr Thr Leu Leu Thr Leu Gly Arg
1               5                   10                  15

Thr Phe Lys Phe Ile Ser Lys Thr Gly Ile Phe Leu Phe Pro Ile Ile
            20                  25                  30

Gly Trp Ala Met Tyr Met Leu Gly Thr Ile Pro Leu Lys Arg Ser Asp
        35                  40                  45

Ser Lys Ser Gln Leu Glu Thr Leu Lys Arg Cys Met Asp Leu Ile Lys
50                  55                  60

Lys Gly Ala Ser Val Phe Phe Pro Glu Gly Thr Arg Ser Lys Asp
65                  70                  75                  80

Gly Lys Leu Gly Ala Phe Lys Lys Gly Ala Phe Ser Ile Ala Ala Lys
                85                  90                  95

Asn Lys Val Pro Val Val Pro Ile Thr Leu Ile Gly Thr Gly Lys Ile
            100                 105                 110

Met Pro Pro Gly Arg Glu Leu Thr Val Asn Pro Gly Thr Val Gln Val
        115                 120                 125

Ile Ile His Lys Pro Ile Gln Gly Ser Asp Ala Glu Ala Met Cys Asn
    130                 135                 140

Glu Ala Arg Ala
145

<210> SEQ ID NO 28
<211> LENGTH: 148
<212> TYPE: PRT
<213> ORGANISM: Arabidopsis thaliana

<400> SEQUENCE: 28

Asn His Gln Ser Phe Leu Asp Ile Tyr Thr Leu Leu Ser Leu Gly Lys
1               5                   10                  15

Ser Phe Lys Phe Ile Ser Lys Thr Gly Ile Phe Val Ile Pro Ile Ile
            20                  25                  30

Gly Trp Ala Met Ser Met Met Gly Val Val Pro Leu Lys Arg Met Asp
        35                  40                  45

Pro Arg Ser Gln Val Asp Cys Leu Lys Arg Cys Met Glu Leu Leu Lys
50                  55                  60

Lys Gly Ala Ser Val Phe Phe Pro Glu Gly Thr Arg Ser Lys Asp
65                  70                  75                  80

Gly Arg Leu Gly Ser Phe Lys Lys Gly Ala Phe Thr Val Ala Ala Lys
                85                  90                  95

Thr Gly Val Ala Val Val Pro Ile Thr Leu Met Gly Thr Gly Lys Ile
            100                 105                 110

Met Pro Thr Gly Ser Glu Gly Ile Leu Asn His Gly Asn Val Arg Val
        115                 120                 125

Ile Ile His Lys Pro Ile His Gly Ser Lys Ala Asp Val Leu Cys Asn
    130                 135                 140
```

Glu Ala Arg Ser
145

<210> SEQ ID NO 29
<211> LENGTH: 139
<212> TYPE: PRT
<213> ORGANISM: Cuphea pulcherrima

<400> SEQUENCE: 29

Asn His Lys Ile Glu Leu Asp Trp Met Val Gly Trp Val Leu Gly Gln
1               5                   10                  15

His Leu Gly Cys Leu Gly Ser Ile Leu Ser Val Ala Lys Lys Ser Thr
            20                  25                  30

Lys Phe Leu Pro Val Phe Gly Trp Ser Leu Trp Phe Ser Glu Tyr Leu
        35                  40                  45

Phe Leu Glu Arg Asn Trp Ala Lys Asp Lys Thr Leu Lys Ser His
    50                  55                  60

Ile Glu Arg Leu Lys Asp Tyr Pro Leu Pro Phe Trp Leu Ile Ile Phe
65                  70                  75                  80

Val Glu Gly Thr Arg Phe Thr Arg Thr Lys Leu Leu Ala Ala Gln Gln
                85                  90                  95

Tyr Ala Ala Ser Ala Gly Leu Pro Val Pro Arg Asn Val Leu Ile Pro
            100                 105                 110

His Thr Lys Gly Phe Val Ser Ser Val Ser His Met Arg Ser Phe Val
        115                 120                 125

Pro Ala Ile Tyr Asp Val Thr Val Ala Phe Pro
    130                 135

<210> SEQ ID NO 30
<211> LENGTH: 139
<212> TYPE: PRT
<213> ORGANISM: Cuphea viscosissima

<400> SEQUENCE: 30

Asn His Met Thr Glu Leu Asp Trp Met Val Gly Trp Val Met Gly Gln
1               5                   10                  15

His Phe Gly Cys Leu Gly Ser Ile Ile Ser Val Ala Lys Lys Ser Thr
            20                  25                  30

Lys Phe Leu Pro Val Leu Gly Trp Ser Met Trp Phe Ser Glu Tyr Leu
        35                  40                  45

Tyr Leu Glu Arg Ser Trp Ala Lys Asp Lys Ser Thr Leu Lys Ser His
    50                  55                  60

Ile Glu Arg Leu Ile Asp Tyr Pro Leu Pro Phe Trp Leu Val Ile Phe
65                  70                  75                  80

Val Glu Gly Thr Arg Phe Thr Arg Thr Lys Leu Leu Ala Ala Gln Gln
                85                  90                  95

Tyr Ala Val Ser Ser Gly Leu Pro Val Pro Arg Asn Val Leu Ile Pro
            100                 105                 110

Arg Thr Lys Gly Phe Val Ser Cys Val Ser His Met Arg Ser Phe Val
        115                 120                 125

Pro Ala Val Tyr Asp Val Thr Val Ala Phe Pro
    130                 135

<210> SEQ ID NO 31
<211> LENGTH: 139
<212> TYPE: PRT
<213> ORGANISM: Cuphea pulcherrima

<400> SEQUENCE: 31

```
Asn His Lys Ser Asp Ile Asp Trp Leu Val Gly Trp Val Leu Ala Gln
1               5                   10                  15

Arg Ser Gly Cys Leu Gly Ser Thr Leu Ala Val Met Lys Lys Ser Ser
            20                  25                  30

Lys Phe Leu Pro Val Ile Gly Trp Ser Met Trp Phe Ser Glu Tyr Leu
        35                  40                  45

Phe Leu Glu Arg Ser Trp Ala Lys Asp Glu Ser Thr Leu Lys Ser Gly
    50                  55                  60

Leu Lys Arg Leu Lys Asp Tyr Pro Leu Pro Phe Trp Leu Ala Leu Phe
65                  70                  75                  80

Val Glu Gly Thr Arg Phe Thr Gln Ala Lys Leu Leu Ala Ala Gln Gln
                85                  90                  95

Tyr Ala Ala Ser Ser Gly Leu Pro Val Pro Arg Asn Val Leu Ile Pro
            100                 105                 110

Arg Thr Lys Gly Phe Val Ser Ser Val Ser His Met Arg Ser Phe Val
        115                 120                 125

Pro Ala Ile Tyr Asp Val Thr Val Ala Ile Pro
    130                 135
```

<210> SEQ ID NO 32
<211> LENGTH: 139
<212> TYPE: PRT
<213> ORGANISM: Cuphea pulcherrima

<400> SEQUENCE: 32

```
Asn His Lys Ser Asp Ile Asp Trp Leu Val Gly Trp Val Leu Ala Gln
1               5                   10                  15

Arg Ser Gly Cys Leu Gly Ser Thr Leu Ala Val Met Lys Lys Ser Ser
            20                  25                  30

Lys Phe Leu Pro Val Ile Gly Trp Ser Met Trp Phe Ser Glu Tyr Leu
        35                  40                  45

Phe Leu Glu Arg Asn Trp Ala Lys Asp Glu Ser Thr Leu Lys Ser Gly
    50                  55                  60

Leu Asn Arg Leu Lys Asp Tyr Pro Leu Pro Phe Trp Leu Ala Leu Phe
65                  70                  75                  80

Val Glu Gly Thr Arg Phe Thr Arg Ala Lys Leu Leu Ala Ala Gln Gln
                85                  90                  95

Tyr Ala Ala Ser Ser Gly Leu Pro Val Pro Arg Asn Val Leu Ile Pro
            100                 105                 110

Arg Thr Lys Gly Phe Val Ser Ser Val Ser His Met Arg Ser Phe Val
        115                 120                 125

Pro Ala Ile Tyr Asp Val Thr Val Ala Ile Pro
    130                 135
```

<210> SEQ ID NO 33
<211> LENGTH: 139
<212> TYPE: PRT
<213> ORGANISM: Arabidopsis thaliana

<400> SEQUENCE: 33

```
Asn His Arg Ser Asp Ile Asp Trp Leu Val Gly Trp Ile Leu Ala Gln
1               5                   10                  15

Arg Ser Gly Cys Leu Gly Ser Ala Leu Ala Val Met Lys Lys Ser Ser
            20                  25                  30

Lys Phe Leu Pro Val Ile Gly Trp Ser Met Trp Phe Ser Glu Tyr Leu
```

```
            35                  40                  45
Phe Leu Glu Arg Asn Trp Ala Lys Asp Glu Ser Thr Leu Lys Ser Gly
     50                  55                  60
Leu Gln Arg Leu Ser Asp Phe Pro Arg Pro Phe Trp Leu Ala Leu Phe
 65                  70                  75                  80
Val Glu Gly Thr Arg Phe Thr Glu Ala Lys Leu Lys Ala Ala Gln Glu
                 85                  90                  95
Tyr Ala Ala Ser Ser Glu Leu Pro Ile Pro Arg Asn Val Leu Ile Pro
                100                 105                 110
Arg Thr Lys Gly Phe Val Ser Ala Val Ser Asn Met Arg Ser Phe Val
                115                 120                 125
Pro Ala Ile Tyr Asp Met Thr Val Thr Ile Pro
                130                 135

<210> SEQ ID NO 34
<211> LENGTH: 139
<212> TYPE: PRT
<213> ORGANISM: Brassica napus

<400> SEQUENCE: 34

Asn His Arg Ser Asp Ile Asp Trp Leu Val Gly Trp Ile Leu Ala Gln
 1               5                  10                  15
Arg Ser Gly Cys Leu Gly Ser Ala Leu Ala Val Met Lys Lys Ser Ser
                 20                  25                  30
Lys Phe Leu Pro Val Ile Gly Trp Ser Met Trp Phe Ser Glu Tyr Leu
                 35                  40                  45
Phe Leu Glu Arg Asn Trp Ala Lys Asp Glu Ser Thr Leu Lys Ser Gly
     50                  55                  60
Leu Gln Arg Leu Asn Asp Phe Pro Arg Pro Phe Trp Leu Ala Leu Phe
 65                  70                  75                  80
Val Glu Gly Thr Arg Phe Thr Glu Ala Lys Leu Lys Ala Ala Gln Glu
                 85                  90                  95
Tyr Ala Ala Ser Ser Glu Leu Pro Val Pro Arg Asn Val Leu Ile Pro
                100                 105                 110
Arg Thr Lys Gly Phe Val Ser Ala Val Ser Asn Met Arg Ser Phe Val
                115                 120                 125
Pro Ala Ile Tyr Asp Met Thr Val Ala Ile Pro
                130                 135

<210> SEQ ID NO 35
<211> LENGTH: 139
<212> TYPE: PRT
<213> ORGANISM: Cuphea pulcherrima

<400> SEQUENCE: 35

Asn His Arg Ser Asp Ile Asp Trp Leu Val Gly Trp Val Leu Ala Gln
 1               5                  10                  15
Arg Ala Gly Cys Leu Gly Ser Ala Leu Ala Ile Met Lys Lys Ser Ala
                 20                  25                  30
Lys Phe Leu Pro Val Ile Gly Trp Ser Met Trp Phe Ser Asp Tyr Ile
                 35                  40                  45
Phe Leu Asp Arg Thr Trp Ala Lys Asp Glu Lys Thr Leu Lys Ser Gly
     50                  55                  60
Phe His Arg Leu Ala Asp Phe Pro Met Pro Phe Trp Leu Ala Leu Phe
 65                  70                  75                  80
Val Glu Gly Thr Arg Phe Thr Pro Ala Lys Leu Leu Ala Ala Gln Glu
```

```
                    85                  90                  95
Tyr Ala Ala Ser Arg Gly Leu His Val Pro Lys Asn Val Leu Ile Pro
                100                 105                 110
Arg Thr Lys Gly Phe Val Thr Ala Val Thr His Met Arg Ser Tyr Val
            115                 120                 125
Pro Ala Ile Tyr Asp Cys Thr Val Asp Ile Ser
        130                 135
```

<210> SEQ ID NO 36
<211> LENGTH: 139
<212> TYPE: PRT
<213> ORGANISM: Arabidopsis thaliana

<400> SEQUENCE: 36

```
Asn His Arg Ser Asp Ile Asp Trp Leu Ile Gly Trp Val Met Ala Gln
 1               5                  10                  15
Arg Val Gly Cys Leu Gly Ser Ser Leu Ala Ile Met Lys Lys Glu Ala
                20                  25                  30
Lys Tyr Leu Pro Ile Ile Gly Trp Ser Met Trp Phe Ser Asp Tyr Ile
            35                  40                  45
Phe Leu Glu Arg Ser Trp Ala Lys Asp Glu Asn Thr Leu Lys Ala Gly
        50                  55                  60
Phe Lys Arg Leu Glu Asp Phe Pro Met Thr Phe Trp Leu Ala Leu Phe
65                  70                  75                  80
Val Glu Gly Thr Arg Phe Thr Gln Glu Lys Leu Glu Ala Ala Gln Glu
                85                  90                  95
Tyr Ala Ser Ile Arg Ser Leu Pro Ser Ile Arg Asn Val Leu Ile Pro
                100                 105                 110
Arg Thr Lys Gly Phe Val Ser Ala Val Ser Glu Ile Arg Ser Phe Val
            115                 120                 125
Pro Ala Ile Tyr Asp Cys Thr Leu Thr Val His
        130                 135
```

<210> SEQ ID NO 37
<211> LENGTH: 493
<212> TYPE: PRT
<213> ORGANISM: Cuphea pulcherrima

<400> SEQUENCE: 37

```
Met His Glu Ala Val Ser His Phe Leu His Arg His Ala Pro Leu Ser
 1               5                  10                  15
Leu Ser Gly Phe Ala Met Ala Ile Val Ser Gly Thr Leu Gly Val Ala
                20                  25                  30
Ala Ser Ser Phe Ile Pro Asp Ser Asp His Ser Thr Thr Ser Pro Ser
            35                  40                  45
Leu Arg Lys Arg Asn Ser Ser Ser Leu Phe Pro Lys Ala Ser Asp Thr
        50                  55                  60
Ser Ser Val Asp Gly Lys Ala Ala His Arg Thr Ser Ser Pro Val His
65                  70                  75                  80
Leu Lys Leu Ala Glu Ser Pro Leu Ser Ser Arg Asn Ile Phe Lys Gln
                85                  90                  95
Asn His Glu Gly Leu Phe Asn Leu Cys Met Val Thr Leu Val Ala Val
                100                 105                 110
Ile Ile Arg Leu Phe Leu Glu Asn Leu Leu Lys Tyr Gly Trp Leu Met
            115                 120                 125
Lys Arg Asp Phe Trp Leu Ser Thr Phe Thr Ala Trp Pro Leu Phe Ile
```

```
            130                 135                 140
Cys Ser Leu Gly Leu Pro Ile Phe Pro Leu Ala Ala Phe Val Val Glu
145                 150                 155                 160

Lys Leu Ala Gln Lys Asn Leu Leu Pro Glu Pro Ile Val Leu Cys Ser
                165                 170                 175

His Val Ile Ile Thr Ser Ala Ser Val Leu Tyr Pro Ala Leu Val Ile
            180                 185                 190

Leu Arg Phe Asp Cys Ala Leu Met Ser Gly Ile Gly Leu Met Leu Tyr
        195                 200                 205

Ser Cys Ala Leu Trp Leu Lys Leu Val Ser Tyr Ala His Thr Ser Tyr
    210                 215                 220

Asp Met Arg Cys Glu Ala Lys Ser Arg Leu Glu Gly Lys Ser Ser Ala
225                 230                 235                 240

Asp Ser Lys Asn Gly Glu Leu Pro Tyr Arg Val Asn Ile Lys Asp Leu
                245                 250                 255

Ala Tyr Phe Met Val Ala Pro Thr Leu Cys Tyr Gln Leu Ser Tyr Pro
            260                 265                 270

Arg Thr Gln Phe Ile Arg Lys Phe Trp Val Ala Arg Gln Val Leu Lys
        275                 280                 285

Leu Ile Leu Val Asn Val Val Met Gly Phe Ile Ile Glu Gln Tyr Met
    290                 295                 300

Ile Pro Val Met His Asn Ser Lys Pro Pro Arg Arg Gly Tyr Trp Leu
305                 310                 315                 320

His Phe Ile Glu Arg Asn Leu Lys Leu Ala Val Pro Ser Ile Gly Leu
                325                 330                 335

Trp Phe Cys Ile Phe Tyr Ser Ile Phe His Leu Trp Leu Asn Ile Val
            340                 345                 350

Ala Glu Leu Leu Arg Phe Gly Asp Arg Glu Phe Tyr Lys Asp Trp Trp
        355                 360                 365

Asn Ala Lys Asn Met Glu Glu Tyr Trp Lys Met Trp Asn Ile Pro Val
    370                 375                 380

His Arg Trp Met Val Arg His Leu Tyr Gly Pro Cys Met Lys Arg Lys
385                 390                 395                 400

Leu Pro Arg Trp Val Ala Ile Ser Ile Ser Phe Leu Leu Ser Ala Val
                405                 410                 415

Leu His Glu Ile Cys Val Ser Val Pro Cys His Val Phe Gln Leu Trp
            420                 425                 430

Ala Phe Asn Gly Met Met Leu Gln Ile Pro Leu Val Leu Ser Ser Lys
        435                 440                 445

Pro Leu Gln Lys Arg Phe Pro Ser Ser Lys Ala Gly Asn Val Phe Phe
    450                 455                 460

Trp Phe Leu Phe Cys Ile Tyr Gly Gln Pro Asn Cys Val Leu Met Tyr
465                 470                 475                 480

Tyr His Ala Leu Met Glu Arg Arg Gly Leu Arg Ile Asp
                485                 490

<210> SEQ ID NO 38
<211> LENGTH: 520
<212> TYPE: PRT
<213> ORGANISM: Arabidopsis thaliana

<400> SEQUENCE: 38

Met Ala Ile Leu Asp Ser Ala Gly Val Thr Thr Val Thr Glu Asn Gly
1               5                   10                  15
```

```
Gly Gly Glu Phe Val Asp Leu Asp Arg Leu Arg Arg Lys Ser Arg
            20                  25                  30
Ser Asp Ser Ser Asn Gly Leu Leu Leu Ser Gly Ser Asp Asn Asn Ser
        35                  40                  45
Pro Ser Asp Asp Val Gly Ala Pro Ala Asp Val Arg Asp Arg Ile Asp
    50                  55                  60
Ser Val Val Asn Asp Asp Ala Gln Gly Thr Ala Asn Leu Ala Gly Asp
65                  70                  75                  80
Asn Asn Gly Gly Gly Asp Asn Asn Gly Gly Arg Gly Gly Gly Glu
                85                  90                  95
Gly Arg Gly Asn Ala Asp Ala Thr Phe Thr Tyr Arg Pro Ser Val Pro
                100                 105                 110
Ala His Arg Arg Ala Arg Glu Ser Pro Leu Ser Ser Asp Ala Ile Phe
        115                 120                 125
Lys Gln Ser His Ala Gly Leu Phe Asn Leu Cys Val Val Val Leu Ile
    130                 135                 140
Ala Val Asn Ser Arg Leu Ile Ile Glu Asn Leu Met Lys Tyr Gly Trp
145                 150                 155                 160
Leu Ile Arg Thr Asp Phe Trp Phe Ser Ser Arg Ser Leu Arg Asp Trp
                165                 170                 175
Pro Leu Phe Met Cys Cys Ile Ser Leu Ser Ile Phe Pro Leu Ala Ala
                180                 185                 190
Phe Thr Val Glu Lys Leu Val Leu Gln Lys Tyr Ile Ser Glu Pro Val
        195                 200                 205
Val Ile Phe Leu His Ile Ile Ile Thr Met Thr Glu Val Leu Tyr Pro
210                 215                 220
Val Tyr Val Thr Leu Arg Cys Asp Ser Ala Phe Leu Ser Gly Val Thr
225                 230                 235                 240
Leu Met Leu Leu Thr Cys Ile Val Trp Leu Lys Leu Val Ser Tyr Ala
                245                 250                 255
His Thr Ser Tyr Asp Ile Arg Ser Leu Ala Asn Ala Ala Asp Lys Ala
                260                 265                 270
Asn Pro Glu Val Ser Tyr Tyr Val Ser Leu Lys Ser Leu Ala Tyr Phe
        275                 280                 285
Met Val Ala Pro Thr Leu Cys Tyr Gln Pro Ser Tyr Pro Arg Ser Ala
    290                 295                 300
Cys Ile Arg Lys Gly Trp Val Ala Arg Gln Phe Ala Lys Leu Val Ile
305                 310                 315                 320
Phe Thr Gly Phe Met Gly Phe Ile Ile Glu Gln Tyr Ile Asn Pro Ile
                325                 330                 335
Val Arg Asn Ser Lys His Pro Leu Lys Gly Asp Leu Leu Tyr Ala Ile
                340                 345                 350
Glu Arg Val Leu Lys Leu Ser Val Pro Asn Leu Tyr Val Trp Leu Cys
        355                 360                 365
Met Phe Tyr Cys Phe Phe His Leu Trp Leu Asn Ile Leu Ala Glu Leu
    370                 375                 380
Leu Cys Phe Gly Asp Arg Glu Phe Tyr Lys Asp Trp Trp Asn Ala Lys
385                 390                 395                 400
Ser Val Gly Asp Tyr Trp Arg Met Trp Asn Met Pro Val His Lys Trp
                405                 410                 415
Met Val Arg His Ile Tyr Phe Pro Cys Leu Arg Ser Lys Ile Pro Lys
                420                 425                 430
Thr Leu Ala Ile Ile Ile Ala Phe Leu Val Ser Ala Val Phe His Glu
```

```
            435                 440                 445
Leu Cys Ile Ala Val Pro Cys Arg Leu Phe Lys Leu Trp Ala Phe Leu
450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
                485                 490                 495

Cys Ile Phe Gly Gln Pro Met Cys Val Leu Leu Tyr Tyr His Asp Leu
                500                 505                 510

Met Asn Arg Lys Gly Ser Met Ser
515                 520

<210> SEQ ID NO 39
<211> LENGTH: 503
<212> TYPE: PRT
<213> ORGANISM: Brassica napus

<400> SEQUENCE: 39

Met Ala Ile Leu Asp Ser Gly Gly Val Ala Val Pro Pro Thr Glu Asn
1               5                   10                  15

Gly Val Ala Asp Leu Asp Arg Leu His Arg Arg Lys Ser Ser Ser Asp
                20                  25                  30

Ser Ser Asn Gly Leu Leu Ser Asp Thr Ser Pro Ser Asp Asp Val Gly
            35                  40                  45

Ala Ala Ala Ala Glu Arg Asp Arg Val Asp Ser Ala Ala Glu Glu Glu
50                  55                  60

Ala Gln Gly Thr Ala Asn Leu Ala Gly Gly Asp Ala Glu Thr Arg Glu
65                  70                  75                  80

Ser Ala Gly Gly Asp Val Arg Phe Thr Tyr Arg Pro Ser Val Pro Ala
                85                  90                  95

His Arg Arg Thr Arg Glu Ser Pro Leu Ser Ser Asp Ala Ile Phe Lys
                100                 105                 110

Gln Ser His Ala Gly Leu Phe Asn Leu Cys Val Val Leu Val Ala
            115                 120                 125

Val Asn Ser Arg Leu Ile Ile Glu Asn Leu Met Lys Tyr Gly Trp Leu
130                 135                 140

Ile Arg Thr Asp Phe Trp Phe Ser Ser Thr Ser Leu Arg Asp Trp Pro
145                 150                 155                 160

Leu Phe Met Cys Cys Leu Ser Leu Ser Val Phe Pro Leu Ala Ala Phe
                165                 170                 175

Thr Val Glu Lys Met Val Leu Gln Lys Phe Ile Ser Glu Pro Val Ala
                180                 185                 190

Ile Ile Leu His Val Ile Ile Thr Met Thr Glu Val Leu Tyr Pro Val
                195                 200                 205

Tyr Val Thr Leu Arg Cys Asp Ser Ala Phe Leu Ser Gly Val Thr Leu
210                 215                 220

Met Leu Leu Thr Cys Ile Val Trp Leu Lys Leu Val Ser Tyr Ala His
225                 230                 235                 240

Thr Ser Tyr Asp Ile Arg Thr Leu Ala Asn Ser Ala Asp Lys Val Asp
                245                 250                 255

Pro Glu Ile Ser Tyr Tyr Val Ser Leu Lys Ser Leu Ala Tyr Phe Met
                260                 265                 270

Val Ala Pro Thr Leu Cys Tyr Gln Pro Ser Tyr Pro Arg Ser Pro Cys
                275                 280                 285
```

```
Ile Arg Lys Gly Trp Val Ala Arg Gln Leu Ala Lys Leu Val Ile Phe
        290                 295                 300

Thr Gly Leu Met Gly Phe Ile Ile Glu Gln Tyr Ile Asn Pro Ile Val
305                 310                 315                 320

Arg Asn Ser Lys His Pro Leu Lys Gly Asp Leu Leu Tyr Ala Ile Glu
                325                 330                 335

Arg Val Leu Lys Leu Ser Val Pro Asn Leu Tyr Val Trp Leu Cys Met
                340                 345                 350

Phe Tyr Cys Phe Phe His Leu Trp Leu Asn Ile Leu Ala Glu Leu Leu
                355                 360                 365

Cys Phe Gly Asp Arg Glu Phe Tyr Lys Asp Trp Asn Ala Lys Ser
370                 375                 380

Val Gly Asp Tyr Trp Arg Met Trp Asn Met Pro Val His Lys Trp Met
385                 390                 395                 400

Val Arg His Val Tyr Phe Pro Cys Leu Arg Ile Lys Ile Pro Lys Val
                405                 410                 415

Pro Ala Ile Ile Ile Ala Phe Leu Val Ser Ala Val Phe His Glu Leu
                420                 425                 430

Cys Ile Ala Val Pro Cys Arg Leu Phe Asn Leu Trp Ala Phe Met Gly
                435                 440                 445

Ile Met Phe Gln Val Pro Leu Val Phe Ile Thr Asn Phe Leu Gln Glu
450                 455                 460

Arg Phe Gly Ser Met Val Gly Asn Met Ile Phe Gly Ser Ala Ser Cys
465                 470                 475                 480

Ile Phe Gly Gln Pro Met Cys Gly Leu Leu Tyr Tyr His Asp Leu Met
                485                 490                 495

Asn Arg Lys Gly Ser Met Ser
                500

<210> SEQ ID NO 40
<211> LENGTH: 521
<212> TYPE: PRT
<213> ORGANISM: Ricinus communis

<400> SEQUENCE: 40

Met Thr Ile Leu Glu Thr Pro Glu Thr Leu Gly Val Ile Ser Ser Ser
1               5                   10                  15

Ala Thr Ser Asp Leu Asn Leu Ser Leu Arg Arg Arg Thr Ser Asn
                20                  25                  30

Asp Ser Asp Gly Ala Leu Ala Asp Leu Ala Ser Lys Phe Asp Asp Asp
                35                  40                  45

Asp Asp Val Arg Ser Glu Asp Ser Ala Glu Asn Ile Ile Glu Asp Pro
50                  55                  60

Val Ala Ala Val Thr Glu Leu Ala Thr Ala Lys Ser Asn Gly Lys Asp
65                  70                  75                  80

Cys Val Ala Asn Ser Asn Lys Asp Lys Ile Asp Ser His Gly Gly Ser
                85                  90                  95

Ser Asp Phe Lys Leu Ala Tyr Arg Pro Ser Val Pro Ala His Arg Ser
                100                 105                 110

Leu Lys Glu Ser Pro Leu Ser Ser Asp Leu Ile Phe Lys Gln Ser His
                115                 120                 125

Ala Gly Leu Phe Asn Leu Cys Ile Val Val Leu Val Ala Val Asn Ser
                130                 135                 140

Arg Leu Ile Ile Glu Asn Leu Met Lys Tyr Gly Trp Leu Ile Lys Thr
145                 150                 155                 160
```

```
Gly Phe Trp Phe Ser Ser Arg Ser Leu Arg Asp Trp Pro Leu Phe Met
                165                 170                 175
Cys Cys Leu Ser Leu Pro Val Phe Pro Leu Ala Ala Tyr Leu Val Glu
            180                 185                 190
Lys Ala Ala Tyr Arg Lys Tyr Ile Ser Pro Pro Ile Val Ile Phe Leu
        195                 200                 205
His Val Ile Ile Thr Ser Ala Ala Val Leu Tyr Pro Ala Ser Val Ile
    210                 215                 220
Leu Ser Cys Glu Ser Ala Phe Leu Ser Gly Val Thr Leu Met Glu Leu
225                 230                 235                 240
Ala Cys Met Val Trp Leu Lys Leu Val Ser Tyr Ala His Thr Asn Tyr
                245                 250                 255
Asp Met Arg Ala Ile Ala Asp Thr Ile His Lys Glu Asp Ala Ser Asn
            260                 265                 270
Ser Ser Ser Thr Glu Tyr Cys His Asp Val Ser Phe Lys Thr Leu Ala
        275                 280                 285
Tyr Phe Met Val Ala Pro Thr Leu Cys Tyr Gln Pro Ser Tyr Pro Arg
    290                 295                 300
Thr Ala Phe Ile Arg Lys Gly Trp Val Phe Arg Gln Phe Val Lys Leu
305                 310                 315                 320
Ile Ile Phe Thr Gly Phe Met Gly Phe Ile Ile Glu Gln Tyr Ile Asn
                325                 330                 335
Pro Ile Val Gln Asn Ser Gln His Pro Leu Lys Gly Asp Leu Leu Tyr
            340                 345                 350
Ala Ile Glu Arg Val Leu Lys Leu Ser Val Pro Asn Leu Tyr Val Trp
        355                 360                 365
Leu Cys Leu Phe Tyr Cys Phe Phe His Leu Trp Leu Asn Ile Val Ala
    370                 375                 380
Glu Leu Leu Arg Phe Gly Asp Arg Glu Phe Tyr Lys Asp Trp Trp Asn
385                 390                 395                 400
Ala Lys Thr Val Glu Glu Tyr Trp Arg Met Trp Asn Met Pro Val His
                405                 410                 415
Lys Trp Met Val Arg His Ile Tyr Phe Pro Cys Leu Arg Arg Lys Ile
            420                 425                 430
Pro Arg Gly Val Ala Ile Val Ile Ala Phe Phe Val Ser Ala Val Phe
        435                 440                 445
His Glu Leu Cys Ile Ala Val Pro Cys His Met Phe Lys Leu Trp Ala
    450                 455                 460
Phe Phe Gly Ile Met Phe Gln Ile Pro Leu Val Val Ile Thr Asn Tyr
465                 470                 475                 480
Phe Gln Arg Lys Phe Arg Ser Ser Met Val Gly Asn Met Ile Phe Trp
                485                 490                 495
Phe Phe Phe Cys Ile Leu Gly Gln Pro Met Cys Val Leu Leu Tyr Tyr
            500                 505                 510
His Asp Leu Met Asn Arg Asp Gly Asn
        515                 520

<210> SEQ ID NO 41
<211> LENGTH: 532
<212> TYPE: PRT
<213> ORGANISM: Olea europaea

<400> SEQUENCE: 41

Met Thr Ile Pro Glu Leu Pro Glu Ser Leu Glu Thr Thr Thr Leu Asn
```

-continued

```
1               5                   10                  15
Ser His His Ser Arg Ala Ala Ser Thr Val Arg Arg Ser Ile Asp
            20                  25                  30
Val Ala Val Leu Glu Ser Asp Ser Asn Ser Leu Glu Ala Val Asn Asp
            35                  40                  45
Ser Asp Ser Asp Val Asn Asn Thr Asn Glu Met Gly Asn Leu Arg Gly
    50                  55                  60
Gly Val Val Glu Ser Ala Leu Glu Glu Pro Ser Glu Leu Gly Thr Glu
65                  70                  75                  80
Gly Leu Arg Asn Gly Lys Glu Glu Asn Glu His Val Arg Thr Gly Glu
                85                  90                  95
Ser Asn Gln Glu Met Glu Val Leu Ala Ser Lys Phe Ala His Arg
                100                 105                 110
Pro Ser Ala Pro Val His Arg Arg Ile Lys Glu Ser Pro Leu Ser Ser
                115                 120                 125
Asp Ala Ile Phe Lys Gln Ser His Ala Gly Leu Phe Asn Leu Cys Ile
    130                 135                 140
Val Val Leu Val Ala Val Asn Ser Arg Leu Ile Ile Glu Asn Leu Met
145                 150                 155                 160
Lys Tyr Gly Trp Leu Ile Asn Ser Gly Phe Trp Phe Ser Ser Thr Ser
                165                 170                 175
Leu Lys Asp Trp Pro Leu Leu Met Cys Cys Leu Ser Leu Pro Ile Phe
                180                 185                 190
Pro Leu Ala Ala Phe Phe Val Glu Lys Leu Val Leu Leu Lys Tyr Ile
                195                 200                 205
Ser Glu Cys Val Ala Val Phe Leu His Ile Leu Ile Thr Thr Ala Ala
    210                 215                 220
Ile Leu Tyr Pro Val Leu Val Ile Leu Arg Cys Asp Ser Ala Val Leu
225                 230                 235                 240
Ser Gly Val Thr Leu Met Leu Phe Ala Cys Ile Val Trp Leu Lys Leu
                245                 250                 255
Val Ser Tyr Ala His Ala Ser His Asp Met Arg Ala Leu Ala Lys Ser
                260                 265                 270
Leu Asp Lys Gly Glu Thr Leu Ser Gly Tyr Trp Asn Ser Asp Asp Ser
    275                 280                 285
Tyr Gly Ala Ser Phe Gln Ser Leu Ala Tyr Phe Met Val Ala Pro Thr
    290                 295                 300
Leu Cys Tyr Gln Pro Ser Tyr Pro Arg Thr Ser Cys Ile Arg Lys Gly
305                 310                 315                 320
Trp Val Val Arg Gln Leu Ile Lys Leu Ile Ile Phe Thr Gly Phe Met
                325                 330                 335
Gly Phe Ile Val Glu Gln Tyr Ile Asn Pro Ile Val Arg Asn Ser Gln
                340                 345                 350
His Pro Leu Lys Gly Asn Leu Leu Tyr Ala Ile Glu Arg Val Leu Lys
                355                 360                 365
Leu Ser Val Pro Asn Leu Tyr Val Trp Leu Cys Met Phe Tyr Cys Phe
                370                 375                 380
Phe His Leu Trp Leu Asn Ile Leu Ala Glu Leu Leu Cys Phe Gly Asp
385                 390                 395                 400
Arg Glu Phe Tyr Lys Asp Trp Asn Ala Lys Thr Val Glu Glu Tyr
                405                 410                 415
Trp Arg Met Trp Asn Met Pro Val His Lys Trp Met Val Arg His Ile
                420                 425                 430
```

```
Tyr Phe Pro Cys Leu Arg Asn Gly Met Pro Arg Gly Gly Ala Ile Leu
            435                 440                 445

Ile Ala Phe Leu Ile Ser Ala Ile Phe His Glu Leu Cys Ile Ala Val
    450                 455                 460

Pro Cys His Ile Phe Lys Phe Trp Ala Phe Gly Ile Met Phe Gln
465                 470                 475                 480

Val Pro Leu Val Ile Leu Thr Asn Tyr Leu Gln Asp Lys Phe Gln Asn
                485                 490                 495

Ser Met Val Gly Asn Met Ile Phe Trp Cys Phe Phe Ser Ile Leu Gly
                500                 505                 510

Gln Pro Met Cys Leu Leu Leu Tyr Tyr His Asp Leu Met Asn Arg Lys
            515                 520                 525

Ala Ser Ala Lys
            530

<210> SEQ ID NO 42
<211> LENGTH: 477
<212> TYPE: PRT
<213> ORGANISM: Oryza sativa

<400> SEQUENCE: 42

Met Ala Pro Pro Ser Leu Ala Pro Asp Arg Gly Gly Gly Glu Pro
1               5                   10                  15

Asp Asp Ala Leu Arg Leu Arg Ala Arg Ala Ala Ala Ala Gly Asp
            20                  25                  30

Ala Pro Ala Pro Gln Gln Gln Glu Gln Arg His Gln Glu Gln Gln
        35                  40                  45

Gln Gln Leu Leu Trp Tyr Arg Ala Ser Ala Pro Ala His Arg Arg Val
    50                  55                  60

Arg Glu Ser Pro Leu Ser Ser Asp Ala Ile Phe Arg Gln Ser His Ala
65                  70                  75                  80

Gly Leu Leu Asn Leu Cys Ile Val Val Leu Val Ala Val Asn Ser Arg
                85                  90                  95

Leu Ile Ile Glu Asn Leu Met Lys Tyr Gly Leu Leu Ile Arg Ala Gly
            100                 105                 110

Phe Trp Phe Ser Gly Thr Ser Leu Ala Asp Trp Pro Leu Leu Met Cys
        115                 120                 125

Cys Leu Thr Leu Pro Thr Phe Pro Leu Ala Ala Leu Met Val Glu Lys
    130                 135                 140

Leu Ala Gln Arg Lys Leu Ile Ser Lys His Val Val Ile Leu Leu His
145                 150                 155                 160

Ile Val Ile Thr Thr Ser Val Leu Val Tyr Pro Val Val Ile Leu
                165                 170                 175

Lys Cys Asp Ser Ala Val Leu Ser Gly Phe Val Leu Met Phe Leu Ala
            180                 185                 190

Ser Ile Ile Trp Leu Lys Leu Val Ser Phe Ala His Thr Asn Tyr Asp
        195                 200                 205

Ile Arg Met Leu Ser Lys Ser Ile Glu Lys Gly Val Thr His Asp Ile
    210                 215                 220

Ser Ile Asp Pro Glu Asn Ile Lys Trp Pro Thr Phe Lys Arg Leu Ser
225                 230                 235                 240

Tyr Phe Met Leu Ala Pro Thr Leu Cys Tyr Gln Pro Ser Tyr Pro Arg
                245                 250                 255

Thr Thr Tyr Ile Arg Lys Gly Trp Val Val Arg Gln Leu Ile Lys Cys
```

```
                    260                 265                 270
Leu Val Phe Thr Gly Leu Met Gly Phe Ile Glu Gln Tyr Ile Asn
                275                 280                 285

Pro Ile Val Lys Asn Ser Lys His Pro Leu Lys Gly Asn Phe Leu Asn
290                 295                 300

Ala Ile Glu Arg Val Leu Lys Leu Ser Val Pro Thr Leu Tyr Val Trp
305                 310                 315                 320

Leu Cys Met Phe Tyr Cys Phe Phe His Leu Trp Leu Asn Ile Leu Ala
                325                 330                 335

Glu Leu Leu Cys Phe Gly Asp Arg Glu Phe Tyr Lys Asp Trp Trp Asn
                340                 345                 350

Ala Lys Thr Val Glu Glu Tyr Trp Arg Met Trp Asn Met Pro Val His
                355                 360                 365

Lys Trp Val Ile Arg His Ile Tyr Phe Pro Cys Ile Arg Asn Gly Phe
370                 375                 380

Ser Lys Val Ile Ser Ile Cys Ile Ile Tyr Phe Ile Val Leu Ile Asp
385                 390                 395                 400

Leu Gln Leu Cys Val Ala Val Pro Cys His Ile Phe Lys Phe Trp Ala
                405                 410                 415

Phe Ile Gly Ile Met Phe Gln Ile Pro Leu Val Phe Leu Thr Lys Tyr
                420                 425                 430

Leu Gln Asp Lys Phe Asn Asn Thr Met Val Gly Asn Met Ile Phe Trp
                435                 440                 445

Phe Phe Phe Ser Ile Leu Gly Gln Pro Met Cys Val Leu Leu Tyr Tyr
                450                 455                 460

His Asp Val Met Asn Arg Gln Gln Ala Gln Thr Asn Arg
465                 470                 475

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 43

His His His His His His
1               5

<210> SEQ ID NO 44
<211> LENGTH: 7
<212> TYPE: PRT
<213> ORGANISM: Cuphea pulcherrima

<400> SEQUENCE: 44

Gly His Leu Arg Ile Asp Arg
1               5

<210> SEQ ID NO 45
<211> LENGTH: 6
<212> TYPE: PRT
<213> ORGANISM: Cuphea pulcherrima

<400> SEQUENCE: 45

Phe Pro Glu Gly Thr Arg
1               5

<210> SEQ ID NO 46
```

```
<211> LENGTH: 8
<212> TYPE: PRT
<213> ORGANISM: Cuphea pulcherrima

<400> SEQUENCE: 46

Leu Pro Ile Val Pro Ile Val Leu
1               5

<210> SEQ ID NO 47
<211> LENGTH: 6
<212> TYPE: PRT
<213> ORGANISM: Cuphea pulcherrima

<400> SEQUENCE: 47

Leu Pro Val Leu Gly Trp
1               5

<210> SEQ ID NO 48
<211> LENGTH: 11
<212> TYPE: PRT
<213> ORGANISM: Cuphea pulcherrima

<400> SEQUENCE: 48

Asn Val Leu Ile Pro Arg Thr Lys Gly Phe Val
1               5                   10

<210> SEQ ID NO 49
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ctaggatcca ccatggctca tgaggcagtc ag                             32

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ctaggatcca ccatggctga ggcagtcagc                                30

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gtcggatcca ccatggctca ccggacttca                                30

<210> SEQ ID NO 52
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 52
atatctagac tagtcgatcc ttaatcctc                                29

<210> SEQ ID NO 53
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
atagcggccg catgcatgag gcagtcag                                 28

<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
atagcggccg catggctcac cggacttca                                29

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
aatgcggccg cctagtcgat ccttaat                                  27

<210> SEQ ID NO 56
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ctaggatcca ccatgcggga ggagacgaa                                29

<210> SEQ ID NO 57
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
atatctagat caaaggattc tcagtttga                                29

<210> SEQ ID NO 58
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
```
ctaggatcca ccatgatagg gttcaatga                                29

<210> SEQ ID NO 59
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
atatctagat cacaaaattc tcagttcga                                29

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ctaaagctta ccatgggaga ggaggcggac                               30

<210> SEQ ID NO 61
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
atactcgagt taaagtattc tcagtttga                                29

<210> SEQ ID NO 62
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ctaggatcca ccatggcgat tttggattc                                29

<210> SEQ ID NO 63
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
atatctagat catgacatcg atccttttc                                29

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
atagcggccg catggcgatt ttggatt                                    27

<210> SEQ ID NO 65
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tatgcggccg ctcatgacat cgatccttt                                  29

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cttcaatctc tgtatggtca ctctc                                      25

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gacatcaagg cacaatcaaa tctc                                       24

<210> SEQ ID NO 68
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ggagattcgc gaggagctta agtagg                                     26

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
catatggaat gtctcctgca caccac                                     26

<210> SEQ ID NO 70
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gagcgagatg ctgagattgt gttcct                                     26

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
tcactgtgca cctcattcac ctcttc                                           26

<210> SEQ ID NO 72
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
tggtgtgcag gagacattct acatgg                                           26

<210> SEQ ID NO 73
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
acttgtgcct tgtgtcgctc gaatag                                           26

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
ttgctttgga ctacgagcag gaga                                             24

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
tggagttgta agtcgtctcg tgga                                             24

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
ggtgaagcgt gacgaactga c                                                21

```
<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ctctagtgtt ctggtccatg tctcc                                          25
```